United States Patent
Weiss et al.

(10) Patent No.: US 9,828,313 B2
(45) Date of Patent: Nov. 28, 2017

(54) SYSTEMS AND METHODS FOR SEPARATION AND PURIFICATION OF PRODUCTS

(71) Applicant: Calera Corporation, Los Gatos, CA (US)

(72) Inventors: Michael Joseph Weiss, Los Gatos, CA (US); Ryan J Gilliam, San Jose, CA (US); Kyle Self, San Jose, CA (US); Gal Mariansky, Morgan Hill, CA (US); Margarete K Leclerc, Mountain View, CA (US); Riyaz Mohammed Shipchandler, San Jose, CA (US); Jacob Nagar, Santa Cruz, CA (US)

(73) Assignee: Calera Corporation, Moss Landing, CA (US)

(*) Notice: Subject to any disclaimer, the term of this patent is extended or adjusted under 35 U.S.C. 154(b) by 384 days.

(21) Appl. No.: 14/446,791

(22) Filed: Jul. 30, 2014

(65) Prior Publication Data
US 2015/0038750 A1    Feb. 5, 2015

Related U.S. Application Data

(60) Provisional application No. 61/860,705, filed on Jul. 31, 2013, provisional application No. 61/927,167, (Continued)

(51) Int. Cl.
*C07C 17/02* (2006.01)
*C25B 1/00* (2006.01)
(Continued)

(52) U.S. Cl.
CPC ............ *C07C 17/02* (2013.01); *C25B 1/00* (2013.01); *C25B 1/26* (2013.01); *C25B 1/46* (2013.01); *C25B 3/02* (2013.01); *C25B 9/08* (2013.01)

(58) Field of Classification Search
CPC .. C07C 17/02; C25B 1/00; C25B 1/26; C25B 1/46; C25B 3/02; C25B 9/08
See application file for complete search history.

(56) References Cited

U.S. PATENT DOCUMENTS

| 2,792,342 A | 5/1957 | Tuwiner |
| 3,079,444 A * | 2/1963 | Jacobowsky ........... C07C 17/02 570/216 |

(Continued)

FOREIGN PATENT DOCUMENTS

| CA | 1339833 C | 4/1998 |
| CN | 103238233 B | 9/2015 |

(Continued)

OTHER PUBLICATIONS

Krishnamoorthy, et al. Chlorination of substituted aromatics on graphite anode. Asian Journal of Chemistry. 2002; 14(3-4):1801-1803.

(Continued)

*Primary Examiner* — Ciel P Thomas
(74) *Attorney, Agent, or Firm* — Calera Corporation; Vandana Bansal

(57) ABSTRACT

There are provided methods and systems for an electrochemical cell including an anode and a cathode where the anode is contacted with a metal ion that converts the metal ion from a lower oxidation state to a higher oxidation state. The metal ion in the higher oxidation state is reacted with an unsaturated hydrocarbon and/or a saturated hydrocarbon to form products. Separation and/or purification of the products as well as of the metal ions in the lower oxidation state and the higher oxidation state, is provided herein.

12 Claims, 19 Drawing Sheets

Related U.S. Application Data filed on Jan. 14, 2014, provisional application No. 61/952,685, filed on Mar. 13, 2014.

(51) Int. Cl.
| | | |
|---|---|---|
| C25B 1/26 | (2006.01) | |
| C25B 1/46 | (2006.01) | |
| C25B 3/02 | (2006.01) | |
| C25B 9/08 | (2006.01) | |

(56) References Cited

U.S. PATENT DOCUMENTS

| | | |
|---|---|---|
| 3,214,481 A | 10/1965 | Heinemann et al. |
| 3,214,482 A | 10/1965 | Caropreson et al. |
| 3,437,712 A | 4/1969 | Knarr et al. |
| 3,461,180 A | 8/1969 | Heinemann et al. |
| 3,510,532 A | 5/1970 | Caropreso et al. |
| 3,635,803 A | 1/1972 | Thomas et al. |
| 3,691,239 A | 9/1972 | Homer et al. |
| 3,985,794 A | 10/1976 | Calcagno et al. |
| 4,108,752 A | 8/1978 | Pohto et al. |
| 4,111,779 A | 9/1978 | Seko et al. |
| 4,190,508 A | 2/1980 | Kametani et al. |
| 4,256,719 A | 3/1981 | Van Andel |
| 4,319,977 A | 3/1982 | Wortley |
| 4,324,625 A | 4/1982 | Cumbo |
| 4,376,019 A | 3/1983 | Gamlen et al. |
| 4,379,019 A | 4/1983 | Gamien et al. |
| 4,394,227 A | 7/1983 | Jager et al. |
| 4,402,811 A | 9/1983 | Klotz et al. |
| 4,555,317 A | 11/1985 | Nicolas et al. |
| 4,595,469 A | 6/1986 | Foller |
| 4,643,818 A | 2/1987 | Seko et al. |
| 4,672,142 A | 6/1987 | Hundeck et al. |
| 4,726,887 A | 2/1988 | McIntyre |
| 4,767,519 A | 8/1988 | De Nora |
| 4,814,420 A | 3/1989 | Brunelle et al. |
| 4,834,847 A | 5/1989 | Mcintyre |
| 4,950,268 A | 8/1990 | Rink |
| 4,950,368 A | 8/1990 | Weinberg et al. |
| 5,050,603 A * | 9/1991 | Stokes ............... B67D 9/00 123/523 |
| 5,296,107 A | 3/1994 | Harrison |
| 5,437,771 A | 8/1995 | Shimamune et al. |
| 5,595,641 A | 1/1997 | Traini et al. |
| 5,891,318 A | 4/1999 | Freire et al. |
| 5,932,750 A | 8/1999 | Hayashi et al. |
| 6,117,286 A | 9/2000 | Shimamune et al. |
| 6,146,787 A | 11/2000 | Harrup et al. |
| 6,368,473 B1 | 4/2002 | Furuya et al. |
| 6,372,102 B1 | 4/2002 | Sakata et al. |
| 6,383,349 B1 | 5/2002 | Sakata et al. |
| 6,395,153 B1 | 5/2002 | Matousek et al. |
| 7,404,878 B2 | 7/2008 | Katayama et al. |
| 7,569,083 B2 | 8/2009 | Katayama et al. |
| 7,658,835 B2 | 2/2010 | Gestermann et al. |
| 7,708,867 B2 | 5/2010 | Yamada et al. |
| 7,735,274 B2 | 6/2010 | Constantz et al. |
| 7,744,761 B2 | 6/2010 | Constantz et al. |
| 7,749,476 B2 | 7/2010 | Constantz et al. |
| 7,753,618 B2 | 7/2010 | Constantz et al. |
| 7,754,169 B2 | 7/2010 | Constantz et al. |
| 7,771,684 B2 | 8/2010 | Constantz et al. |
| 7,790,012 B2 | 9/2010 | Kirk et al. |
| 7,815,880 B2 | 10/2010 | Constantz et al. |
| 7,829,053 B2 | 11/2010 | Constantz et al. |
| 7,837,842 B1 | 11/2010 | Mayers, Sr. et al. |
| 7,875,163 B2 | 1/2011 | Gilliam et al. |
| 7,887,694 B2 | 2/2011 | Constantz et al. |
| 7,906,028 B2 | 3/2011 | Constantz et al. |
| 7,914,652 B2 | 3/2011 | Yamada et al. |
| 7,914,685 B2 | 3/2011 | Constantz et al. |
| 7,922,809 B1 | 4/2011 | Constantz et al. |
| 7,931,809 B2 | 4/2011 | Constantz et al. |
| 7,939,336 B2 | 5/2011 | Constantz et al. |
| 7,966,250 B2 | 6/2011 | Constantz et al. |
| 7,933,511 B2 | 8/2011 | Gilliam et al. |
| 7,993,500 B2 | 8/2011 | Gilliam et al. |
| 7,993,511 B2 | 8/2011 | Gilliam et al. |
| 8,006,446 B2 | 8/2011 | Constantz et al. |
| 8,062,418 B2 | 11/2011 | Constantz et al. |
| 8,114,214 B2 | 2/2012 | Constantz et al. |
| 8,137,455 B1 | 3/2012 | Constantz et al. |
| 8,197,649 B2 | 6/2012 | Saiki et al. |
| 8,940,139 B2 | 1/2015 | Asaumi et al. |
| 9,108,844 B2 | 8/2015 | Huss |
| 9,175,410 B2 | 11/2015 | Izawa et al. |
| 9,181,624 B2 | 11/2015 | Sugiyama et al. |
| 9,187,834 B2 | 11/2015 | Albrecht et al. |
| 9,187,835 B2 | 11/2015 | Albrecht et al. |
| 9,200,375 B2 | 12/2015 | Gilliam et al. |
| 9,273,404 B2 | 3/2016 | Bulan et al. |
| 2003/0150819 A1 | 8/2003 | Iseki et al. |
| 2004/0251199 A1 | 12/2004 | Benavides |
| 2004/0267063 A1 | 12/2004 | Harth et al. |
| 2006/0124445 A1 | 6/2006 | Labrecque et al. |
| 2007/0292762 A1 | 12/2007 | Johnson |
| 2008/0023339 A1 | 1/2008 | Berggren et al. |
| 2008/0029404 A1 | 2/2008 | Weber et al. |
| 2008/0223727 A1 | 9/2008 | Oloman et al. |
| 2008/0275279 A1 * | 11/2008 | Podkolzin ............ B01J 27/08 585/359 |
| 2009/0001020 A1 | 1/2009 | Constantz et al. |
| 2009/0020044 A1 | 1/2009 | Constantz et al. |
| 2009/0029199 A1 | 1/2009 | Tao et al. |
| 2009/0087698 A1 | 4/2009 | Huth et al. |
| 2009/0169452 A1 | 7/2009 | Constantz et al. |
| 2009/0202410 A1 | 8/2009 | Kawatra et al. |
| 2009/0301352 A1 | 12/2009 | Constantz et al. |
| 2009/0325031 A1 | 12/2009 | Sugawara et al. |
| 2010/0000444 A1 | 1/2010 | Constantz et al. |
| 2010/0024686 A1 | 2/2010 | Constantz et al. |
| 2010/0032347 A1 * | 2/2010 | Ring ............... B01J 8/0453 208/264 |
| 2010/0041927 A1 | 2/2010 | Olver et al. |
| 2010/0051469 A1 | 3/2010 | Stolberg |
| 2010/0051859 A1 | 3/2010 | House et al. |
| 2010/0063902 A1 | 3/2010 | Constantz et al. |
| 2010/0077691 A1 | 4/2010 | Constantz et al. |
| 2010/0077922 A1 | 4/2010 | Constantz et al. |
| 2010/0083880 A1 | 4/2010 | Constantz et al. |
| 2010/0084280 A1 | 4/2010 | Gilliam et al. |
| 2010/0108537 A1 | 5/2010 | Perego et al. |
| 2010/0111810 A1 | 5/2010 | Constantz et al. |
| 2010/0116683 A1 | 5/2010 | Gilliam et al. |
| 2010/0132556 A1 | 6/2010 | Constantz et al. |
| 2010/0132591 A1 | 6/2010 | Constantz et al. |
| 2010/0135865 A1 | 6/2010 | Constantz et al. |
| 2010/0135882 A1 | 6/2010 | Constantz et al. |
| 2010/0140103 A1 | 6/2010 | Gilliam et al. |
| 2010/0144521 A1 | 6/2010 | Constantz et al. |
| 2010/0150802 A1 | 6/2010 | Gilliam et al. |
| 2010/0154679 A1 | 6/2010 | Constantz et al. |
| 2010/0155258 A1 | 6/2010 | Kirk et al. |
| 2010/0158786 A1 | 6/2010 | Constantz et al. |
| 2010/0179302 A1 * | 7/2010 | Krafft ............... C07C 29/62 528/421 |
| 2010/0196104 A1 | 8/2010 | Constantz et al. |
| 2010/0200419 A1 | 8/2010 | Gilliam et al. |
| 2010/0219373 A1 | 9/2010 | Seeker et al. |
| 2010/0224503 A1 | 9/2010 | Kirk et al. |
| 2010/0229725 A1 | 9/2010 | Farsad et al. |
| 2010/0230293 A1 | 9/2010 | Gilliam et al. |
| 2010/0230830 A1 | 9/2010 | Farsad et al. |
| 2010/0236242 A1 | 9/2010 | Farsad et al. |
| 2010/0239467 A1 | 9/2010 | Constantz et al. |
| 2010/0239487 A1 | 9/2010 | Constantz et al. |
| 2010/0247410 A1 | 9/2010 | Constantz et al. |
| 2010/0258035 A1 | 10/2010 | Constantz et al. |
| 2010/0258506 A1 | 10/2010 | Berkowitz et al. |
| 2010/0270167 A1 * | 10/2010 | McFarland ............ C07C 1/26 205/462 |
| 2010/0276299 A1 | 11/2010 | Kelly et al. |
| 2010/0290967 A1 | 11/2010 | Detournay et al. |

(56) References Cited

U.S. PATENT DOCUMENTS

| | | |
|---|---|---|
| 2010/0313793 A1 | 12/2010 | Constantz et al. |
| 2010/0313794 A1 | 12/2010 | Constantz et al. |
| 2010/0319586 A1 | 12/2010 | Blount et al. |
| 2010/0326328 A1 | 12/2010 | Constantz et al. |
| 2011/0005938 A1 | 1/2011 | Wolf et al. |
| 2011/0028765 A1* | 2/2011 | Mehta .................. B01D 3/143 568/841 |
| 2011/0030586 A1 | 2/2011 | Constantz et al. |
| 2011/0030957 A1 | 2/2011 | Constantz et al. |
| 2011/0033239 A1 | 2/2011 | Constantz et al. |
| 2011/0035154 A1 | 2/2011 | Kendall et al. |
| 2011/0036728 A1 | 2/2011 | Farsad et al. |
| 2011/0042230 A1 | 2/2011 | Gilliam et al. |
| 2011/0054084 A1 | 3/2011 | Constantz et al. |
| 2011/0059000 A1 | 3/2011 | Constantz et al. |
| 2011/0067600 A1 | 3/2011 | Constantz et al. |
| 2011/0067603 A1 | 3/2011 | Constantz et al. |
| 2011/0067605 A1 | 3/2011 | Constantz et al. |
| 2011/0071309 A1 | 3/2011 | Constantz et al. |
| 2011/0076587 A1 | 3/2011 | Wang et al. |
| 2011/0079515 A1 | 4/2011 | Gilliam et al. |
| 2011/0083968 A1 | 4/2011 | Gilliam et al. |
| 2011/0091366 A1 | 4/2011 | Kendall et al. |
| 2011/0091955 A1 | 4/2011 | Constantz et al. |
| 2011/0120888 A1 | 5/2011 | James et al. |
| 2011/0132234 A1 | 6/2011 | Constantz et al. |
| 2011/0147227 A1 | 6/2011 | Gilliam et al. |
| 2011/0152580 A1* | 6/2011 | Hook .................. B01D 3/14 568/841 |
| 2011/0203489 A1 | 8/2011 | Constantz et al. |
| 2011/0226989 A9 | 9/2011 | Seeker et al. |
| 2011/0240916 A1 | 10/2011 | Constantz et al. |
| 2011/0247336 A9 | 10/2011 | Farsad et al. |
| 2011/0277474 A1 | 11/2011 | Constantz et al. |
| 2011/0277670 A1 | 11/2011 | Self et al. |
| 2011/0315561 A1 | 12/2011 | Rabaey et al. |
| 2012/0000789 A1 | 1/2012 | Turek et al. |
| 2012/0152804 A1* | 6/2012 | Koseoglu .................. C10G 21/00 208/80 |
| 2012/0292196 A1 | 11/2012 | Albrecht et al. |
| 2012/0292197 A1 | 11/2012 | Albrecht et al. |
| 2013/0206606 A1 | 8/2013 | Gilliam et al. |
| 2013/0240372 A1 | 9/2013 | Bulan et al. |
| 2014/0353146 A1 | 12/2014 | Gilliam et al. |
| 2015/0038750 A1 | 2/2015 | Weiss et al. |
| 2015/0337443 A1 | 11/2015 | Albrecht et al. |
| 2015/0361564 A1 | 12/2015 | Albrecht et al. |
| 2016/0002803 A1 | 1/2016 | Sklar |
| 2016/0040304 A1 | 2/2016 | Albrecht et al. |
| 2016/0060774 A1 | 3/2016 | Gilliam et al. |
| 2016/0076156 A1 | 3/2016 | Albrecht et al. |
| 2016/0108529 A1 | 4/2016 | Albrecht et al. |
| 2016/0230291 A1 | 8/2016 | Albrecht et al. |
| 2017/0073823 A1 | 3/2017 | Albrecht et al. |

FOREIGN PATENT DOCUMENTS

| | | |
|---|---|---|
| EP | 0039547 A1 | 11/1981 |
| EP | 0039547 B1 | 7/1984 |
| EP | 1362133 A1 | 11/2003 |
| EP | 2253600 A1 | 11/2010 |
| EP | 1362133 B1 | 7/2011 |
| EP | 2697410 B1 | 6/2015 |
| FR | 1539499 A | 9/1968 |
| GB | 812680 A | 4/1959 |
| GB | 1019437 A | 2/1966 |
| JP | S56169631 A | 12/1981 |
| JP | 57-027129 A | 2/1982 |
| JP | 55874624 A | 5/1983 |
| JP | 63-293186 A | 11/1988 |
| JP | H 0238573 B2 | 8/1990 |
| JP | H 0356683 A | 3/1991 |
| JP | H046290 A | 1/1992 |
| JP | H 0432594 A | 2/1992 |
| JP | H 05214573 A | 8/1993 |
| JP | H 1081986 A | 3/1998 |
| JP | H 11256385 A | 9/1999 |
| JP | 2000-199093 A | 7/2000 |
| JP | 2001-262387 A | 9/2001 |
| JP | 2004-027267 A | 1/2004 |
| JP | 2005511670 A | 4/2005 |
| JP | 2009-299111 A | 12/2009 |
| TW | 201313958 A | 4/2013 |
| WO | WO 2004/097073 A1 | 11/2004 |
| WO | WO-2007058472 A1 | 5/2007 |
| WO | WO 2008/018928 A2 | 2/2008 |
| WO | WO 2008/148055 A1 | 12/2008 |
| WO | WO 2009/006295 A2 | 1/2009 |
| WO | WO 2009/086460 A1 | 7/2009 |
| WO | WO 2009/146436 A1 | 12/2009 |
| WO | WO 2009/155378 A1 | 12/2009 |
| WO | WO 2010/006242 A1 | 1/2010 |
| WO | WO 2010/008896 A1 | 1/2010 |
| WO | WO 2010/009273 A1 | 1/2010 |
| WO | WO 2010/030826 A1 | 3/2010 |
| WO | WO 2010/039903 A1 | 4/2010 |
| WO | WO 2010/039909 A1 | 4/2010 |
| WO | WO 2010/048457 A1 | 4/2010 |
| WO | WO 2010/051458 A1 | 5/2010 |
| WO | WO 2010/055152 A1 | 5/2010 |
| WO | WO-2010055152 A1 | 5/2010 |
| WO | WO 2010/068924 A1 | 6/2010 |
| WO | WO 2010/074686 A1 | 7/2010 |
| WO | WO 2010/074687 A1 | 7/2010 |
| WO | WO 2010/087823 A1 | 8/2010 |
| WO | WO 2010/091029 A1 | 8/2010 |
| WO | WO 2010/093713 A1 | 8/2010 |
| WO | WO 2010/093716 A1 | 8/2010 |
| WO | WO 2010/101953 A1 | 9/2010 |
| WO | WO 2010/104989 A1 | 9/2010 |
| WO | WO 2010/132863 A1 | 11/2010 |
| WO | WO 2010/136744 A1 | 12/2010 |
| WO | WO 2011/008223 A1 | 1/2011 |
| WO | WO 2011/017609 A1 | 2/2011 |
| WO | WO 2011/038076 A1 | 3/2011 |
| WO | WO 2011/049996 A1 | 4/2011 |
| WO | WO 2011/066293 A1 | 6/2011 |
| WO | WO 2011/073621 A1 | 6/2011 |
| WO | WO 2011/075680 A1 | 6/2011 |
| WO | WO 2011/081681 A1 | 7/2011 |
| WO | WO 2011/097468 A2 | 8/2011 |
| WO | WO 2011/102868 A1 | 8/2011 |
| WO | WO 2011/116236 A2 | 9/2011 |
| WO | WO 2012/158969 A1 | 11/2012 |
| WO | WO-2013082811 A1 | 6/2013 |
| WO | WO 2013/0148216 A1 | 10/2013 |

OTHER PUBLICATIONS

Office action dated Jun. 11, 2015 for U.S. Appl. No. 13/799,131.
Office action dated Jul. 9, 2015 for U.S. Appl. No. 13/474,598.
Office action dated Aug. 6, 2015 for U.S. Appl. No. 13/474,598.
Wikipedia definition of "Aqueous Solution". Accessed Jul. 29, 2015. 2 pages.
Wikipedia definition of "Solvent". Accessed Jul. 29, 2015. 14 pages.
U.S. Appl. No. 14/855,252, filed Sep. 15, 2015, Albrecht et al.
U.S. Appl. No. 14/876,760, filed Oct. 6, 2015, Albrecht et al.
U.S. Appl. No. 14/877,329, filed Oct. 7, 2015, Albrecht et al.
U.S. Appl. No. 14/879,525, filed Oct. 9, 2015, Albrecht et al.
U.S. Appl. No. 14/919,281, filed Oct. 21, 2015, Gilliam et al.
Logager, et al. Oxidation of Ferrous Ions by Ozone in Acidic Solutions. Inorg. Chem. 1992; 31:3523-3529.
International search report and written opinion dated Dec. 17, 2015 for PCT/US2015/050196.
European search report and opinion dated May 11, 2015 for EP Application No. 13769321.4.
Kotora, et al. Selective Additions of Polyhalognated Compounds to Chloro Substituted Ethenes Catalyzed by a Copper Complex. React. Kinet. Catal. Lett. (no month, 1991), vol. 44, No. 2, pp. 415-419.

(56) References Cited

OTHER PUBLICATIONS

Margraf, et al. Copper(II) PMDTA and Copper(II) TMEDA Complexes: Precursors for the Synthesis of Dinuclear Copper(II) Complexes. Inorgancia Chimica Acta (no month, 2005), vol. 358, pp. 1193-1203.
Office action dated Apr. 23, 2015 for U.S. Appl. No. 13/474,599.
Yuan, et al. Direct Electrochemical Synthesis and Crystal Structure of a Copper(II) Complex with a Chiral (S)-2-(diphenylmethanol-1-(2-pyridylmethyl)pyrrolidine. Inorganic Chemistry Communications (no month, 2005), vol. 8, pp. 1014-1017.
Acquah, et al. The electrochlorination of aliphatic hydrocarbons. J. Appl. Chem. Biotechnol. 1972; 22:1195-1200.
European search report and opinion dated Feb. 25, 2015 for EP Application No. 12785945.2.
Office action dated Mar. 4, 2015 for U.S. Appl. No. 13/474,598.
Rollin, et al. The electrochemistry of nickel complexes with triphenylphosphine and ethylene in methylpyrrolidinone. Journal of Electroanalytical Chemistry and Interfacial Electrochemistry. 1985; 183(1-2):247-260.
Rorabacher. Electron transfer by copper centers. Chemical Centers. 2004; 104(2):651-698.
U.S. Appl. No. 14/460,697, filed Aug. 15, 2014, Gilliam et al.
International search report and written opinion dated Oct. 15, 2014 for PCT/US2014/048976.
U.S. Appl. No. 13/799,131, filed Mar. 13, 2013, Gilliam et al.
Benadda, B. et al. 1996. A study of Oxygen Absorption Kinetics in Ionic Cu(I) Aqueous Solutions. Chem. Eng. Technol. 19: 34-38.
Brugger, et al. UV-Vis-NIR spectroscopic study of Cu(II) complexing in LiCl brines between 20° C. and 90° C.. Geochimica et Cosmochimica Acta. 2001; 65(16):2691-2708.
Constantz, B. (2009) "The Risk of Implementing New Regulations on Game-Changing Technology: Sequestering CO2 in the Built Environment" AGU, 90(22), Jt. Assem, Suppl., Abstract.
Friend, L. et al. 1974. Liquid-Phase Oxychlorination of Ethylene to Produce Vinyl Chloride. Homogeneous Catalysis. American Chemical Society. Piscataway, N.J. pp. 168-176.
Georgiadou, M. et al. 1998. Modelling of copper etching in aerated chloride solutions. Journal of Applied Electrochemistry. 28: 127-134.
Hine, F. et al. 1970. Mechanism of Oxidation of Cuprous Ion in Hydrochloric Acid Solution by Oxygen. Electrochimica Acta. 15: 769-781.
International search report and written opinion dated May 23, 2013 for PCT/US2013/031064.
International search report and written opinion dated Aug. 14, 2012 for PCT/US2012/038438.
Jhaveri, A.S., et al. 1967. Kinetics of absorption of oxygen in aqueous solutions of cuprous chloride. Chemical Engineering Science. 22: 1-6.
Kinoshita, et al. Mass-Transfer Study of Carbon Felt, Flow-Through Electrode. J. Electrochem. Soc. 1982; 129(9):1993-1997.
Langer, et al. Electrogenerative and Voltameiotic Processes. Ind. Eng. Chem. Process Des. Dev. 1979; 18(4):567-579.
Liu, et al. A spectrophotometric study of aqueous copper(I)-chloride complexes in LiCl solutions between 100° C. and 250° C.. Geochimica et Cosmochimica Acta. 2002; 66(20):3615-3633.
Lundstrom, et al Redox potential characteristics of cupric chloride solutions. Hydrometallurgy. 2009; 95:285-289.
Powell, et al. Chemical speciation of environmentally significant metals with inorganic ligands. Pure Appl. Chem. 2007; 79(5):895-950.
Ralph, et al. Mass transport in an electrochemical laboratory filterpress reactor and its enhancement by turbulence promoters. Electrochemica Acta. 1996; 41(4):591-603.
Spector, M.L. et al. 1967. Olefin Chlorination in Homogeneous Aqueous Copper Chloride Solutions. Industrial & Engineering Chemistry Process Design and Development. 6(3): 327-331.
European search report with opinion dated Dec. 8, 2016 for EP14832631.7.
European search report with written opinion dated Feb. 17, 2017 for EP16188593.4.
Office action dated Apr. 18, 2017 for U.S. Appl. No. 14/460,697.
Office action dated Dec. 19, 2016 for U.S. Appl. No. 14/460,697.
Andersson, et al. High power diode laser cladding. Fabricating and Metalworking. Mar. 2014; 24-26.
Co-pending U.S. Appl. No. 15/341,260, filed Nov. 2, 2016.
Langer, et al. Electrogenerative Chlorination J. Electrochem. Soc. 1970; 117(4):510-511.
Office action dated Aug. 26, 2016 for U.S. Appl. No. 14/460,697.
International search report with written opinion dated Jul. 18, 2017 for EP17150726.
Office action dated Jul. 19, 2017 for U.S. Appl. No. 14/814,935.
Office action dated Aug. 7, 2017 for U.S. Appl. No. 14/834,151.
Office action dated Aug. 8, 2017 for U.S. Appl. No. 14/814,935.
Office action dated Aug. 8, 2017 for U.S. Appl. No. 14/876,760.
Office action dated Aug. 10, 2017 for U.S. Appl. No. 14/460,697.

* cited by examiner

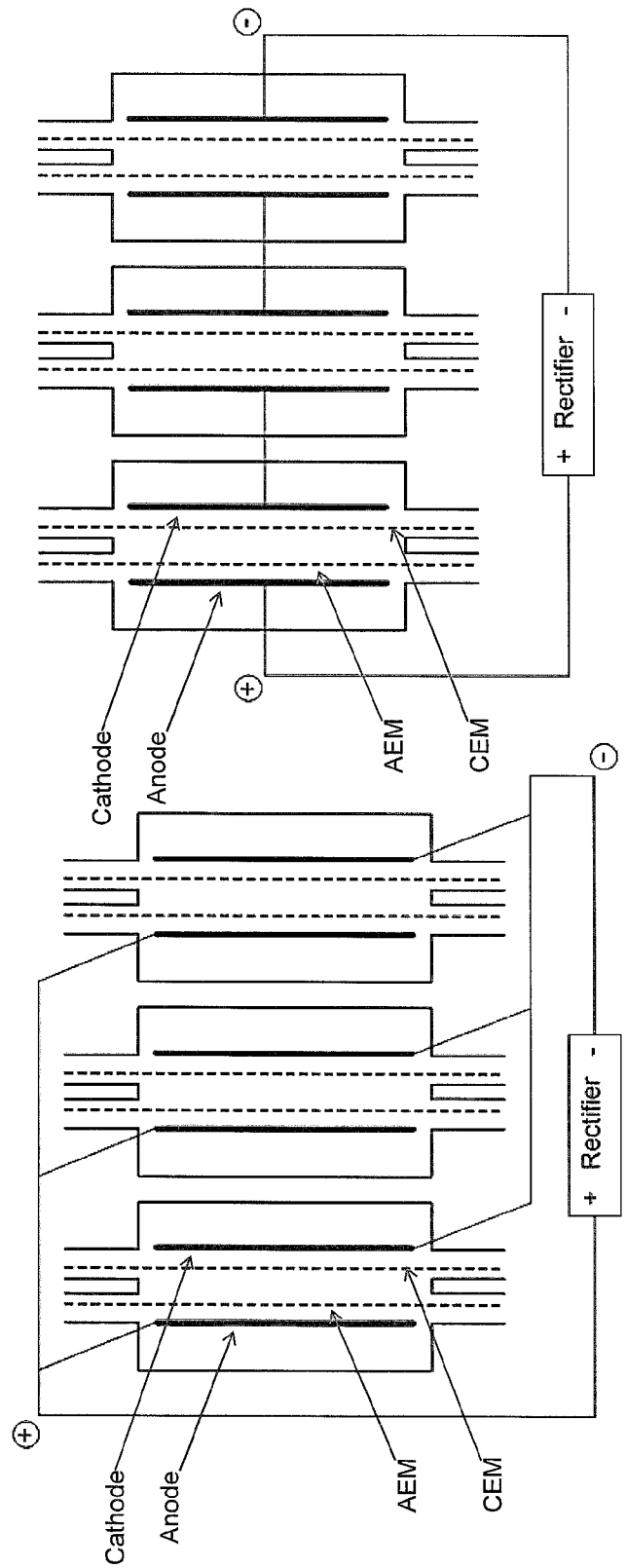

SYSTEMS AND METHODS FOR SEPARATION AND PURIFICATION OF PRODUCTS

CROSS-REFERENCE TO RELATED APPLICATIONS

This application claims priority to U.S. Provisional Patent Application No. 61/860,705, filed Jul. 31, 2013; U.S. Provisional Patent Application No. 61/927,167, filed Jan. 14, 2014; and U.S. Provisional Patent Application No. 61/952,685, filed Mar. 13, 2014, all of which are incorporated herein by reference in their entireties in the present disclosure.

GOVERNMENT SUPPORT

Work described herein was made in whole or in part with Government support under Award Number: DE-FE0002472 awarded by the Department of Energy. The Government has certain rights in this invention.

BACKGROUND

In many chemical processes, caustic soda may be required to achieve a chemical reaction, e.g., to neutralize an acid, or buffer pH of a solution, or precipitate an insoluble hydroxide from a solution. One method by which the caustic soda may be produced is by an electrochemical system. In producing the caustic soda electrochemically, such as via chlor-alkali process, a large amount of energy, salt, and water may be used.

Polyvinyl chloride, commonly known as PVC, may be the third-most widely-produced plastic, after polyethylene and polypropylene. PVC is widely used in construction because it is durable, cheap, and easily worked. PVC may be made by polymerization of vinyl chloride monomer which in turn may be made from ethylene dichloride. Ethylene dichloride may be made by direct chlorination of ethylene using chlorine gas made from the chlor-alkali process.

The production of chlorine and caustic soda by electrolysis of aqueous solutions of sodium chloride or brine is one of the electrochemical processes demanding high-energy consumption. The total energy requirement is for instance about 2% in the USA and about 1% in Japan of the gross electric power generated, to maintain this process by the chlor-alkali industry. The high energy consumption may be related to high carbon dioxide emission owing to burning of fossil fuels. Therefore, reduction in the electrical power demand needs to be addressed to curtail environment pollution and global warming.

SUMMARY

In one aspect, there is provided a system, comprising: an electrochemical system comprising an anode chamber comprising an anode in contact with an anode electrolyte comprising metal ions wherein the anode is configured to oxidize the metal ions from a lower oxidation state to a higher oxidation state; and a reactor operably connected to the anode chamber and configured to contact the anode electrolyte comprising the metal ions in the higher oxidation state with an unsaturated and/or saturated hydrocarbon to form one or more organic compounds comprising halogenated or sulfonated hydrocarbon and the metal ion in the lower oxidation state, wherein the reactor has a length:diameter ratio of between 2-40.

In some embodiments of the above noted aspect, the reactor is configured to produce the halogenated or sulfonated hydrocarbon with more than 0.5 STY or more than 80% selectivity. In some embodiments of the above noted aspect and embodiment, the reactor has a length/diameter ratio of between about 20-40. In some embodiments of the above noted aspect and embodiments, the reactor is a packed-bed reactor or a trickle-bed reactor. In some embodiments of the above noted aspect and embodiments, the reactor has a packing material comprising structured packing material, unstructured packing material, or combination thereof. In some embodiments of the above noted aspect and embodiments, the structured packing material comprises thin corrugated metal plates or gauzes. In some embodiments of the above noted aspect and embodiments, the unstructured packing material comprises raschig rings, pall rings, lessing rings, michael bialecki rings, berl saddles, intalox saddles, super intalox saddles, Tellerette® rings, or combinations thereof. In some embodiments of the above noted aspect and embodiments, diameter of the structured packing material is the diameter of the reactor. In some embodiments of the above noted aspect and embodiments, size of the unstructured packing material is between about ¼ of an inch to about 5 inches. In some embodiments of the above noted aspect and embodiments, the unsaturated hydrocarbon is ethylene, the halogenated hydrocarbon is ethylene dichloride, the metal ion is copper chloride, or combinations thereof. In some embodiments of the above noted aspect and embodiments, the electrochemical system further comprises a cathode chamber comprising a cathode in contact with a cathode electrolyte wherein the anode chamber and the cathode chamber are separated by an anion exchange membrane comprising a reinforcing material comprising polymer and wherein thickness of the membrane is between 20-130 um.

In another aspect, there is provided a system, comprising an electrochemical system comprising an anode chamber comprising an anode in contact with an anode electrolyte comprising metal ion wherein the anode is configured to oxidize the metal ion from a lower oxidation state to a higher oxidation state; a reactor operably connected to the anode chamber and configured to react an unsaturated hydrocarbon or saturated hydrocarbon in an aqueous medium with the anode electrolyte comprising the metal ion in the higher oxidation state to form one or more organic compounds comprising halogenated or sulfonated hydrocarbon and the metal ion in the lower oxidation state; and a separator configured to separate and purify the one or more organic compounds comprising halogenated or sulfonated hydrocarbon from the aqueous medium. In some embodiments of the aforementioned aspect, the separator comprises reaction separation reactor system, compression-cooling system, liquid-liquid separation system, vapor-liquid separation system, scrubbing system, purification subprocess system, adsorbent, or combinations thereof. In some embodiments of the aforementioned aspect and embodiments, the reactor is a reaction separation reactor. In some embodiments of the aforementioned aspect and embodiments, the reaction separation reactor is a reactive distillation reactor, reactive extraction reactor, or combination thereof. In some embodiments of the aforementioned aspect and embodiments, the liquid-liquid separation system comprises decanter, extractant, or combination thereof; the vapor-liquid separation system comprises flash column, a distillation column, or combination thereof; the purification subprocess system comprises decanter, sorbent, distillation column, or combinations thereof; and/or the scrubber comprises column comprising an alkali.

In some embodiments of the aforementioned aspects and embodiments, the separator is configured to produce the halogenated or sulfonated hydrocarbon with more than about 90% yield and/or more than about 90% purity. In some embodiments of the aforementioned aspects and embodiments, the aqueous medium obtained after the separator comprises the metal ion and less than about 1% or no organic compound. In some embodiments of the aforementioned aspect and embodiments, the reactor is a trickle-bed reactor. In some embodiments of the aforementioned aspect and embodiments, the reactor is a packed-bed reactor. In some embodiments of the aforementioned aspect and embodiments, the reactor has a length/diameter ratio of the reactor is between about 2-30; or between 4-25, or between 6-15; or between 2:1-10:1 or about 3:1 or about 4:1. In some embodiments of the aforementioned aspect and embodiments, the reactor has a packing material comprising structured or unstructured packing material. In some embodiments of the aforementioned aspect and embodiments, the structured packing material comprises thin corrugated metal plates or gauzes. In some embodiments of the aforementioned aspect and embodiments, the unstructured packing material comprises Raschig rings, Pall rings, Lessing rings, Michael Bialecki rings, Berl saddles, Intalox saddles, super intalox saddles, Tellerette® rings, or combinations thereof. In some embodiments of the aforementioned aspect and embodiments, the size of the packing material may be between about ¼ of an inch to about 5 inches. In some embodiments of the aforementioned aspect and embodiments, the unsaturated hydrocarbon is ethylene and the halogenated hydrocarbon is EDC. In some embodiments of the aforementioned aspect and embodiments, the metal ion is copper. In some embodiments of the aforementioned aspect and embodiments, the electrochemical system is made of corrosion resistant material comprising titanium. In some embodiments of the aforementioned aspect and embodiments, the electrochemical system comprises bipolar electrolyzers. In some embodiments of the aforementioned aspect and embodiments, the systems further include one or more heat exchange units. In some embodiments of the aforementioned aspect and embodiments, the one or more heat exchange units are configured to exchange heat between the anode electrolyte, the unsaturated or saturated hydrocarbon, the aqueous medium comprising the metal ion in the lower and higher oxidation state, steam, water, or combinations thereof.

In some embodiments of the foregoing systems, the unsaturated hydrocarbon (such as ethylene), the saturated hydrocarbon (such as formula III), the halogenated hydrocarbon, the metal ions, etc. have all been described in detail herein. In some embodiments of the foregoing systems, the metal ion is copper, the unsaturated hydrocarbon is ethylene, the organic compound comprises EDC, or combinations thereof.

In some embodiments of the aforementioned aspect and embodiments, the anode and the cathode is separated by anion exchange membrane comprising a reinforced material and a thickness of between 20-130 um or between 20-75 um or between 50-100 um. Such membranes have been described in detail herein. In some embodiments of the aforementioned aspect and embodiments, the anion exchange membrane separates a third electrolyte from the anode electrolyte. In some embodiments of the aforementioned aspect and embodiments, the anode and the cathode are further separated by a cation exchange membrane that separates the third electrolyte from the cathode electrolyte.

In some embodiments of the aforementioned aspect and embodiments, the separator further comprises a recirculating system operably connected to the anode to recirculate the aqueous medium comprising metal ion in the lower oxidation state to the anode electrolyte.

In some embodiments of the aforementioned aspect and embodiments, the anode is a diffusion enhancing anode such as, but not limited to, a porous anode. The porous anode may be flat or corrugated, as described herein.

In some embodiments of the aforementioned aspect and embodiments, the separator further comprises an adsorbent selected from activated charcoal, alumina, activated silica, polymer, and combinations thereof.

In some embodiments of the aforementioned aspect and embodiments, the system further comprises a ligand in the anode electrolyte wherein the ligand is configured to interact with the metal ion.

In some embodiments of the aforementioned system aspect and embodiments, the cathode is a gas-diffusion cathode configured to react oxygen gas and water to form hydroxide ions. In some embodiments of the aforementioned system aspect and embodiments, the cathode is a hydrogen gas producing cathode configured to form hydrogen gas and hydroxide ions by reducing water. In some embodiments of the aforementioned system aspect and embodiments, the cathode is a hydrogen gas producing cathode configured to reduce an acid, such as, hydrochloric acid to hydrogen gas. In some embodiments of the aforementioned system aspect and embodiments, the cathode is a gas-diffusion cathode configured to react hydrochloric acid and oxygen to form water.

In some embodiments of the aforementioned system aspect and embodiments, the anode is configured to not form a gas.

In some embodiments of the aforementioned aspect and embodiments, the system further comprises a precipitator configured to contact the cathode electrolyte with divalent cations to form a carbonate and/or bicarbonate product.

In some embodiments of the aforementioned aspect and embodiments, the metal ion is copper. In some embodiments of the aforementioned aspect and embodiments, the unsaturated hydrocarbon is ethylene. In some embodiments of the aforementioned aspect and embodiments, the one or more organic compounds are selected from ethylene dichloride, chloroethanol, dichloroacetaldehyde, trichloroacetaldehyde, and combinations thereof.

In one aspect, there is provided a method, comprising: contacting an anode with an anode electrolyte wherein the anode electrolyte comprises metal ion; oxidizing the metal ion from a lower oxidation state to a higher oxidation state at the anode; and reacting an unsaturated or saturated hydrocarbon with the anode electrolyte comprising the metal ion in the higher oxidation state in an aqueous medium, to form one or more organic compounds comprising halogenated or sulfonated hydrocarbon and the metal ion in the lower oxidation state, wherein the reacting is under one or more of reaction conditions favorable to produce the halogenated or sulfonated hydrocarbon with more than about 0.5 STY. In some embodiments of the aforementioned aspect, the one or more of reaction conditions comprise temperature between 100-200° C., pressure of between 200-300 psig, or combination thereof. In some embodiments of the aforementioned aspect and embodiment, the one or more of reaction conditions comprise metal ion concentration, ratio of metal ion in the lower oxidation state to the metal ion in the higher oxidation state in the anode electrolyte, partial pressure of the unsaturated or saturated hydrocarbon, partial pressure of water vapor, flow rate of the anode electrolyte, flow rate of the unsaturated or saturated hydrocarbon, density of the anode electrolyte, viscosity of the anode electrolyte, reaction time, or combinations thereof. In some embodiments of the aforementioned aspect and embodiments, the metal ion concentration is between about 1-8M, the ratio is between about 1:8-1:5, the flow rate of the anode electrolyte is between about 150-300 kg/h, or combinations thereof. In some embodiments of the aforementioned aspect and embodiments, the one or more of reaction conditions are favorable to produce the halogenated hydrocarbon with more than about 80% selectivity. In some embodiments of the aforementioned aspect and embodiments, the unsaturated hydrocarbon is ethylene, the halogenated hydrocarbon is ethylene dichloride, the metal ion is copper chloride, or combinations thereof.

In another aspect, there is provided a method comprising contacting an anode with an anode electrolyte wherein the anode electrolyte comprises metal ion; oxidizing the metal ion from a lower oxidation state to a higher oxidation state at the anode; reacting an unsaturated or saturated hydrocarbon with the anode electrolyte comprising the metal ion in the higher oxidation state in an aqueous medium, to form one or more organic compounds comprising halogenated or sulfonated hydrocarbon and the metal ion in the lower oxidation state; and separating and purifying the one or more organic compounds comprising halogenated or sulfonated hydrocarbon from the aqueous medium. In some embodiments of the aforementioned aspect, the separating and purifying comprises reaction separation process, compression-cooling process, liquid-liquid separation process, vapor-liquid separation process, scrubbing process, purification subprocess, adsorption, and combinations thereof. In some embodiments of the aforementioned aspect and embodiments, the reacting step includes reaction separation.

In some embodiments of the aforementioned aspect and embodiments, the reaction separation comprises reactive distillation, reactive extraction, or combination thereof.

In some embodiments of the aforementioned aspect and embodiments, the liquid-liquid separation process comprises decantation, extraction, or combination thereof; the vapor-liquid separation process comprises flash distillation, distillation, or combination thereof; the purification subprocess process comprises decantation, adsorption, distillation, or combinations thereof; and/or the scrubber comprises treatment with an alkali.

In some embodiments of the aforementioned aspect and embodiments, the separation and purification produces the halogenated hydrocarbon with more than about 90% yield and/or more than about 90% purity. In some embodiments of the aforementioned aspect and embodiments, the separation and purification produces the aqueous medium comprising the metal ion and less than about 1% or no organic compound.

In some embodiments of the aforementioned aspect and embodiments, the method further comprises one or more of heat exchanges between the anode electrolyte, the unsaturated or saturated hydrocarbon, the aqueous medium comprising the metal ion in the lower and higher oxidation state, steam, water, or combinations thereof. In some embodiments of the aforementioned aspect and embodiments, the unsaturated hydrocarbon is ethylene and the halogenated hydrocarbon is EDC. In some embodiments of the aforementioned aspect and embodiments, the metal ion is copper. In some embodiments of the aforementioned aspect and embodiments, the reaction produces EDC with about or more than 0.1 STY and more than 95% selectivity.

In some embodiments of the aforementioned aspect and embodiments, the method further comprises forming an alkali, water, or hydrogen gas at the cathode. In some embodiments of the aforementioned aspect and embodiments, the method further comprises forming an alkali at the cathode. In some embodiments of the aforementioned aspect, the method further comprises forming hydrogen gas at the cathode. In some embodiments of the aforementioned aspect, the method further comprises forming water at the cathode. In some embodiments of the aforementioned aspect, the cathode is an oxygen depolarizing cathode that reduces oxygen and water to hydroxide ions. In some embodiments of the aforementioned aspect, the cathode is a hydrogen gas producing cathode that reduces water to hydrogen gas and hydroxide ions. In some embodiments of the aforementioned aspect, the cathode is a hydrogen gas producing cathode that reduces hydrochloric acid to hydrogen gas. In some embodiments of the aforementioned aspect, the cathode is an oxygen depolarizing cathode that reacts with hydrochloric acid and oxygen gas to form water.

In some embodiments of the aforementioned aspect and embodiments, the aqueous medium that is recirculated back to the anode electrolyte comprises less than 10000 ppm, or less than 1000 ppm or less than 800 ppm or less than 500 ppm or less than 250 ppm or less than 100 ppm or less than 50 ppm or less than 10 ppm or less than 1 ppm of the organic compound(s). In some embodiments of the aforementioned aspect and embodiments, the aqueous medium comprises between 5-95 wt % water, or between 5-90 wt % water, or between 5-99 wt % water.

In some embodiments of the aforementioned aspect and embodiments, the metal ion includes, but not limited to, iron, chromium, copper, tin, silver, cobalt, uranium, lead, mercury, vanadium, bismuth, titanium, ruthenium, osmium, europium, zinc, cadmium, gold, nickel, palladium, platinum, rhodium, iridium, manganese, technetium, rhenium, molybdenum, tungsten, niobium, tantalum, zirconium, hafnium, and combination thereof. In some embodiments, the metal ion includes, but not limited to, iron, chromium, copper, and tin. In some embodiments, the metal ion is copper. In some embodiments, the lower oxidation state of the metal ion is 1+, 2+, 3+, 4+, or 5+. In some embodiments, the higher oxidation state of the metal ion is 2+, 3+, 4+, 5+, or 6+. In some embodiments, the metal ion is copper that is converted from $Cu^+$ to $Cu^{2+}$, the metal ion is iron that is converted from $Fe^{2+}$ to $Fe^{3+}$, the metal ion is tin that is converted from $Sn^{2+}$ to $Sn^{4+}$, the metal ion is chromium that is converted from $Cr^{2+}$ to $Cr^{3+}$, the metal ion is platinum that is converted from $Pt^{2+}$ to $Pt^{4+}$, or combination thereof.

In some embodiments of the aforementioned aspect and embodiments, no gas is used or formed at the anode. In some embodiments of the aforementioned aspect and embodiments, the method further comprises adding a ligand to the anode electrolyte wherein the ligand interacts with the metal ion. In some embodiments of the aforementioned aspect and embodiments, the method further comprises reacting an unsaturated hydrocarbon or a saturated hydrocarbon with the anode electrolyte comprising the metal ion in the higher oxidation state and the ligand, wherein the reaction is in an aqueous medium. In some embodiments of the aforementioned aspect and embodiments, the reaction of the unsaturated hydrocarbon or the saturated hydrocarbon with the anode electrolyte comprising the metal ion in the higher oxidation state is halogenation or sulfonation using the metal halide or the metal sulfate in the higher oxidation state resulting in a halohydrocarbon or a sulfohydrocarbon, respectively, and the metal halide or the metal sulfate in the lower oxidation state. In some embodiments, the metal halide or the metal sulfate in the lower oxidation state is re-circulated back to the anode electrolyte.

In some embodiments of the aforementioned aspect and embodiments, the anode electrolyte comprising the metal ion in the higher oxidation state further comprises the metal ion in the lower oxidation state. In some embodiments of the aforementioned aspect and embodiments, the unsaturated hydrocarbon is ethylene, propylene, or butylene and the halogenated hydrocarbon is ethylene dichloride, propylene dichloride or 1,4-dichlorobutane, respectively. In some embodiments, the method further comprises forming vinyl chloride monomer from the ethylene dichloride and forming poly(vinyl chloride) from the vinyl chloride monomer. In some embodiments of the aforementioned aspect and embodiments, the saturated hydrocarbon is methane, ethane, or propane. In some embodiments of the aforementioned aspect and embodiments, the one or more organic compounds comprise ethylene dichloride, chloroethanol, dichloroacetaldehyde, trichloroacetaldehyde, or combinations thereof. In some embodiments of the aforementioned aspect and embodiments, the method further comprises contacting a diffusion enhancing anode such as, but not limited to, a porous anode with the anode electrolyte. The diffusion enhancing anode such as, but not limited to, the porous anode has been described herein.

BRIEF DESCRIPTION OF THE DRAWINGS

The novel features of the invention are set forth with particularity in the appended claims. A better understanding of the features and advantages of the present invention may be obtained by reference to the following detailed description that sets forth illustrative embodiments, in which the principles of the invention are utilized, and the accompanying drawings of which:

FIG. 4A is an illustration of some embodiments provided herein.

FIG. 4B is an illustration of some embodiments provided herein.

DETAILED DESCRIPTION

Figure 1A:
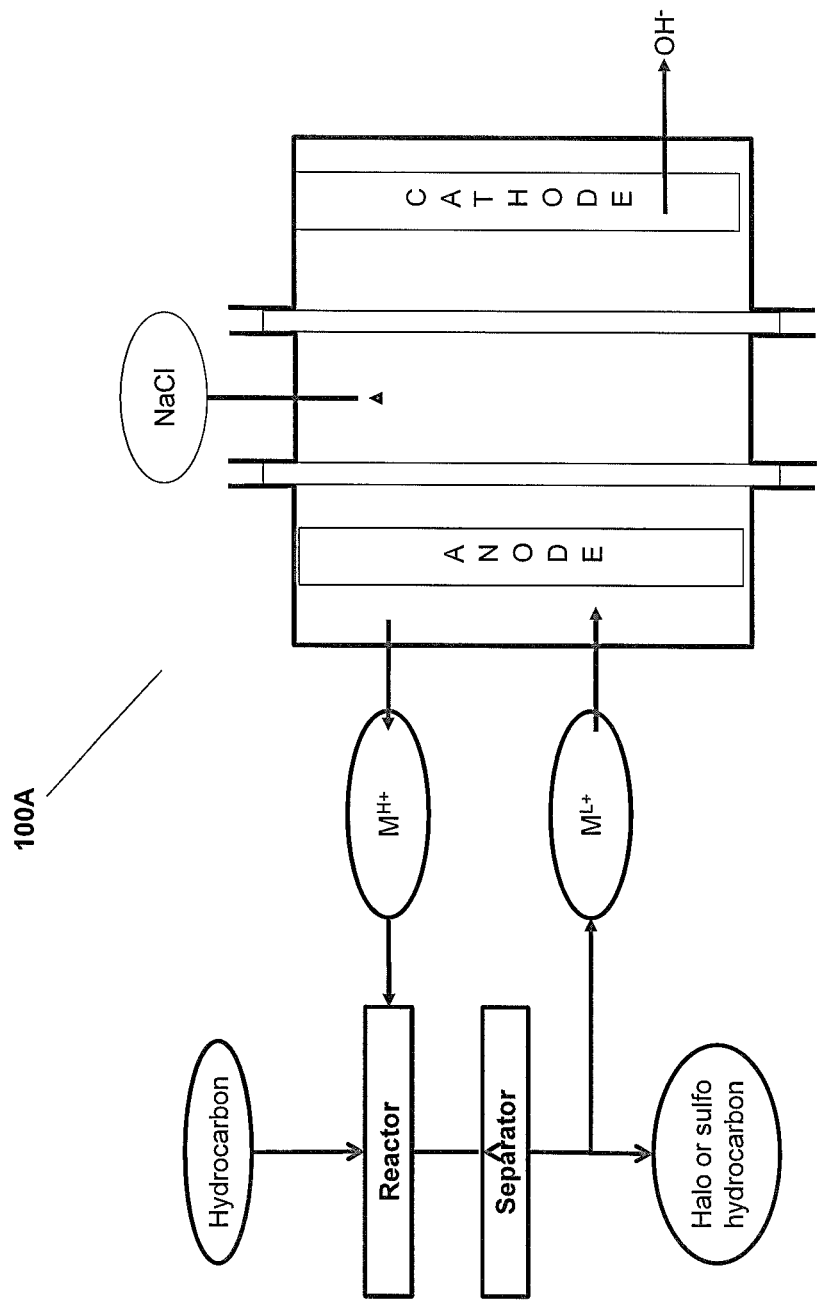
FIG. 1A is an illustration of some embodiments provided herein.

Disclosed herein are systems and methods that relate to the oxidation of a metal ion by the anode in the anode chamber where the metal ion is oxidized from the lower oxidation state to a higher oxidation state.

As can be appreciated by one ordinarily skilled in the art, the present electrochemical system and method can be configured with an alternative, equivalent salt solution, e.g., a potassium chloride solution or sodium chloride solution or a magnesium chloride solution or sodium sulfate solution or ammonium chloride solution, to produce an equivalent alkaline solution, e.g., potassium hydroxide or sodium hydroxide or magnesium hydroxide in the cathode electrolyte. Accordingly, to the extent that such equivalents are based on or suggested by the present system and method, these equivalents are within the scope of the application.

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Certain ranges that are presented herein with numerical values may be construed as "about" numericals. The "about" is to provide literal support for the exact number that it precedes, as well as a number that is near to or approximately the number that the term precedes. In determining whether a number is near to or approximately a specifically recited number, the near or approximating unrequited number may be a number, which, in the context in which it is presented, provides the substantial equivalent of the specifically recited number.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a," "an," and "the" include plural references unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

Compositions, Methods, and Systems

There are provided methods and systems that relate to the oxidation of metal ions from a lower oxidation state to a higher oxidation state in the anode chamber of the electrochemical cell; use of the metal ion in the higher oxidation state for the generation of halohydrocarbons or sulfohydrocarbons from hydrocarbons; separation/purification of the halohydrocarbons or sulfohydrocarbons from the metal ion solution; and recycling of the metal ion solution back to the electrochemical cell. In one aspect, the electrochemical cells described herein provide an efficient and low voltage system where the metal compound such as metal halide, e.g., metal chloride or a metal sulfate with the higher oxidation state produced by the anode can be used for purposes, such as, but not limited to, generation of halohydrocarbons or sulfohydrocarbons from hydrocarbons in high yield and selectivity.

In some embodiments, there are provided methods that include contacting an anode with a metal ion in an anode electrolyte in an anode chamber; oxidizing the metal ion from a lower oxidation state to a higher oxidation state at the anode; contacting a cathode with a cathode electrolyte in a cathode chamber; forming an alkali, water, and/or hydrogen gas at the cathode; contacting the anode electrolyte comprising metal ion in the higher oxidation state with an unsaturated and/or saturated hydrocarbon to form halogenated or sulfonated hydrocarbon and form the metal ion solution comprising metal ion in the lower oxidation state; and separating and/or purifying the halogenated or sulfonated hydrocarbon from the metal ions solution. In some embodiments, the separated metal ion solution comprising metal ion in the lower oxidation state and optionally comprising metal ion in the higher oxidation state are recirculated back to the anode electrolyte.

In some embodiments, there are provided systems that include an anode chamber comprising an anode in contact with a metal ion in an anode electrolyte, wherein the anode is configured to convert the metal ion from a lower oxidation state to a higher oxidation state; and a cathode chamber comprising a cathode in contact with a cathode electrolyte wherein the cathode is configured to form an alkali, water, and/or hydrogen gas in the cathode electrolyte; a reactor operably connected to the anode chamber and configured to contact the anode electrolyte comprising metal ion in the higher oxidation state with an unsaturated and/or saturated hydrocarbon to form halogenated or sulfonated hydrocarbon and form the metal ion solution comprising metal ion in the lower oxidation state; and a separator to separate and/or purify the halogenated or sulfonated hydrocarbon from the metal ions solution. In some embodiments, the system further comprises a recirculation system to recirculate the separated metal ion solution comprising metal ion in the lower oxidation state and optionally comprising metal ion in the higher oxidation state, back to the anode electrolyte.

An illustrative example of an electrochemical system producing anode electrolyte with metal ion in the higher oxidation state integrated with a reactor system for generation of halohydrocarbon or sulfohydrocarbon from hydrocarbon and metal ion in the higher oxidation state, and further the reactor system integrated with the separator system to separate the halohydrocarbon or sulfohydrocarbon from the metal ion solution, is as illustrated in FIG. 1A. The electrochemical system 100A of FIG. 1A includes an anode and a cathode separated by anion exchange membrane and cation exchange membrane creating a third chamber containing a third electrolyte, NaCl. The anode chamber includes the anode and an anode electrolyte in contact with the anode. The cathode chamber includes the cathode and a cathode electrolyte in contact with the cathode. The metal ion is oxidized in the anode chamber from the lower oxidation state $M^{L+}$ to the higher oxidation state $M^{H+}$ which metal in the higher oxidation state is then used for reactions in a reactor, such as reaction with hydrocarbon, such as, unsaturated or saturated hydrocarbon to produce halohydrocarbon or sulfohydrocarbon. The metal ion in the higher oxidation state is consequently reduced to metal ion in the lower oxidation state. The metal ion solution is separated from the halohydrocarbon or sulfohydrocarbon (organics) in a separator before the metal ion solution is recirculated back to the anode electrolyte of the electrochemical system. It is to be understood that the metal ion solution going into the anode electrolyte and the metal ion solution coming out of the anode electrolyte may contain a mix of the metal ion in the lower oxidation state and the higher oxidation state except that the metal ion solution coming out of the anode electrolyte has higher amount of metal ion in the higher oxidation state than the metal ion solution going into the anode electrolyte.

The products formed by such reactions are described herein. It is to be understood that the system 100A of FIG. 1A is for illustration purposes only and metal ions with different oxidations states (e.g., chromium, tin etc.); other electrochemical systems described herein; the third electrolyte other than sodium chloride such as sodium sulfate; and other cathodes producing water and/or hydrogen gas, are variations that are equally applicable to this system. It is also to be understood that the reactor may be a combination of one or more reactors and the separator may be a combination of one or more separators or separation units. The reactors and the separators have been described herein in detail. In some embodiments, the metal compound produced by the anode chamber may be used as is or may be purified before reacting with unsaturated hydrocarbon or saturated hydrocarbon for the generation of halohydrocarbon or sulfohydrocarbon. For example, in some embodiments, the metal compound/solution in the higher oxidation state is treated with the ethylene gas to form a halohydrocarbon product, such as ethylene dichloride (EDC). The ethylene dichloride may also be known as 1,2-dichloroethane, dichloroethane, 1,2-ethylene dichloride, glycol dichloride, freon 150, etc. In some embodiments, the electrochemical system of the invention is integrated with vinyl chloride monomer (VCM) production facility or polyvinylchloride (PVC) production facility such that the EDC formed via the systems and methods of the invention is used in VCM and/or PVC production.

In the systems and methods provided herein the metal ion solutions may be separated and/or purified before and after the reaction in the reactor. Similarly, the products made in the reactor may also be subjected to organic separation and/or purification before their commercial use. In the methods and systems provided herein, the separation and/or purification may include one or more of the separation and purification of the organic compounds from the metal ion solution; the separation and purification of the organic compounds from each other; and separation and purification of the metal ion in the lower oxidation state from the metal ion in the higher oxidation state, to improve the overall yield of the organic product, improve selectivity of the organic product, improve purity of the organic product, improve efficiency of the systems, improve ease of use of the solutions in the overall process, improve reuse of the metal solution in the electrochemical and reaction process, and to improve the overall economics of the process.

Provided in detail below are the methods and systems including, but not limited to, the metal ions; ligands; the electrochemical cell, anode, cathode, and membranes; the reactor system integrated with the electrochemical system; and the separator system for the separation and optional purification of the organic compounds from the metal ion solution, the separation and optional purification of the organic compounds from side products, and the separation and optional purification of the metal compound in lower oxidation state mixed with metal compound in the higher oxidation state. It is to be understood that one or more of the sections provided below can be combined in the methods and system provided herein. It is also to be understood that various embodiments within each section can be combined with one or more of embodiments described in the other sections, in the methods and systems provided herein.

Electrochemical Compositions, Methods, and Systems

Electrochemical Cell

The systems and methods of the invention provide an electrochemical cell that produces various products, such as, but not limited to, metal salts formed at the anode, the metal salts used to form various other chemicals, alkali formed at the cathode, alkali used to form various other products, and/or hydrogen gas formed at the cathode. All of such products have been defined herein and may be called green chemicals since such chemicals are formed using the electrochemical cell that runs at low voltage or energy and high efficiency. The low voltage or less energy intensive process described herein would lead to lesser emission of carbon dioxide as compared to conventional methods of making similar chemicals or products. In some embodiments, the chemicals or products are formed by the capture of carbon dioxide from flue gas in the alkali generated at the cathode, such as, but not limited to, carbonate and bicarbonate products. Such carbonate and bicarbonate products are green chemicals as they reduce the pollution and provide cleaner environment.

The electrochemical cell provided herein may be any electrochemical cell where the metal ion in the lower oxidation state is converted to the metal ion in the higher oxidation state in the anode chamber. In such electrochemical cells, cathode reaction may be any reaction that does or does not form an alkali in the cathode chamber. Such cathode consumes electrons and carries out any reaction including, but not limited to, the reaction of water to form hydroxide ions and hydrogen gas or reaction of oxygen gas and water to form hydroxide ions or reduction of protons from an acid such as hydrochloric acid to form hydrogen gas or reaction of protons from hydrochloric acid and oxygen gas to form water.

In some embodiments, the electrochemical cells may include production of alkali in the cathode chamber of the cell. The alkali generated in the cathode chamber may be used as is for commercial purposes or may be treated with divalent cations to form divalent cation containing carbonates/bicarbonates. In some embodiments, the alkali generated in the cathode chamber may be used to sequester or capture carbon dioxide. The carbon dioxide may be present in flue gas emitted by various industrial plants. The carbon dioxide may be sequestered in the form of carbonate and/or bicarbonate products. Therefore, both the anode electrolyte as well as the cathode electrolyte can be used for generating products that may be used for commercial purposes thereby providing a more economical, efficient, and less energy intensive process.

The electrochemical systems and methods described herein provide one or more advantages over conventional electrochemical systems known in the art, including, but not limited to, no requirement of gas diffusion anode; higher cell efficiency; lower voltages; platinum free anode; sequestration of carbon dioxide; green and environment friendly chemicals; and/or formation of various commercially viable products.

Some embodiments of the electrochemical cells used in the methods and systems provided herein, are as illustrated in the figures and as described herein. It is to be understood that the figures are for illustration purposes only and that variations in the reagents and set up are well within the scope of the invention. All the electrochemical methods and systems described herein do not produce a gas at the anode such as chlorine gas, as is found in the chlor-alkali systems. All the systems and methods that relate to the halogenation or sulfonation of the unsaturated or saturated hydrocarbon, do not use oxygen gas in the catalytic reactor.

Figure 1B:
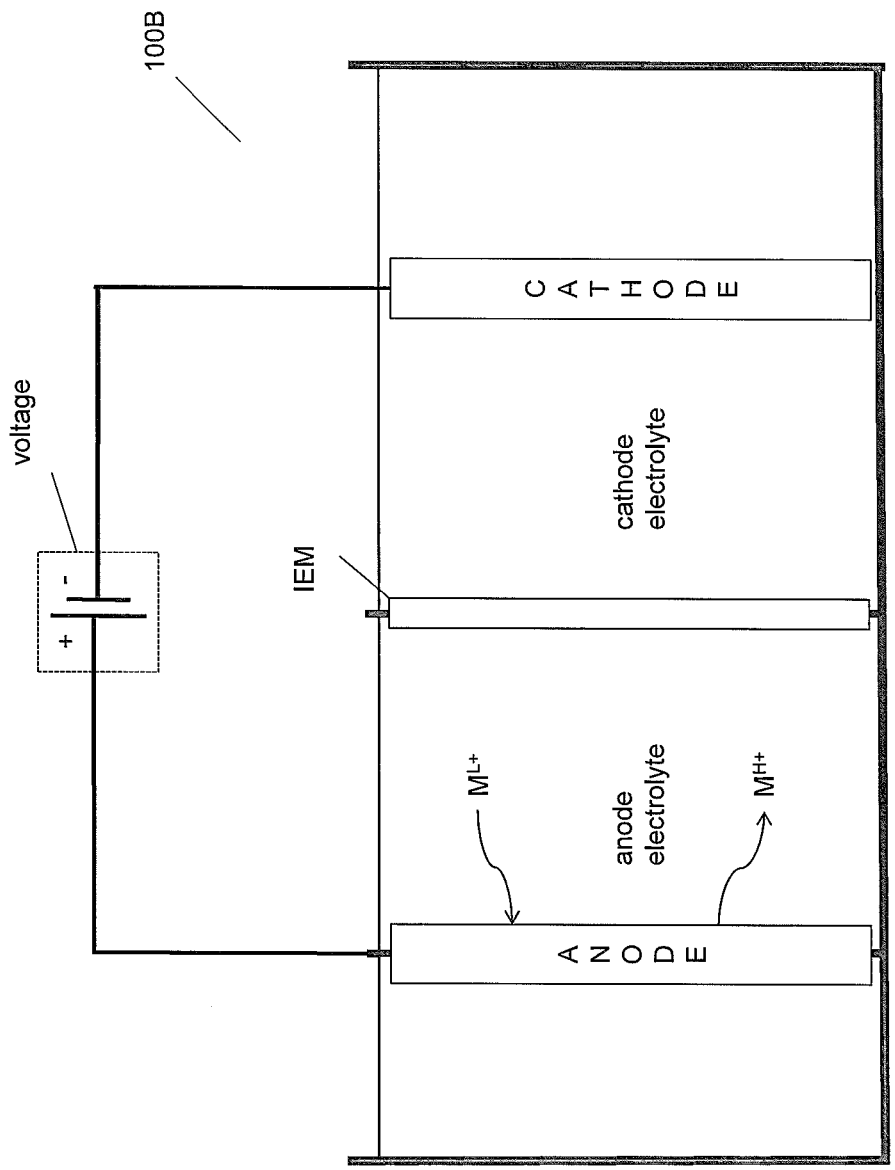
FIG. 1B is an illustration of some embodiments provided herein.

As illustrated in FIG. 1B, the electrochemical system 100B includes an anode chamber with an anode in contact with an anode electrolyte where the anode electrolyte contains metal ions in the lower oxidation state (represented as $M^{L+}$) which are converted by the anode to metal ions in the higher oxidation state (represented as $M^{H+}$). The metal ion may be in the form of a sulfate, chloride, bromide, or iodide.

As used herein "lower oxidation state" represented as L+ in $M^{L+}$ includes the lower oxidation state of the metal. For example, lower oxidation state of the metal ion may be 1+, 2+, 3+, 4+, or 5+. As used herein "higher oxidation state" represented as H+ in $M^{H+}$ includes the higher oxidation state of the metal. For example, higher oxidation state of the metal ion may be 2+, 3+, 4+, 5+, or 6+.

The electron(s) generated at the anode are used to drive the reaction at the cathode. The cathode reaction may be any reaction known in the art. The anode chamber and the cathode chamber may be separated by an ion exchange membrane (IEM) that may allow the passage of ions, such as, but not limited to, sodium ions in some embodiments to the cathode electrolyte if the anode electrolyte is sodium chloride, sodium bromide, sodium iodide, sodium sulfate, or ammonium ions if the anode electrolyte is ammonium chloride etc. or an equivalent solution containing metal halide. Some reactions that may occur at the cathode include, but not limited to, reaction of water to form hydroxide ions and hydrogen gas; reaction of oxygen gas and water to form hydroxide ions; reduction of HCl to form hydrogen gas; or reaction of HCl and oxygen gas to form water.

In some embodiments, the electrochemical system includes a cathode chamber with a cathode in contact with the cathode electrolyte that forms hydroxide ions in the cathode electrolyte. In some embodiments, the ion exchange membrane allows the passage of anions, such as, but not limited to, chloride ions, bromide ions, iodide ions, or sulfate ions to the anode electrolyte if the cathode electrolyte is e.g., sodium chloride, sodium bromide, sodium iodide, or sodium sulfate or an equivalent solution. The sodium ions combine with hydroxide ions in the cathode electrolyte to form sodium hydroxide. The anions combine with metal ions to form metal halide or metal sulfate. It is to be understood that other cathodes such as, cathode reducing HCl to form hydrogen gas or cathode reacting both HCl and oxygen gas to form water, are equally applicable to the systems. Such cathodes have been described herein.

In some embodiments, the electrochemical systems of the invention include one or more ion exchange membranes. In some embodiments, the ion exchange membrane is a cation exchange membrane (CEM), an anion exchange membrane (AEM); or combination thereof.

Figure 2:
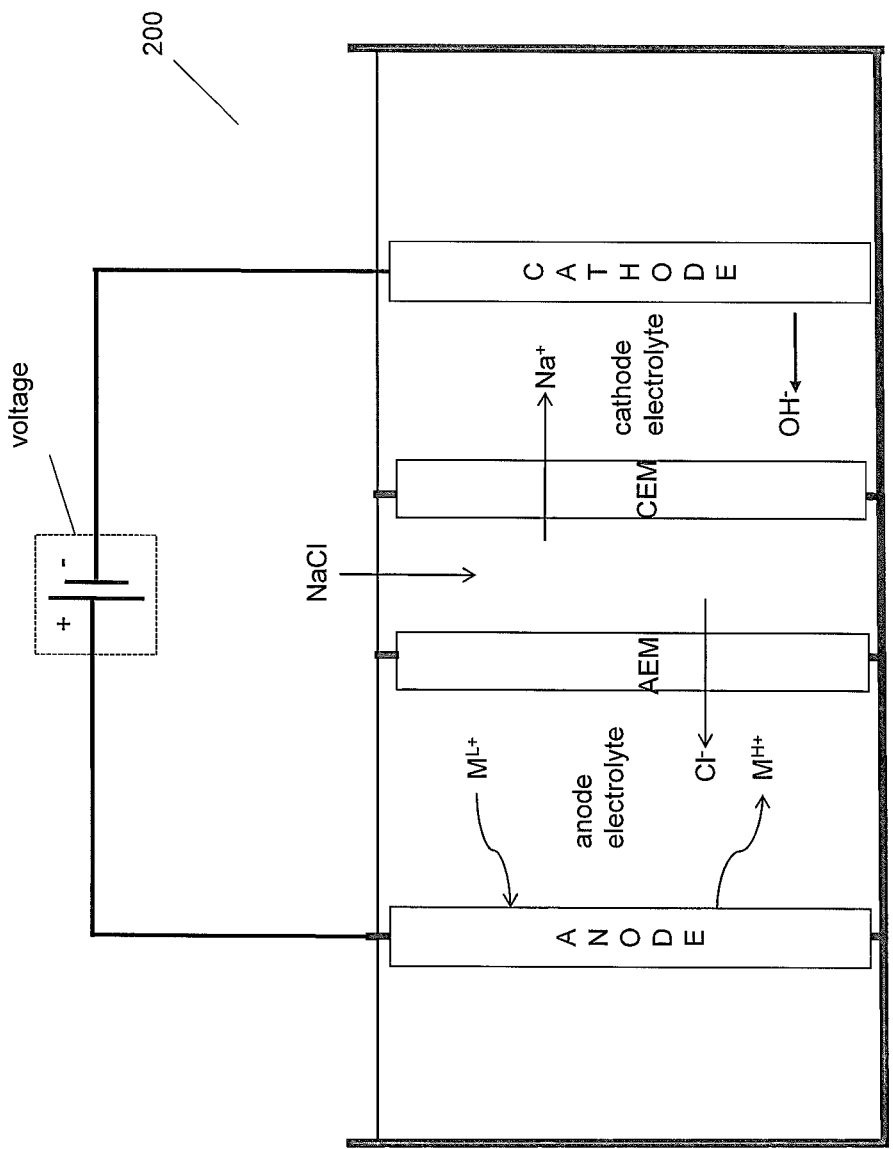
FIG. 2 is an illustration of some embodiments provided herein.

As illustrated in FIG. 2 (or also illustrated in FIG. 1A), the electrochemical system 200 includes a cathode in contact with a cathode electrolyte and an anode in contact with an anode electrolyte. The cathode forms hydroxide ions in the cathode electrolyte and the anode converts metal ions from lower oxidation state ($M^{L+}$) to higher oxidation state ($M^{H+}$). The anode and the cathode are separated by an anion exchange membrane (AEM) and a cation exchange membrane (CEM). A third electrolyte (e.g., sodium chloride, sodium bromide, sodium iodide, sodium sulfate, ammonium chloride, or combinations thereof or an equivalent solution) is disposed between the AEM and the CEM. The sodium ions from the third electrolyte pass through CEM to form sodium hydroxide in the cathode chamber and the halide anions such as, chloride, bromide or iodide ions, or sulfate anions, from the third electrolyte pass through the AEM to form a solution for metal halide or metal sulfate in the anode chamber. The metal halide or metal sulfate formed in the anode electrolyte is then delivered to a reactor for reaction with an unsaturated or saturated hydrocarbon to generate halohydrocarbons or sulfohydrocarbons, respectively. The third electrolyte, after the transfer of the ions, can be withdrawn from the middle chamber as depleted ion solution. For example, in some embodiments when the third electrolyte is sodium chloride solution, then after the transfer of the sodium ions to the cathode electrolyte and transfer of chloride ions to the anode electrolyte, the depleted sodium chloride solution may be withdrawn from the middle chamber. The depleted salt solution may be used for commercial purposes or may be transferred to the anode and/or cathode chamber as an electrolyte or concentrated for re-use as the third electrolyte. In some embodiments, the depleted salt solution may be useful for preparing desalinated water. It is to be understood that the hydroxide forming cathode, as illustrated in FIG. 2 is for illustration purposes only and other cathodes such as, cathode reducing HCl to form hydrogen gas or cathode reacting both HCl and oxygen gas to form water, are equally applicable to the systems and have been described further herein.

Figure 3A:
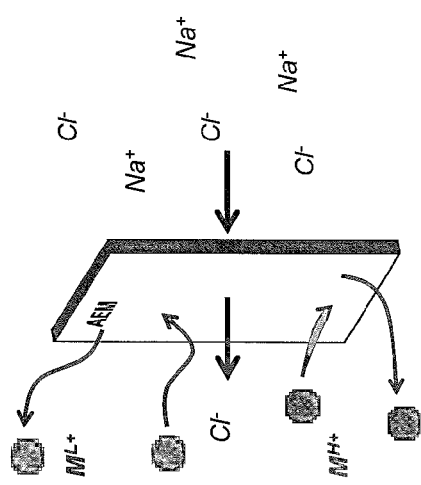
FIG. 3A is an illustration of some embodiments provided herein.
Figure 3B:
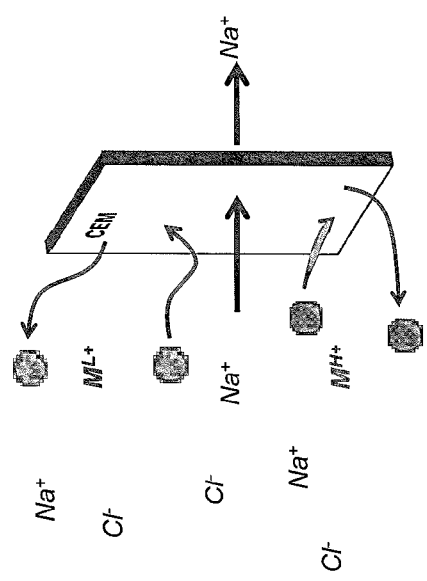
FIG. 3B is an illustration of some embodiments provided herein.

In some embodiments, the ion exchange membrane described herein, is an anion exchange membrane, as illustrated in FIG. 3A. In such embodiments, the cathode electrolyte (or the third electrolyte in the third chamber) may be a sodium halide, sodium sulfate or an equivalent solution and the AEM is such that it allows the passage of anions to the anode electrolyte but prevents the passage of metal ions from the anode electrolyte to the cathode electrolyte (or to the third electrolyte in the third chamber). In some embodiments, the ion exchange membrane described herein, is a cation exchange membrane, as illustrated in FIG. 3B. In such embodiments, the anode electrolyte (or the third electrolyte in the third chamber) may be a sodium halide, sodium sulfate or an equivalent solution containing the metal halide solution or an equivalent solution and the CEM is such that it allows the passage of sodium cations to the cathode electrolyte but prevents the passage of metal ions from the anode electrolyte to the cathode electrolyte. In some embodiments, both the AEM and CEM may be joined together in the electrochemical system. In some embodiments, the use of one ion exchange membrane instead of two ion exchange membranes may reduce the resistance offered by multiple IEMs and may facilitate lower voltages for running the electrochemical reaction. Some examples of the suitable anion exchange membranes are provided further herein.

The electrochemical cells in the methods and systems provided herein are membrane electrolyzers. The electrochemical cell may be a single cell or may be a stack of cells connected in series or in parallel. The electrochemical cell may be a stack of 5 or 6 or 50 or 100 or more electrolyzers connected in series or in parallel. Each cell comprises an anode, a cathode, and an ion exchange membrane, as illustrated in FIG. 1A, 1B or FIG. 2.

In some embodiments, the electrolyzers provided herein are monopolar electrolyzers. In the monopolar electrolyzers, the electrodes may be connected in parallel as illustrated in FIG. 4A where all anodes and all cathodes are connected in parallel. In such monopolar electrolyzers, the operation takes place at high amperage and low voltage. In some embodiments, the electrolyzers provided herein are bipolar electrolyzers. In the bipolar electrolyzers, the electrodes may be connected in series as illustrated in FIG. 4B where all anodes and all cathodes are connected in series. In such bipolar electrolyzers, the operation takes place at low amperage and high voltage. In some embodiments, the electrolyzers are a combination of monopolar and bipolar electrolyzers and may be called hybrid electrolyzers (not shown in the figures). It is to be understood that FIGS. 4A and 4B show a stack of three cells for illustration purposes only and the stack may be a combination of two or more electrolyzers.

In some embodiments of the bipolar electrolyzers as described above, the cells are stacked serially constituting the overall electrolyzer and are electrically connected in two ways. In bipolar electrolyzers, a single plate, called bipolar plate, may serve as base plate for both the cathode and anode. The electrolyte solution may be hydraulically connected through common manifolds and collectors internal to the cell stack. The stack may be compressed externally to seal all frames and plates against each other which is typically referred to as a filter press design. In some embodiments, the bipolar electrolyzer may also be designed as a series of cells, individually sealed, and electrically connected through back-to-back contact, typically known as a single element design. The single element design may also be connected in parallel in which case it would be a monopolar electrolyzer.

In some embodiments, the cell size may be denoted by the active area dimensions. In some embodiments, the active area of the electrolyzers used herein may range from 0.5-1.5 meters tall and 0.4-3 meters wide. The individual compartment thicknesses may range from 0.5 mm-50 mm.

The electrolyzers used in the methods and systems provided herein, are made from corrosion resistant materials. Variety of materials were tested (as described in Example 4) in metal solutions such as copper and at varying temperatures, for corrosion testing. The materials include, but not limited to, polyvinylidene fluoride, viton, polyether ether ketone, fluorinated ethylene propylene, fiber-reinforced plastic, halar, ultem (PEI), perfluoroalkoxy, tefzel, tyvar, fibre-reinforced plastic-coated with derakane 441-400 resin, graphite, akot, tantalum, hastelloy C2000, titanium Gr.7, titanium Gr.2, or combinations thereof. In some embodiments, these materials can be used for making the electrochemical cells and/or it components including, but not limited to, tank materials, piping, heat exchangers, pumps, reactors, cell housings, cell frames, electrodes, instrumentation, valves, and all other balance of plant materials. In some embodiments, the material used for making the electrochemical cell and its components include, but not limited to, titanium Gr.2.

Metal

The "metal ion" or "metal" as used herein, includes any metal ion capable of being converted from lower oxidation state to higher oxidation state. Examples of metal ions include, but not limited to, iron, chromium, copper, tin, silver, cobalt, uranium, lead, mercury, vanadium, bismuth, titanium, ruthenium, osmium, europium, zinc, cadmium, gold, nickel, palladium, platinum, rhodium, iridium, manganese, technetium, rhenium, molybdenum, tungsten, niobium, tantalum, zirconium, hafnium, and combination thereof. In some embodiments, the metal ions include, but not limited to, iron, copper, tin, chromium, or combination thereof. In some embodiments, the metal ion is copper. In some embodiments, the metal ion is tin. In some embodiments, the metal ion is iron. In some embodiments, the metal ion is chromium. In some embodiments, the metal ion is platinum. The "oxidation state" as used herein, includes degree of oxidation of an atom in a substance. For example, in some embodiments, the oxidation state is the net charge on the ion. Some examples of the reaction of the metal ions at the anode are as shown in Table I below (SHE is standard hydrogen electrode). The theoretical values of the anode potential are also shown. It is to be understood that some variation from these voltages may occur depending on conditions, pH, concentrations of the electrolytes, etc and such variations are well within the scope of the invention.

TABLE I

| Anode Reaction | Anode Potential (V vs. SHE) |
|---|---|
| $Ag^+ \rightarrow Ag^{2+} + e^-$ | −1.98 |
| $Co^{2+} \rightarrow Co^{3+} + e^-$ | −1.82 |
| $Pb^{2+} \rightarrow Pb^{4+} + 2e^-$ | −1.69 |

TABLE I-continued

| Anode Reaction | Anode Potential (V vs. SHE) |
|---|---|
| $Ce^{3+} \rightarrow Ce^{4+} + e^-$ | −1.44 |
| $2Cr^{3+} + 7H_2O \rightarrow Cr_2O_7^{2-} + 14H^+ + 6e^-$ | −1.33 |
| $Tl^+ \rightarrow Tl^{3+} + 2e^-$ | −1.25 |
| $Hg_2^{2+} \rightarrow 2Hg^{2+} + 2e^-$ | −0.91 |
| $Fe^{2+} \rightarrow Fe^{3+} + e^-$ | −0.77 |
| $V^{3+} + H_2O \rightarrow VO^{2+} + 2H^+ + e^-$ | −0.34 |
| $U^{4+} + 2H_2O \rightarrow UO_2^+ + 4H^- + e^-$ | −0.27 |
| $Bi^+ \rightarrow Bi^{3+} + 2e^-$ | −0.20 |
| $Ti^{3+} + H_2O \rightarrow TiO^{2+} + 2H^+ + e^-$ | −0.19 |
| $Cu^+ \rightarrow Cu^{2+} + e^-$ | −0.16 |
| $UO_2^+ \rightarrow UO_2^{2+} + e^-$ | −0.16 |
| $Sn^{2+} \rightarrow Sn^{4+} + 2e^-$ | −0.15 |
| $Ru(NH_3)_6^{2+} \rightarrow Ru(NH_3)_6^{3+} + e^-$ | −0.10 |
| $V^{2+} \rightarrow V^{3+} + e^-$ | +0.26 |
| $Eu^{2+} \rightarrow Eu^{3+} + e^-$ | +0.35 |
| $Cr^{2+} \rightarrow Cr^{3+} + e^-$ | +0.42 |
| $U^{3+} \rightarrow U^{4+} + e^-$ | +0.52 |

The metal ion may be present as a compound of the metal or an alloy of the metal or combination thereof. In some embodiments, the anion attached to the metal is same as the anion of the electrolyte. For example, for sodium or potassium chloride used as an electrolyte, a metal chloride, such as, but not limited to, iron chloride, copper chloride, tin chloride, chromium chloride etc. is used as the metal compound. For example, for sodium or potassium sulfate used as an electrolyte, a metal sulfate, such as, but not limited to, iron sulfate, copper sulfate, tin sulfate, chromium sulfate etc. is used as the metal compound. For example, for sodium or potassium bromide used as an electrolyte, a metal bromide, such as, but not limited to, iron bromide, copper bromide, tin bromide etc. is used as the metal compound.

In some embodiments, the anion of the electrolyte may be partially or fully different from the anion of the metal. For example, in some embodiments, the anion of the electrolyte may be a sulfate whereas the anion of the metal may be a chloride. In such embodiments, it may be desirable to have less concentration of the chloride ions in the electrochemical cell. For example, in some embodiments, the higher concentration of chloride ions in the anode electrolyte, due to chloride of the electrolyte and the chloride of the metal, may result in undesirable ionic species in the anode electrolyte. This may be avoided by utilizing an electrolyte that contains ions other than chloride. In some embodiments, the anode electrolyte may be a combination of ions similar to the metal anion and anions different from the metal ion. For example, the anode electrolyte may be a mix of sulfate ions as well as chloride ions when the metal anion is chloride. In such embodiments, it may be desirable to have sufficient concentration of chloride ions in the electrolyte to dissolve the metal salt but not high enough to cause undesirable ionic speciation.

In some embodiments, the electrolyte and/or the metal compound are chosen based on the desired end product. For example, if a brominated hydrocarbon is desired from the reaction between the metal compound and the hydrocarbon, then a metal bromide is used as the metal compound and the sodium or potassium bromide is used as the electrolyte.

In some embodiments, the metal ions used in the electrochemical systems described herein, may be chosen based on the solubility of the metal in the anode electrolyte and/or cell voltages desired for the metal oxidation from the lower oxidation state to the higher oxidation state. For example, the voltage required to oxidize $Cr^{2+}$ to $Cr^{3+}$ may be lower than that required for $Sn^{2+}$ to $Sn^{4+}$, however, the amount of halohydrocarbon formed by the reaction of the unsaturated or saturated hydrocarbon with the $Cr^{3+}$ may be lower than the halohydrocarbon formed with $Sn^{4+}$ owing to two chlorine atoms obtained per tin molecule. Therefore, in some embodiments, where the lower cell voltages may be desired, the metal ion oxidation that results in lower cell voltage may be used, such as, but not limited to $Cr^{2+}$. For example, for the reactions where carbon dioxide is captured by the alkali produced by the cathode electrolyte, a lower voltage may be desired. In some embodiments, where a higher amount of the product, such as halohydrocarbon may be desired, the metal ion that results in higher amount of the product albeit relatively higher voltages may be used, such as, but not limited to $Sn^{2+}$. For example, the voltage of the cell may be higher for tin system as compared to the chromium system, however, the concentration of the halohydrocarbon formed with $Sn^{4+}$ may offset the higher voltage of the system. It is to be understood, that the products formed by the systems and methods described herein, such as the halohydrocarbons, sulfohydrocarbons, carbonate, bicarbonates, etc. are still green chemicals as they are made by less energy intensive processes as compared to energy input required for conventionally known methods of making the same products.

In some embodiments, the metal ion in the lower oxidation state and the metal ion in the higher oxidation state are both present in the anode electrolyte. In some embodiments, it may be desirable to have the metal ion in both the lower oxidation state and the higher oxidation state in the anode electrolyte. Suitable ratios of the metal ion in the lower and higher oxidation state in the anode electrolyte have been described herein. The mixed metal ion in the lower oxidation state with the metal ion in the higher oxidation state may assist in lower voltages in the electrochemical systems and high yield and selectivity in corresponding catalytic reactions with hydrocarbons.

In some embodiments, the metal ion in the anode electrolyte is a mixed metal ion. For example, the anode electrolyte containing the copper ion in the lower oxidation state and the copper ion in the higher oxidation state may also contain another metal ion such as, but not limited to, iron. In some embodiments, the presence of a second metal ion in the anode electrolyte may be beneficial in lowering the total energy of the electrochemical reaction in combination with the catalytic reaction.

Some examples of the metal compounds that may be used in the systems and methods of the invention include, but are not limited to, copper (II) sulfate, copper (II) nitrate, copper (I) chloride, copper (I) bromide, copper (I) iodide, iron (III) sulfate, iron (III) nitrate, iron (II) chloride, iron (II) bromide, iron (II) iodide, tin (II) sulfate, tin (II) nitrate, tin (II) chloride, tin (II) bromide, tin (II) iodide, chromium (III) sulfate, chromium (III) nitrate, chromium (II) chloride, chromium (II) bromide, chromium (II) iodide, zinc (II) chloride, zinc (II) bromide, etc.

Ligand

In some embodiments, an additive such as a ligand is used in conjunction with the metal ion to improve the efficiency of the metal ion oxidation inside the anode chamber and/or improve the catalytic reactions of the metal ion inside/outside the anode chamber such as, but not limited to reactions with unsaturated hydrocarbon and/or with saturated hydrocarbon. In some embodiments, the ligand is added along with the metal in the anode electrolyte. In some embodiments, the ligand is attached to the metal ion. In some embodiments, the ligand is attached to the metal ion by covalent, ionic and/or coordinate bonds. In some embodiments, the ligand is attached to the metal ion through vanderwaal attractions.

In some embodiments, the ligand results in one or more of the following: enhanced reactivity of the metal ion towards the unsaturated hydrocarbon or saturated hydrocarbon, enhanced selectivity of the metal ion towards halogenations of the unsaturated or saturated hydrocarbon, enhanced transfer of the halogen from the metal ion to the unsaturated hydrocarbon or saturated hydrocarbon, reduced redox potential of the electrochemical cell, enhanced solubility of the metal ion in the aqueous medium, reduced membrane cross-over of the metal ion to the cathode electrolyte in the electrochemical cell, reduced corrosion of the electrochemical cell and/or the reactor, enhanced separation of the metal ion from the organic solution after reaction with hydrocarbon, enhanced separation of the metal ion from the halogenated hydrocarbon solution (such as adsorbents), and combination thereof.

In some embodiments, the attachment of the ligand to the metal ion increases the size of the metal ion sufficiently higher to prevent its migration through the ion exchange membranes in the cell. In some embodiments, the anion exchange membrane in the electrochemical cell is such that the migration of the metal ion attached to the ligand from the anode electrolyte to the cathode electrolyte, is prevented. Such membranes are described herein below. In some embodiments, the anion exchange membrane in the electrochemical cell may be used in conjunction with the size exclusion membrane such that the migration of the metal ion attached to the ligand from the anode electrolyte to the cathode electrolyte, is prevented. In some embodiments, the attachment of the ligand to the metal ion increases the solubility of the metal ion in the aqueous medium. In some embodiments, the attachment of the ligand to the metal ion reduces the corrosion of the metals in the electrochemical cell as well as the reactor. In some embodiments, the attachment of the ligand to the metal ion increases the size of the metal ion sufficiently higher to facilitate separation of the metal ion from the halogenated hydrocarbon after the reaction. In some embodiments, the presence and/or attachment of the ligand to the metal ion may prevent formation of various halogenated species of the metal ion in the solution and favor formation of only the desired species. For example, the presence of the ligand in the copper ion solution may limit the formation of the various halogenated species of the copper ion, such as, but not limited to, $[CuCl_3]^{2-}$ or $CuCl_2^0$ but favor formation of $Cu^{2+}/Cu^+$ ion. In some embodiments, the presence and/or attachment of the ligand in the metal ion solution reduces the overall voltage of the cell by providing one or more of the advantages described above.

The "ligand" as used herein includes any ligand capable of enhancing the properties of the metal ion. In some embodiments, ligands include, but not limited to, substituted or unsubstituted aliphatic phosphine, substituted or unsubstituted aromatic phosphine, substituted or unsubstituted amino phosphine, substituted or unsubstituted crown ether, substituted or unsubstituted aliphatic nitrogen, substituted or unsubstituted cyclic nitrogen, substituted or unsubstituted aliphatic sulfur, substituted or unsubstituted cyclic sulfur, substituted or unsubstituted heterocyclic, and substituted or unsubstituted heteroaromatic.

The ligands are described in detail in U.S. patent application Ser. No. 13/799,131, filed Mar. 13, 2013, which is incorporated herein by reference in its entirety.

In some embodiments, the concentration of the ligand in the electrochemical cell is dependent on the concentration of the metal ion in the lower and/or the higher oxidation state. In some embodiments, the concentration of the ligand is between 0.25M-5M; or between 0.25M-4M; or between 0.25M-3M; or between 0.5M-5M; or between 0.5M-4M; or between 0.5M-3M; or between 0.5M-2.5M; or between 0.5M-2M; or between 0.5M-1.5M; or between 0.5M-1M; or between 1M-2M; or between 1.5M-2.5M; or between 1.5M-2M.

In some embodiments, the ratio of the concentration of the ligand and the concentration of the Cu(I) ion is between 1:1 to 4:1; or between 1:1 to 3:1; or between 1:1 to 2:1; or is 1:1; or 2:1, or 3:1, or 4:1.

In some embodiments, the solution used in the catalytic reaction, i.e., the reaction of the metal ion in the higher oxidation state with the unsaturated or saturated hydrocarbon, and the solution used in the electrochemical reaction, contain the concentration of the metal ion in the higher oxidation state, such as Cu(II), between 4.5M-7M, the concentration of the metal ion in the lower oxidation state, such as Cu(I), between 0.25M-1.5M, and the concentration of the ligand between 0.25M-6M. In some embodiments, the concentration of the sodium chloride in the solution may affect the solubility of the ligand and/or the metal ion; the yield and selectivity of the catalytic reaction; and/or the efficiency of the electrochemical cell. Accordingly, in some embodiments, the concentration of sodium chloride in the solution is between 1M-3M. In some embodiments, the solution used in the catalytic reaction, i.e., the reaction of the metal ion in the higher oxidation state with the unsaturated or saturated hydrocarbon, and the solution used in the electrochemical reaction, contain the concentration of the metal ion in the higher oxidation state, such as Cu(II), between 4.5M-7M, the concentration of the metal ion in the lower oxidation state, such as Cu(I), between 0.25M-1.5M, the concentration of the ligand between 0.25M-6M, and the concentration of sodium chloride between 1M-3M.

Anode

In some embodiments, the anode may contain a corrosion stable, electrically conductive base support. Such as, but not limited to, amorphous carbon, such as carbon black, fluorinated carbons like the specifically fluorinated carbons described in U.S. Pat. No. 4,908,198 and available under the trademark SFC™ carbons. Other examples of electrically conductive base materials include, but not limited to, sub-stoichiometric titanium oxides, such as, Magneli phase sub-stoichiometric titanium oxides having the formula $TiO_x$ wherein x ranges from about 1.67 to about 1.9. Some examples of titanium sub-oxides include, without limitation, titanium oxide $Ti_4O_7$. The electrically conductive base materials also include, without limitation, metal titanates such as $M_xTi_yO_z$ such as $M_xTi_4O_7$, etc. In some embodiments, carbon based materials provide a mechanical support or as blending materials to enhance electrical conductivity but may not be used as catalyst support to prevent corrosion.

In some embodiments, the anode is not coated with an electrocatalyst. In some embodiments, the gas-diffusion electrodes or general electrodes described herein (including anode and/or cathode) contain an electrocatalyst for aiding in electrochemical dissociation, e.g. reduction of oxygen at the cathode or the oxidation of the metal ion at the anode. Examples of electrocatalysts include, but not limited to, highly dispersed metals or alloys of the platinum group metals, such as platinum, palladium, ruthenium, rhodium, iridium, or their combinations such as platinum-rhodium, platinum-ruthenium, titanium mesh coated with PtIr mixed metal oxide or titanium coated with galvanized platinum; electrocatalytic metal oxides, such as, but not limited to, $IrO_2$; gold, tantalum, carbon, graphite, organometallic macrocyclic compounds, and other electrocatalysts well known in the art for electrochemical reduction of oxygen or oxidation of metal.

In some embodiments, the electrodes described herein, relate to porous homogeneous composite structures as well as heterogeneous, layered type composite structures wherein each layer may have a distinct physical and compositional make-up, e.g. porosity and electroconductive base to prevent flooding, and loss of the three phase interface, and resulting electrode performance.

In some embodiments, the electrodes provided herein may include anodes and cathodes having porous polymeric layers on or adjacent to the anolyte or catholyte solution side of the electrode which may assist in decreasing penetration and electrode fouling. Stable polymeric resins or films may be included in a composite electrode layer adjacent to the anolyte comprising resins formed from non-ionic polymers, such as polystyrene, polyvinyl chloride, polysulfone, etc., or ionic-type charged polymers like those formed from polystyrenesulfonic acid, sulfonated copolymers of styrene and vinylbenzene, carboxylated polymer derivatives, sulfonated or carboxylated polymers having partially or totally fluorinated hydrocarbon chains and aminated polymers like polyvinylpyridine. Stable microporous polymer films may also be included on the dry side to inhibit electrolyte penetration. In some embodiments, the gas-diffusion cathodes includes such cathodes known in the art that are coated with high surface area coatings of precious metals such as gold and/or silver, precious metal alloys, nickel, and the like.

In some embodiments, the methods and systems provided herein include anode that allows increased diffusion of the electrolyte in and around the anode. Applicants found that the shape and/or geometry of the anode may have an effect on the flow or the velocity of the anode electrolyte around the anode in the anode chamber which in turn may improve the mass transfer and reduce the voltage of the cell. In some embodiments, the methods and systems provided herein include anode that is a "diffusion enhancing" anode. The "diffusion enhancing" anode as used herein includes anode that enhances the diffusion of the electrolyte in and/or around the anode thereby enhancing the reaction at the anode. In some embodiments, the diffusion enhancing anode is a porous anode. The "porous anode" as used herein includes an anode that has pores in it. The diffusion enhancing anode such as, but not limited to, the porous anode used in the methods and systems provided herein, may have several advantages over the non-diffusing or non-porous anode in the electrochemical systems including, but not limited to, higher surface area; increase in active sites; decrease in voltage; decrease or elimination of resistance by the anode electrolyte; increase in current density; increase in turbulence in the anode electrolyte; and/or improved mass transfer.

The diffusion enhancing anode such as, but not limited to, the porous anode may be flat, unflat, or combinations thereof. For example, in some embodiments, the diffusion enhancing anode such as, but not limited to, the porous anode is in a flat form including, but not limited to, an expanded flattened form, a perforated plate, a reticulated structure, etc. In some embodiments, the diffusion enhancing anode such as, but not limited to, the porous anode includes an expanded mesh or is a flat expanded mesh anode.

In some embodiments, the diffusion enhancing anode such as, but not limited to, the porous anode is unflat or has a corrugated geometry. In some embodiments, the corrugated geometry of the anode may provide an additional advantage of the turbulence to the anode electrolyte and improve the mass transfer at the anode. The "corrugation" or "corrugated geometry" or "corrugated anode" as used herein includes an anode that is not flat or is unflat. The corrugated geometry of the anode includes, but not limited to, unflattened, expanded unflattened, staircase, undulations, wave like, 3-D, crimp, groove, pleat, pucker, ridge, ruche, ruffle, wrinkle, woven mesh, punched tab style, etc.

Figure 5:
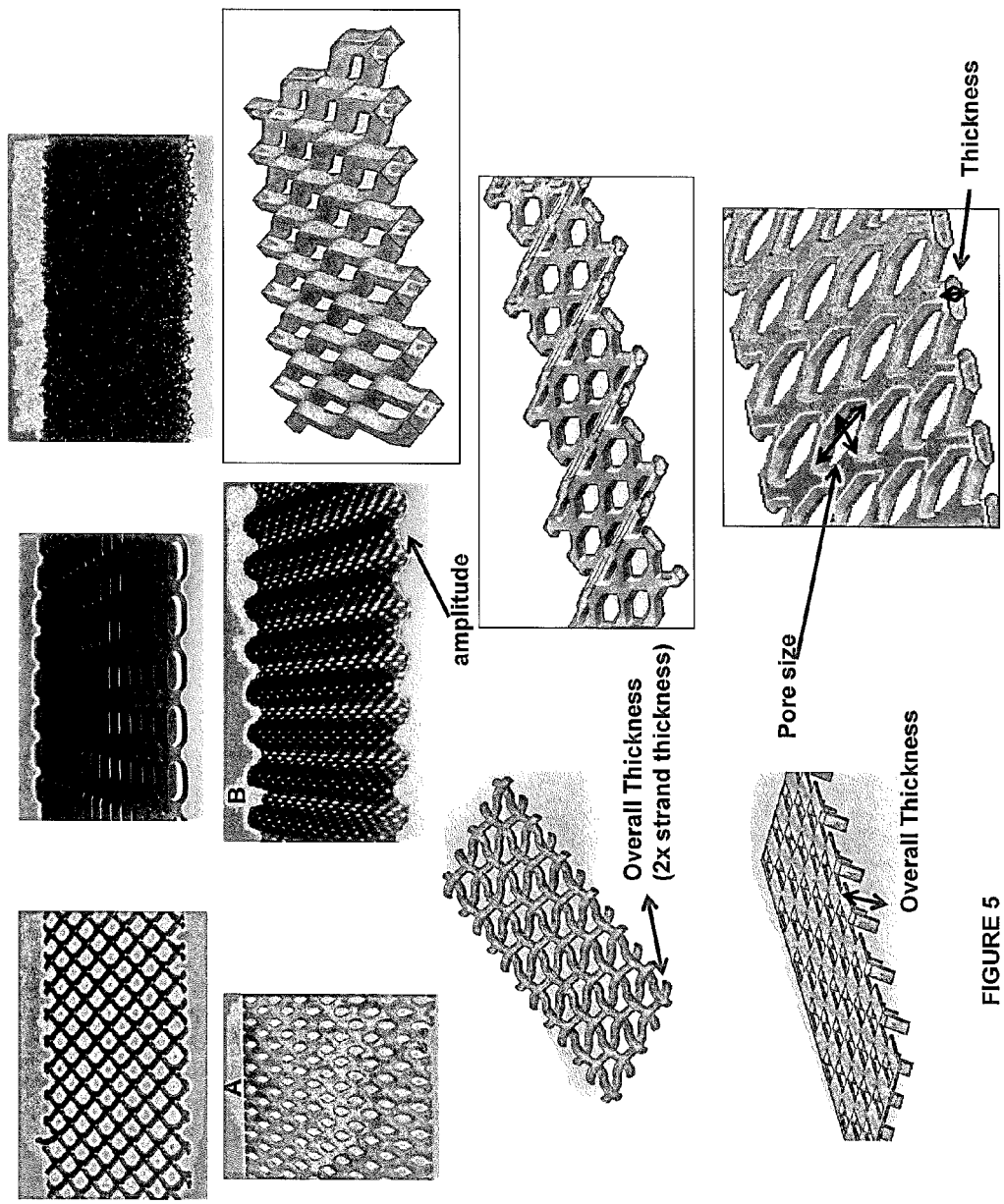
FIG. 5 illustrates few examples of the diffusion enhancing anode such as, but not limited to, the porous anode, as described herein.

Few examples of the flat and the corrugated geometry of the diffusion enhancing anode such as, but not limited to, the porous anode are as illustrated in FIG. 5. These examples are for illustration purposes only and any other variation from these geometries is well within the scope of the invention. The figure A in FIG. 5 is an example of a flat expanded anode and the figure B in FIG. 5 is an example of the corrugated anode.

In some embodiments of the foregoing methods and embodiments, the use of the diffusion enhancing anode such as, but not limited to, the porous anode results in the voltage savings of between 10-500 mV, or between 50-250 mV, or between 100-200 mV, or between 200-400 mV, or between 25-450 mV, or between 250-350 mV, or between 100-500 mV, as compared to the non-diffusing or the non-porous anode.

In some embodiments of the foregoing methods and embodiments, the use of the corrugated anode results in the voltage savings of between 10-500 mV, or between 50-250 mV, or between 100-200 mV, or between 200-400 mV, or between 25-450 mV, or between 250-350 mV, or between 100-500 mV, as compared to the flat porous anode.

The diffusion enhancing anode such as, but not limited to, the porous anode may be characterized by various parameters including, but not limited to, mesh number which is a number of lines of mesh per inch; pore size; thickness of the wire or wire diameter; percentage open area; amplitude of the corrugation; repetition period of the corrugation; etc. These characteristics of the diffusion enhancing anode such as, but not limited to, the porous anode may affect the properties of the porous anode, such as, but not limited to, increase in the surface area for the anode reaction; reduction of solution resistance; reduction of voltage applied across the anode and the cathode; enhancement of the electrolyte turbulence across the anode; and/or improved mass transfer at the anode.

In some embodiments of the foregoing methods and embodiments, the diffusion enhancing anode such as, but not limited to, the porous anode may have a pore opening size (as illustrated in FIG. 5) ranging between 2×1 mm to 20×10 mm; or between 2×1 mm to 10×5 mm; or between 2×1 mm to 5×5 mm; or between 1×1 mm to 20×10 mm; or between 1×1 mm to 10×5 mm; or between 1×1 mm to 5×5 mm; or between 5×1 mm to 10×5 mm; or between 5×1 mm to 20×10 mm; between 10×5 mm to 20×10 mm and the like. It is to be understood that the pore size of the porous anode may also be dependent on the geometry of the pore. For example, the geometry of the pore may be diamond shaped or square shaped. For the diamond shaped geometry, the pore size may be, e.g., 3×10 mm with 3 mm being widthwise and 10 mm being lengthwise of the diamond, or vice versa. For the square shaped geometry, the pore size would be, e.g., 3 mm each side. The woven mesh may be the mesh with square shaped pores and the expanded mesh may be the mesh with diamond shaped pores.

In some embodiments of the foregoing methods and embodiments, the diffusion enhancing anode such as, but not limited to, the porous anode may have a pore wire thickness or mesh thickness (as illustrated in FIG. 5) ranging between 0.5 mm to 5 mm; or between 0.5 mm to 4 mm; or between 0.5 mm to 3 mm; or between 0.5 mm to 2 mm; or between 0.5 mm to 1 mm; or between 1 mm to 5 mm; or between 1 mm to 4 mm; or between 1 mm to 3 mm; or between 1 mm to 2 mm; or between 2 mm to 5 mm; or between 2 mm to 4 mm; or between 2 mm to 3 mm; or between 0.5 mm to 2.5 mm; or between 0.5 mm to 1.5 mm; or between 1 mm to 1.5 mm; or between 1 mm to 2.5 mm; or between 2.5 mm to 3 mm; or 0.5 mm; or 1 mm; or 2 mm; or 3 mm.

In some embodiments of the foregoing methods and embodiments, when the diffusion enhancing anode such as, but not limited to, the porous anode is the corrugated anode, then the corrugated anode may have a corrugation amplitude (as illustrated in FIG. 5) ranging between 1 mm to 8 mm; or between 1 mm to 7 mm; or between 1 mm to 6 mm; or between 1 mm to 5 mm; or between 1 mm to 4 mm; or between 1 mm to 4.5 mm; or between 1 mm to 3 mm; or between 1 mm to 2 mm; or between 2 mm to 8 mm; or between 2 mm to 6 mm; or between 2 mm to 4 mm; or between 2 mm to 3 mm; or between 3 mm to 8 mm; or between 3 mm to 7 mm; or between 3 mm to 5 mm; or between 3 mm to 4 mm; or between 4 mm to 8 mm; or between 4 mm to 5 mm; or between 5 mm to 7 mm; or between 5 mm to 8 mm.

In some embodiments of the foregoing methods and embodiments, when the diffusion enhancing anode such as, but not limited to, the porous anode is the corrugated anode, then the corrugated anode may have a corrugation period (not illustrated in figures) ranging between 2 mm to 35 mm; or between 2 mm to 32 mm; or between 2 mm to 30 mm; or between 2 mm to 25 mm; or between 2 mm to 20 mm; or between 2 mm to 16 mm; or between 2 mm to 10 mm; or between 5 mm to 35 mm; or between 5 mm to 30 mm; or between 5 mm to 25 mm; or between 5 mm to 20 mm; or between 5 mm to 16 mm; or between 5 mm to 10 mm; or between 15 mm to 35 mm; or between 15 mm to 30 mm; or between 15 mm to 25 mm; or between 15 mm to 20 mm; or between 20 mm to 35 mm; or between 25 mm to 30 mm; or between 25 mm to 35 mm; or between 25 mm to 30 mm.

In some embodiments, the diffusion enhancing anode such as, but not limited to, the porous anode is made of an electro conductive base metal such as titanium coated with or without electrocatalysts. Some examples of electrically conductive base materials include, but not limited to, sub-stoichiometric titanium oxides, such as, Magneli phase sub-stoichiometric titanium oxides having the formula $TiO_x$ wherein x ranges from about 1.67 to about 1.9. Some examples of titanium sub-oxides include, without limitation, titanium oxide $Ti_4O_7$. The electrically conductive base materials also include, without limitation, metal titanates such as $M_xTi_yO_z$ such as $M_xTi_4O_7$, etc. Examples of electrocatalysts have been described herein and include, but not limited to, highly dispersed metals or alloys of the platinum group metals, such as platinum, palladium, ruthenium, rhodium, iridium, or their combinations such as platinum-rhodium, platinum-ruthenium, titanium mesh coated with PtIr mixed metal oxide or titanium coated with galvanized platinum; electrocatalytic metal oxides, such as, but not limited to, $IrO_2$; gold, tantalum, carbon, graphite, organometallic macrocyclic compounds, and other electrocatalysts well known in the art. The diffusion enhancing anode such as, but not limited to, the porous anode may be commercially available or may be fabricated with appropriate metals. The electrodes may be coated with electrocatalysts using processes well known in the art. For example, the metal may be dipped in the catalytic solution for coating and may be subjected to processes such as heating, sand blasting etc. Such methods of fabricating the anodes and coating with catalysts are well known in the art.

In some embodiments of the methods and systems described herein, a turbulence promoter is used in the anode compartment to improve mass transfer at the anode. For example, as the current density increases in the electrochemical cell, the mass transfer controlled reaction rate at the anode is achieved. The laminar flow of the anolyte may cause resistance and diffusion issues. In order to improve the mass transfer at the anode and thereby reduce the voltage of the cell, a turbulence promoter may be used in the anode compartment. A "turbulence promoter" as used herein includes a component in the anode compartment of the electrochemical cell that provides turbulence. In some embodiments, the turbulence promoter may be provided at the back of the anode, i.e. between the anode and the wall of the electrochemical cell and/or in some embodiments, the turbulence promoter may be provided between the anode and the anion exchange membrane. For example only, the electrochemical systems shown in FIG. 1A, 1B, 2, 4A or 4B, may have a turbulence promoter between the anode and the ion exchange membrane such as the anion exchange membrane and/or have the turbulence promoter between the anode and the outer wall of the cell.

An example of the turbulence promoter is bubbling of the gas in the anode compartment. The gas can be any inert gas that does not react with the constituents of the anolyte. For example, the gas includes, but not limited to, air, nitrogen, argon, and the like. The bubbling of the gas at the anode can stir up the anode electrolyte and improve the mass transfer at the anode. The improved mass transfer can result in the reduced voltage of the cell. Other examples of the turbulence promoter include, but not limited to, incorporating a carbon cloth next to the anode, incorporating a carbon/graphite felt next to the anode, an expanded plastic next to the anode, a fishing net next to the anode, a combination of the foregoing, and the like.

Cathode

Any of the cathodes provided herein can be used in combination with any of the anodes described above. In some embodiments, the cathode used in the electrochemical systems of the invention, is a hydrogen gas producing cathode.

Following are the reactions that take place at the cathode and the anode:

$H_2O+e^-\rightarrow \frac{1}{2}H_2+OH^-$(cathode)

$M^{L+}\rightarrow M^{H+}+xe^-$(anode where $x=1-3$)

For example, $Fe^{2+}\rightarrow Fe^{3+}+e^-$(anode)

$Cr^{2+}\rightarrow Cr^{3+}+e^-$(anode)

$Sn^{2+}\rightarrow Sn^{4+}+2e^-$(anode)

$Cu^+\rightarrow Cu^{2+}+e^-$(anode)

The hydrogen gas formed at the cathode may be vented out or captured and stored for commercial purposes. The $M^{H+}$ formed at the anode combines with halide ions or sulfate ions, e.g. chloride ions to form metal chloride in the higher oxidation state such as, but not limited to, $FeCl_3$, $CrCl_3$, $SnCl_4$, or $CuCl_2$ etc. The hydroxide ion formed at the cathode combines with sodium ions to form sodium hydroxide. It is to be understood that chloride ions in this application are for illustration purposes only and that other equivalent ions such as, but not limited to, sulfate, bromide or iodide are also well within the scope of the invention and would result in corresponding metal halide or metal sulfate in the anode electrolyte.

In some embodiments, the cathode used in the electrochemical systems of the invention, is a hydrogen gas producing cathode that does not form an alkali. Following are the reactions that take place at the cathode and the anode:

$2H^++2e^-\rightarrow H_2$(cathode)

$M^{L+}\rightarrow M^{H+}+xe^-$(anode where $x=1-3$)

For example, $Fe^{2+}\rightarrow Fe^{3+}+e^-$(anode)

$Cr^{2+}\rightarrow Cr^{3+}+e^-$(anode)

$Sn^{2+}\rightarrow Sn^{4+}+2e^-$(anode)

$Cu^+\rightarrow Cu^{2+}+e^-$(anode)

The hydrogen gas may be vented out or captured and stored for commercial purposes. The $M^{H+}$ formed at the anode combines with halide ions or sulfate ions, e.g. chloride ions to form metal chloride in the higher oxidation state such as, but not limited to, $FeCl_3$, $CrCl_3$, $SnCl_4$, or $CuCl_2$ etc.

In some embodiments, the cathode in the electrochemical systems of the invention may be a gas-diffusion cathode. In some embodiments, the cathode in the electrochemical systems of the invention may be a gas-diffusion cathode forming an alkali at the cathode. As used herein, the "gas-diffusion cathode," or "gas-diffusion electrode," or other equivalents thereof include any electrode capable of reacting a gas to form ionic species. In some embodiments, the gas-diffusion cathode, as used herein, is an oxygen depolarized cathode (ODC). Such gas-diffusion cathode may be called gas-diffusion electrode, oxygen consuming cathode, oxygen reducing cathode, oxygen breathing cathode, oxygen depolarized cathode, and the like.

Following are the reactions that may take place at the anode and the cathode.

$H_2O+\frac{1}{2}O_2+2e^-\rightarrow 2OH^-$(cathode)

$M^{L+}\rightarrow M^{H+}+xe^-$(anode where $x=1-3$)

For example, $2Fe^{2+}\rightarrow 2Fe^{3+}+2e^-$(anode)

$2Cr^{2+}\rightarrow 2Cr^{3+}+2e^-$(anode)

$Sn^{2+}\rightarrow Sn^{4+}+2e^-$(anode)

$2Cu^+\rightarrow 2Cu^{2+}+2e^-$(anode)

The $M^{H+}$ formed at the anode combines with halide ions or sulfate ions, e.g. chloride ions to form metal chloride $MCl_n$ such as, but not limited to, $FeCl_3$, $CrCl_3$, $SnCl_4$, or $CuCl_2$ etc. The hydroxide ion formed at the cathode reacts with sodium ions to form sodium hydroxide. The oxygen at the cathode may be atmospheric air or any commercial available source of oxygen.

The methods and systems containing the gas-diffusion cathode or the ODC, as described herein may result in voltage savings as compared to methods and systems that include the hydrogen gas producing cathode. The voltage savings in-turn may result in less electricity consumption and less carbon dioxide emission for electricity generation. This may result in the generation of greener chemicals such as sodium hydroxide, halogenated hydrocarbons and/or acids, that are formed by the efficient and energy saving methods and systems of the invention.

While the methods and systems containing the gas-diffusion cathode or the ODC result in voltage savings as compared to methods and systems containing the hydrogen gas producing cathode, both the systems i.e. systems containing the ODC and the systems containing hydrogen gas producing cathode of the invention, show significant voltage savings as compared to chlor-alkali system conventionally known in the art. The voltage savings in-turn may result in less electricity consumption and less carbon dioxide emission for electricity generation. This may result in the generation of greener chemicals such as sodium hydroxide and/or halogenated hydrocarbons, that are formed by the efficient and energy saving methods and systems of the invention. For example, the voltage savings is beneficial in production of the halogenated hydrocarbons, such as EDC, which is typically formed by reacting ethylene with chlorine gas generated by the high voltage consuming chlor-alkali process. In some embodiments, the electrochemical system of the invention (2 or 3-compartment cells with hydrogen gas producing cathode or ODC) has a theoretical voltage savings of more than 0.5V, or more than 1V, or more than 1.5V, or between 0.5-3V, as compared to chlor-alkali process. In some embodiments, this voltage saving is achieved with a cathode electrolyte pH of between 7-15, or between 7-14, or between 6-12, or between 7-12, or between 7-10.

For example, theoretical $E_{anode}$ in the chlor-alkali process is about 1.36V undergoing the reaction as follows:

$$2Cl^- \rightarrow Cl_2 + 2e^-,$$

Theoretical $E_{cathode}$ in the chlor-alkali process is about −0.83V (at pH>14) undergoing the reaction as follows:

$$2H_2O + 2e^- = H_2 + 2OH^-$$

Theoretical $E_{total}$ for the chlor-alkali process then is 2.19V. Theoretical $E_{total}$ for the hydrogen gas producing cathode in the system of the invention is between 0.989 to 1.53V and $E_{total}$ for ODC in the system of the invention then is between −0.241 to 0.3V, depending on the concentration of copper ions in the anode electrolyte. Therefore, the electrochemical systems of the invention bring the theoretical voltage savings in the cathode chamber or the theoretical voltage savings in the cell of greater than 3V or greater than 2V or between 0.5-2.5V or between 0.5-2.0V or between 0.5-1.5V or between 0.5-1.0V or between 1-1.5V or between 1-2V or between 1-2.5V or between 1.5-2.5V, as compared to the chlor-alkali system.

In some embodiments, the cathode in the electrochemical systems of the invention may be a gas-diffusion cathode that reacts HCl and oxygen gas to form water.

Following are the reactions that may take place at the anode and the cathode.

$$2H^+ + \tfrac{1}{2}O_2 + 2e^- \rightarrow H_2O \text{(cathode)}$$

$$M^{L+} \rightarrow M^{H+} + xe^- \text{(anode where } x=1\text{-}3\text{)}$$

For example, $2Fe^{2+} \rightarrow 2Fe^{3+} + 2e^-$ (anode)

$$2Cr^{2+} \rightarrow 2Cr^{3+} + 2e^- \text{(anode)}$$

$$Sn^{2+} \rightarrow Sn^{4+} + 2e^- \text{(anode)}$$

$$2Cu^+ \rightarrow 2Cu^{2+} + 2e^- \text{(anode)}$$

The $M^{H+}$ formed at the anode combines with chloride ions to form metal chloride $MCl_n$ such as, but not limited to, $FeCl_3$, $CrCl_3$, $SnCl_4$, or $CuCl_2$ etc. The oxygen at the cathode may be atmospheric air or any commercial available source of oxygen.

Alkali in the Cathode Chamber

The cathode electrolyte containing the alkali maybe withdrawn from the cathode chamber. In some embodiments, the alkali produced in the methods and systems provided herein is used as is commercially or is used in commercial processes known in the art. The purity of the alkali formed in the methods and systems may vary depending on the end use requirements. For example, methods and systems provided herein that use an electrochemical cell equipped with membranes may form a membrane quality alkali which may be substantially free of impurities. In some embodiments, a less pure alkali may also be formed by avoiding the use of membranes or by adding the carbon to the cathode electrolyte. In some embodiments, the alkali may be separated from the cathode electrolyte using techniques known in the art, including but not limited to, diffusion dialysis. In some embodiments, the alkali formed in the cathode electrolyte is more than 2% w/w or more than 5% w/w or between 5-50% w/w.

In some embodiments, the systems include a collector configured to collect the alkali from the cathode chamber and connect it to the appropriate process which may be any means to collect and process the alkali including, but not limited to, tanks, collectors, pipes etc. that can collect, process, and/or transfer the alkali produced in the cathode chamber for use in the various commercial processes.

In some embodiments, the alkali formed in the cathode electrolyte is used in making products such as, but not limited to carbonates and/or bicarbonates by contacting the carbon dioxide with the alkali. Such contact of the carbon dioxide, the sources of the carbon dioxide, and the formation of carbonate and/or bicarbonate products, is fully described in U.S. patent application Ser. No. 13/799,131, filed Mar. 13, 2013, which is incorporated herein by reference in its entirety.

Ion Exchange Membrane

In some embodiments, the cathode electrolyte and the anode electrolyte are separated in part or in full by an ion exchange membrane. In some embodiments, the ion exchange membrane is an anion exchange membrane or a cation exchange membrane. In some embodiments, the cation exchange membranes in the electrochemical cell, as disclosed herein, are conventional and are available from, for example, Asahi Kasei of Tokyo, Japan; or from Membrane International of Glen Rock, N.J., or DuPont, in the USA. Examples of CEM include, but are not limited to, N2030WX (Dupont), F8020/F8080 (Flemion), and F6801 (Aciplex). CEMs that are desirable in the methods and systems of the invention have minimal resistance loss, greater than 90% selectivity, and high stability in concentrated caustic. AEMs, in the methods and systems of the invention are exposed to concentrated metallic salt anolytes and saturated brine stream. It is desirable for the AEM to allow passage of salt ion such as chloride ion to the anolyte but reject the metallic ion species from the anolyte (FIG. 3A). In some embodiments, metallic salts may form various ion species (cationic, anionic, and/or neutral) including but not limited to, $MCl^+$, $MCl_2^-$, $MCl_2^0$, $M^{2+}$ etc. and it is desirable for such complexes to not pass through AEM or not foul the membranes.

In some embodiments, the AEM used in the methods and systems provided herein, is also substantially resistant to the organic compounds (such as ligands or hydrocarbons in the recycled metal solution) such that AEM does not interact with the organics and/or the AEM does not react or absorb metal ions. In some embodiments, this can be achieved, for example only, by using a polymer that does not contain a free radical or anion available for reaction with organics or with metal ions. For example only, a fully quarternized amine containing polymer may be used as an AEM.

In some embodiments, the membranes used in the methods and systems provided herein are ionomer membranes reinforced with a material for reinforcement and are of a certain thickness. For example, in some embodiments, the thickness of the membrane is between 20-130 um; or between 20-110 um; or between 20-110 um; or between 20-80 um; or between 20-75 um; or between 20-60 um; or between 20-50 um; or between 20-40 um; or between 20-35 um. In some embodiments, the membrane may be reinforced with materials such as, but not limited to, polymers, such as, polyethylene (PET), polypropylene (PP), and polyether ether ketone (PK), and glass fibers (GF). It is understood that other polymers that may be used for reinforcement of the AEM are well within the scope of the invention. In some embodiments, the membranes used in the methods and systems provided herein can withstand high temperatures, such as, but not limited to, temperatures higher than 70° C., for example between 70-200° C.; or between 70-175° C.; or between 70-150° C.; or between 70-100° C. Some of the membranes sold by FumaTech in Fumasep series may be used in the methods and systems provided herein. The examples, include, but not limited to, FAS-PK-130, FAS-PK-75, FAS-PK-50, FAS-PP-20, FAS-PP-130, FAS-PP-75, FAS-PP-50, FAS-PP-20, FAS-PET-130, FAS-PET-75, FAS-PET-50, FAS-PET-20, FAS-GF-75, FAS-GF-50, FAS-GF-20, FAA-PK-130, FAA-PK-75, FAA-PK-50, FAA-PP-20, FAS-PP-130, FAA-PP-75, FAA-PP-50, FAA-PP-20, FAA-PET-130, FAA-PET-75, FAA-PET-50, FAA-PET-20, FAA-GF-75, FAA-GF-50, FAA-GF-20. In some embodiments, the membrane used in the methods and systems of the invention has thickness between 20-75 um, such as, e.g. FAA-PP-75. The nomenclature of the aforementioned membranes includes FAA or FAS-reinforcement material-thickness. Provided in Example 5 herein, are some of the membranes that have been tested for the methods and systems of the invention.

Accordingly, provided herein are methods comprising contacting an anode with a metal ion in an anode electrolyte in an anode chamber; converting the metal ion from a lower oxidation state to a higher oxidation state at the anode; contacting a cathode with a cathode electrolyte in a cathode chamber; forming an alkali, water, or hydrogen gas at the cathode; and using an anion exchange membrane that comprises a reinforced material and a thickness of between 20-130 um. In some embodiments, the foregoing method further includes reacting the metal ion in the higher oxidation state with the saturated or unsaturated hydrocarbon to form halo or sulfohydrocarbon. In some embodiments, the foregoing methods further include using the reactor configurations described herein. After separation and/or purification, as described herein, the metal ion solution may be re-circulated back to the anode electrolyte. In such embodiments, the AEM as described above prevents fouling of the membrane by the residual organics in the metal solution. Also provided herein are methods comprising contacting an anode with a metal ion in an anode electrolyte in an anode chamber; converting the metal ion from a lower oxidation state to a higher oxidation state at the anode; contacting a cathode with a cathode electrolyte in a cathode chamber; forming an alkali at the cathode; separating the anode electrolyte from a brine compartment (or the third electrolyte described herein above) with an anion exchange membrane; separating the cathode electrolyte from the brine compartment by a cation exchange membrane; and preventing migration of the metal ions from the anode electrolyte to the brine compartment by using the anion exchange membrane that comprises a reinforced material and a thickness of between 20-130 um.

In some embodiments of the aforementioned methods, the reinforced material is selected from, but not limited to, polymers such as, polyethylene, polypropylene, and polyether ether ketone, and glass fibers. In some embodiments of the aforementioned methods and embodiments, the thickness of the AEM is between 20-75 um or between 50-100 um. In some embodiments of the aforementioned methods and embodiments, the anion exchange membrane has an ohmic resistance of between 1-3 $\Omega cm^2$. In some embodiments of the aforementioned methods and embodiments, the anion exchange membrane rejects more than 80%, or more than 90%, or more than 99%, or about 99.9% of all metal ions from the anode electrolyte passing into the third electrolyte or the brine compartment or the cathode electrolyte. In some embodiments of the aforementioned methods and embodiments, the anion exchange membrane operates at temperatures greater than 70° C.

There are also provided systems comprising an anode in contact with a metal ion in an anode electrolyte in an anode chamber wherein the anode is configured to convert the metal ion from a lower oxidation state to a higher oxidation state in the anode chamber; a cathode in contact with a cathode electrolyte in a cathode chamber wherein the cathode is configured to form an alkali, water, or hydrogen gas in the cathode chamber; and an anion exchange membrane wherein the anion exchange membrane comprises a reinforced material and a thickness of between 20-130 um or between 20-75 um or between 50-100 um. There are also provided systems comprising an anode in contact with a metal ion in an anode electrolyte in an anode chamber wherein the anode is configured to convert the metal ion from a lower oxidation state to a higher oxidation state in the anode chamber; a cathode in contact with a cathode electrolyte in a cathode chamber wherein the cathode is configured to form an alkali in the cathode chamber; an anion exchange membrane separating the anode electrolyte from a brine compartment (or third chamber); and a cation exchange membrane separating the cathode electrolyte from the brine compartment, wherein the anion exchange membrane comprises a reinforced material and a thickness of between 20-130 um or between 20-75 um or between 50-100 um.

In some embodiments of the aforementioned systems, the reinforced material is selected from, but not limited to, polymers such as, polyethylene, polypropylene, and polyether ether ketone, and glass fibers. In some embodiments of the aforementioned systems and embodiments, the thickness of the AEM is between 50-100 um. In some embodiments of the aforementioned systems and embodiments, the anion exchange membrane is configured such that the AEM has an ohmic resistance of between 1-3 $\Omega cm^2$. In some embodiments of the aforementioned systems and embodiments, the anion exchange membrane is configured such that the AEM rejects more than 80%, or more than 90%, or more than 99%, or about 99.9% of all metal ions from the anode electrolyte to pass into the third electrolyte or the brine compartment or the cathode electrolyte. In some embodiments of the aforementioned systems and embodiments, the anion exchange membrane operates at temperatures greater than 70° C.

Examples of cationic exchange membranes include, but not limited to, cationic membrane consisting of a perfluorinated polymer containing anionic groups, for example sulphonic and/or carboxylic groups. However, it may be appreciated that in some embodiments, depending on the need to restrict or allow migration of a specific cation or an anion species between the electrolytes, a cation exchange membrane that is more restrictive and thus allows migration of one species of cations while restricting the migration of another species of cations may be used as, e.g., a cation exchange membrane that allows migration of sodium ions into the cathode electrolyte from the anode electrolyte while restricting migration of other ions from the anode electrolyte into the cathode electrolyte, may be used (FIG. 3B). Similarly, in some embodiments, depending on the need to restrict or allow migration of a specific anion species between the electrolytes, an anion exchange membrane that is more restrictive and thus allows migration of one species of anions while restricting the migration of another species of anions may be used as, e.g., an anion exchange membrane that allows migration of chloride ions into the anode electrolyte from the cathode electrolyte while restricting migration of hydroxide ions from the cathode electrolyte into the anode electrolyte, may be used. Such restrictive cation exchange membranes are commercially available and can be selected by one ordinarily skilled in the art.

In some embodiments, the membranes may be selected such that they can function in an acidic and/or basic electrolytic solution as appropriate. Other desirable characteristics of the membranes include high ion selectivity, low ionic resistance, high burst strength, and high stability in an acidic electrolytic solution in a temperature range of room temperature to 150° C. or higher, or a alkaline solution in similar temperature range may be used. In some embodiments, it is desirable that the ion exchange membrane prevents the transport of the metal ion from the anolyte to the catholyte. In some embodiments, a membrane that is stable in the range of 0° C. to 150° C.; 0° C. to 90° C.; or 0° C. to 80° C.; or 0° C. to 70° C.; or 0° C. to 60° C.; or 0° C. to 50° C.; or 0° C. to 40° C., or 0° C. to 30° C., or 0° C. to 20° C., or 0° C. to 10° C., or higher may be used. In some embodiments, a membrane that is stable in the range of 0° C. to 90° C.; or 0° C. to 80° C.; or 0° C. to 70° C.; or 0° C. to 60° C.; or 0° C. to 50° C.; or 0° C. to 40° C., may be used. For other embodiments, it may be useful to utilize an ion-specific ion exchange membranes that allows migration of one type of cation but not another; or migration of one type of anion and not another, to achieve a desired product or products in an electrolyte. In some embodiments, the membrane may be stable and functional for a desirable length of time in the system, e.g., several days, weeks or months or years at temperatures in the range of 0° C. to 90° C.; or 0° C. to 80° C.; or 0° C. to 70° C.; or 0° C. to 60° C.; or 0° C. to 50° C.; or 0° C. to 40° C.; or 0° C. to 30° C.; or 0° C. to 20° C.; or 0° C. to 10° C., and higher and/or lower. In some embodiments, for example, the membranes may be stable and functional for at least 1 day, at least 5 days, 10 days, 15 days, 20 days, 100 days, 1000 days, 5-10 years, or more in electrolyte temperatures at 100° C., 90° C., 80° C., 70° C., 60° C., 50° C., 40° C., 30° C., 20° C., 10° C., 5° C. and more or less.

The ohmic resistance of the membranes may affect the voltage drop across the anode and cathode, e.g., as the ohmic resistance of the membranes increase, the voltage across the anode and cathode may increase, and vice versa. Membranes that can be used include, but are not limited to, membranes with relatively low ohmic resistance and relatively high ionic mobility; and membranes with relatively high hydration characteristics that increase with temperatures, and thus decreasing the ohmic resistance. By selecting membranes with lower ohmic resistance known in the art, the voltage drop across the anode and the cathode at a specified temperature can be lowered.

Scattered through membranes may be ionic channels including acid groups. These ionic channels may extend from the internal surface of the matrix to the external surface and the acid groups may readily bind water in a reversible reaction as water-of-hydration. This binding of water as water-of-hydration may follow first order reaction kinetics, such that the rate of reaction is proportional to temperature. Consequently, membranes can be selected to provide a relatively low ohmic and ionic resistance while providing for improved strength and resistance in the system for a range of operating temperatures.

Electrolytes

In some embodiments of the methods and systems described herein, the anode electrolyte containing the metal ion may contain a mixture of the metal ion in the lower oxidation state and the metal ion in the higher oxidation state. In some embodiments, it may be desirable to have a mix of the metal ion in the lower oxidation state and the metal ion in the higher oxidation state in the anode electrolyte. In some embodiments, the anode electrolyte that is contacted with the unsaturated or saturated hydrocarbon contains the metal ion in the lower oxidation state and the metal ion in the higher oxidation state. In some embodiments, the metal ion in the lower oxidation state and the metal ion in the higher oxidation state are present in a ratio such that the reaction of the metal ion with the unsaturated or saturated hydrocarbon to form halo or sulfohydrocarbon takes place. In some embodiments, the ratio of the metal ion in the higher oxidation state to the metal ion in the lower oxidation state is between 20:1 to 1:20, or between 14:1 to 1:2; or between 14:1 to 8:1; or between 14:1 to 7:1: or between 2:1 to 1:2; or between 1:1 to 1:2; or between 4:1 to 1:2; or between 7:1 to 1:2.

In some embodiments of the methods and systems described herein, the anode electrolyte in the electrochemical systems and methods provided herein contains the metal ion in the higher oxidation state in the range of 4-7M, the metal ion in the lower oxidation state in the range of 0.1-2M and sodium chloride in the range of 1-3M. The anode electrolyte may optionally contain 0.01-0.1M hydrochloric acid. In some embodiments of the methods and systems described herein, the anode electrolyte reacted with the unsaturated or saturated hydrocarbon contains the metal ion in the higher oxidation state in the range of 4-7M, the metal ion in the lower oxidation state in the range of 0.1-2M and sodium chloride in the range of 1-3M. The anode electrolyte may optionally contain 0.01-0.1M hydrochloric acid.

In some embodiments, the anode electrolyte may contain metal ion in the lower oxidation state and negligible or low amounts of the metal ion in the higher oxidation state for higher voltage efficiencies. The metal ion in the higher oxidation state may be supplemented to the exiting metal solution from the electrochemical cell before being fed into the reactor for the reaction with the hydrocarbon. Before the metal ion solution is circulated back to the electrochemical cell from the reactor, the metal ion in the higher oxidation state may be removed or separated and the solution predominantly containing the metal ion in the lower oxidation state may be fed to the electrochemical cell. Such separation and/or purification of the metal solution before and after the electrochemical cell have been described in detail below.

In some embodiments of the methods and systems described herein, the anode electrolyte may contain another cation in addition to the metal ion. Other cation includes, but is not limited to, alkaline metal ions and/or alkaline earth metal ions, such as but not limited to, lithium, sodium, calcium, magnesium, etc. The amount of the other cation added to the anode electrolyte may be between 0.01-5M; or between 0.01-1M; or between 0.05-1M; or between 0.5-2M; or between 1-5M.

In some embodiments of the methods and systems described herein, the anode electrolyte may contain an acid. The acid may be added to the anode electrolyte to bring the pH of the anolyte to 1 or 2 or less. The acid may be hydrochloric acid or sulfuric acid.

In some embodiments, the electrolyte in the electrochemical systems and methods described herein include the aqueous medium containing more than 5 wt % water. In some embodiments, the aqueous medium includes more than 5 wt % water; or more than 5.5 wt % water; or more than 6 wt %; or more than 20 wt % water; or more than 50 wt % water; or more than 80 wt % water; or more than 90 wt % water; or about 99 wt % water; or between 5-100 wt % water; or between 5-99 wt % water; or between 5-90 wt % water; or between 5-70 wt % water; or between 5-50 wt % water; or between 5-20 wt % water; or between 5-10 wt % water; or between 6-100 wt % water; or between 6-99 wt % water; or between 6-90 wt % water; or between 6-50 wt % water; or between 6-10 wt % water; or between 10-100 wt % water; or between 10-75 wt % water; or between 10-50 wt % water; or between 20-100 wt % water; or between 20-50 wt % water; or between 50-100 wt % water; or between 50-75 wt % water; or between 50-60 wt % water; or between 70-100 wt % water; or between 70-90 wt % water; or between 80-100 wt % water. In some embodiments, the aqueous medium may comprise a water soluble organic solvent.

In some embodiments of the methods and systems described herein, the amount of total metal ion in the anode electrolyte or the amount of copper in the anode electrolyte or the amount of iron in the anode electrolyte or the amount of chromium in the anode electrolyte or the amount of tin in the anode electrolyte or the amount of platinum or the amount of metal ion that is contacted with the unsaturated or saturated hydrocarbon is between 1-12M; or between 1-11M; or between 1-10M; or between 1-9M; or between 1-8M; or between 1-7M; or between 1-6M; or between 1-5M; or between 1-4M; or between 1-3M; or between 1-2M; or between 2-12M; or between 2-11M; or between 2-10M; or between 2-9M; or between 2-8M; or between 2-7M; or between 2-6M; or between 2-5M; or between 2-4M; or between 2-3M; or between 3-12M; or between 3-11M; or between 3-10M; or between 3-9M; or between 3-8M; or between 3-7M; or between 3-6M; or between 3-5M; or between 3-4M; or between 4-12M; or between 4-11M; or between 4-10M; or between 4-9M; or between 4-8M; or between 4-7M; or between 4-6M; or between 4-5M; or between 5-12M; or between 5-11M; or between 5-10M; or between 5-9M; or between 5-8M; or between 5-7M; or between 5-6M; or between 6-12M; or between 6-11M; or between 6-10M; or between 6-9M; or between 6-8M; or between 6-7M; or between 7-12M; or between 7-11M; or between 7-10M; or between 7-9M; or between 7-8M; or between 8-12M; or between 8-11M; or between 8-10M; or between 8-9M; or between 9-12M; or between 9-11M; or between 9-10M; or between 10-12M; or between 10-11M; or between 11-12M. In some embodiments, the amount of total ion in the anode electrolyte, as described above, is the amount of the metal ion in the lower oxidation state plus the amount of the metal ion in the higher oxidation state; or the total amount of the metal ion in the higher oxidation state; or the total amount of the metal ion in the lower oxidation state.

In some embodiments, in the electrochemical cell, the concentration of the metal ion in the lower oxidation state is between 0.5M to 2M or between 0.5M to 1M and the concentration of the metal ion in the higher oxidation state is between 4M to 5M. In some embodiments, in the reactor, the concentration of the metal ion in the lower oxidation state is between 0.5M to 2M or between 1M to 2M and the concentration of the metal ion in the higher oxidation state is between 4M to 5M. In some embodiments, in the electrochemical cell as well as in the reactor, the concentration of the metal ion in the lower oxidation state is between 0.5M to 2M and the concentration of the metal ion in the higher oxidation state is between 4M to 5M.

In some embodiments, the aqueous electrolyte including the catholyte or the cathode electrolyte and/or the anolyte or the anode electrolyte, or the third electrolyte disposed between AEM and CEM, in the systems and methods provided herein include, but not limited to, saltwater or fresh water. The saltwater includes, but is not limited to, seawater, brine, and/or brackish water. In some embodiments, the cathode electrolyte in the systems and methods provided herein include, but not limited to, seawater, freshwater, brine, brackish water, hydroxide, such as, sodium hydroxide, or combination thereof. Saltwater is employed in its conventional sense to refer to a number of different types of aqueous fluids other than fresh water, where the saltwater includes, but is not limited to, brackish water, sea water and brine (including, naturally occurring subterranean brines or anthropogenic subterranean brines and man-made brines, e.g., geothermal plant wastewaters, desalination waste waters, etc), as well as other salines having a salinity that is greater than that of freshwater. Brine is water saturated or nearly saturated with salt and has a salinity that is 50 ppt (parts per thousand) or greater. Brackish water is water that is saltier than fresh water, but not as salty as seawater, having a salinity ranging from 0.5 to 35 ppt. Seawater is water from a sea or ocean and has a salinity ranging from 35 to 50 ppt. The saltwater source may be a naturally occurring source, such as a sea, ocean, lake, swamp, estuary, lagoon, etc., or a man-made source. In some embodiments, the systems provided herein include the saltwater from terrestrial brine. In some embodiments, the depleted saltwater withdrawn from the electrochemical cells is replenished with salt and re-circulated back in the electrochemical cell.

In some embodiments, the electrolyte including the cathode electrolyte and/or the anode electrolyte and/or the third electrolyte, such as, saltwater includes water containing more than 1% chloride content, such as, NaCl; or more than 10% NaCl; or more than 50% NaCl; or more than 70% NaCl; or between 1-99% NaCl; or between 1-70% NaCl; or between 1-50% NaCl; or between 1-10% NaCl; or between 10-99% NaCl; or between 10-50% NaCl; or between 20-99% NaCl; or between 20-50% NaCl; or between 30-99% NaCl; or between 30-50% NaCl; or between 40-99% NaCl; or between 40-50% NaCl; or between 50-90% NaCl; or between 60-99% NaCl; or between 70-99% NaCl; or between 80-99% NaCl; or between 90-99% NaCl; or between 90-95% NaCl. In some embodiments, the above recited percentages apply to ammonium chloride, ferric chloride, sodium bromide, sodium iodide, or sodium sulfate as an electrolyte. The percentages recited herein include wt % or wt/wt % or wt/v %. It is to be understood that all the electrochemical systems described herein that contain sodium chloride can be replaced with other suitable electrolytes, such as, but not limited to, ammonium chloride, sodium bromide, sodium iodide, sodium sulfate, or combination thereof.

In some embodiments, the cathode electrolyte, such as, saltwater, fresh water, and/or sodium hydroxide do not include alkaline earth metal ions or divalent cations. As used herein, the divalent cations include alkaline earth metal ions, such as but not limited to, calcium, magnesium, barium, strontium, radium, etc. In some embodiments, the cathode electrolyte, such as, saltwater, fresh water, and/or sodium hydroxide include less than 1% w/w divalent cations. In some embodiments, the cathode electrolyte, such as, seawater, freshwater, brine, brackish water, and/or sodium hydroxide include less than 1% w/w divalent cations including, but not limited to, calcium, magnesium, and combination thereof.

In some embodiments, the anode electrolyte includes, but not limited to, fresh water and metal ions. In some embodiments, the anode electrolyte includes, but not limited to, saltwater and metal ions. In some embodiments, the anode electrolyte includes metal ion solution.

In some embodiments, the depleted saltwater from the cell may be circulated back to the cell. In some embodiments, the cathode electrolyte includes 1-90%; 1-50%; or 1-40%; or 1-30%; or 1-15%; or 1-20%; or 1-10%; or 5-90%; or 5-50%; or 5-40%; or 5-30%; or 5-20%; or 5-10%; or 10-90%; or 10-50%; or 10-40%; or 10-30%; or 10-20%; or 15-20%; or 15-30%; or 20-30%, of the sodium hydroxide solution. In some embodiments, the anode electrolyte includes 0-6 M; or 0-4.5M; or 0-4M; or 0-3.5M; or 0-3M; or 0-2.5M; or 0-2M; or 0-1.5M; or 0-1M; or 1-5M; or 1-4.5M; or 1-4M; or 1-3.5M; or 1-3M; or 1-2.5M; or 1-2M; or 1-1.5M; or 2-5M; or 2-4.5M; or 2-4M; or 2-3.5M; or 2-3M; or 2-2.5M; or 3-5M; or 3-4.5M; or 3-4M; or 3-3.5M; or 4-5M; or 4.5-6M metal ion solution. In some embodiments, the anode does not form an oxygen gas. In some embodiments, the anode does not form a chlorine gas.

In some embodiments, in the methods provided herein, the electrochemical cell may be conditioned with a first electrolyte and may be operated with a second electrolyte to prevent the fouling of the membranes with metal salts at low current densities. For example, in some embodiments, the electrochemical cell and the AEM, CEM or combination thereof are conditioned with a mix of sodium salt such as, but not limited to, sodium sulfate and ferrous salt such as, but not limited to, ferrous sulfate as the electrolyte and after the stabilization of the voltage with the mixed electrolyte, the cell may be operated with sodium chloride/metal chloride as the electrolyte. Applicants have surprisingly and unexpectedly found that the conditioning of the cell with sodium salt alone such as, but not limited to, sodium sulfate alone may result in the generation of oxygen gas which may be deleterious to the anode materials. However, the use of ferrous salt such as, but not limited to, ferrous sulfate in addition to sodium sulfate avoids the generation of the oxygen gas by preventing the water decomposition to oxygen and instead providing a redox reaction of ferrous to ferric ions. Additional advantages of using the mix of sodium sulfate and ferrous sulfate is that the cell voltage is low as compared to the cell voltage when oxygen evolves at the anode. Therefore, a low voltage rectifier can be used as opposed to high voltage rectifier needed when oxygen gas evolves. It is to be understood that other metal salts can be used in place of ferrous sulfate as long as the anodic potential with the metal salt is lower that the potential of the operated cell. It is also desirable that the metal salt does not foul the AEMs. Examples of such metal salts include, without limitation, stannous salt, any nitrite, any selenite, any sulfite, any chromite, any phosphite, ferrocyanide, or combinations thereof. The supporting electrolyte such as sodium sulfate can be any salt that is soluble in aqueous medium but does not take part in the anodic reaction. Examples of such salts include, but not limited to, chloride or sulfate salt of any alkaline or alkaline earth metal ion.

Accordingly, in some embodiments, there are provided methods that include contacting an anode with a first anode electrolyte in an anode chamber wherein the first electrolyte is a combination of two metal salts; conditioning the ion exchange membrane with the first anode electrolyte in the anode chamber; contacting the anode with a second anode electrolyte comprising a third metal ion; and oxidizing the third metal ion from a lower oxidation state to a higher oxidation state at the anode wherein the conditioning of the ion exchange membrane with the first electrolyte prevents the fouling of the membranes with the metal of the second electrolyte at low current densities. In some embodiments, the aforementioned method includes contacting a cathode with a cathode electrolyte in a cathode chamber and separating the cathode and the anode by at least one ion exchange membrane. In some embodiments, the aforementioned method and embodiments include forming an alkali, water, and/or hydrogen gas at the cathode. In some embodiments, the aforementioned method and embodiments include first anode electrolyte comprising a combination of two metal salts which is sodium salt mixed with ferrous salt; the second anode electrolyte which is sodium chloride; and the third metal ion in the second electrolyte is copper. In some embodiments, the method further comprises contacting the second anode electrolyte comprising the metal ion in the higher oxidation state with an unsaturated and/or saturated hydrocarbon to form halogenated hydrocarbon. In some embodiments, the ion exchange membrane is a cation exchange membrane (CEM), an anion exchange membrane (AEM); or combination thereof.

Depending on the degree of alkalinity desired in the cathode electrolyte, the pH of the cathode electrolyte may be adjusted and in some embodiments is maintained between 6 and 12; or between 7 and 14 or greater; or between 7 and 13; or between 7 and 12; or between 7 and 11; or between 10 and 14 or greater; or between 10 and 13; or between 10 and 12; or between 10 and 11. In some embodiments, the pH of the cathode electrolyte may be adjusted to any value between 7 and 14 or greater, a pH less than 12, a pH 7.0, 7.5, 8.0, 8.5, 9.0, 9.5, 10.0, 10.5, 11.0, 11.5, 12.0, 12.5, 13.0, 13.5, 14.0, and/or greater.

Similarly, in some embodiments of the system, the pH of the anode electrolyte is adjusted and is maintained between 0-7; or between 0-6; or between 0-5; or between 0-4; or between 0-3; or between 0-2; or between 0-1. As the voltage across the anode and cathode may be dependent on several factors including the difference in pH between the anode electrolyte and the cathode electrolyte (as can be determined by the Nernst equation well known in the art), in some embodiments, the pH of the anode electrolyte may be adjusted to a value between 0 and 7, including 0, 0.5, 1.0, 1.5, 2.0, 2.5, 3.0, 3.5, 4.0, 4.5, 5.0, 5.5, 6.0, 6.5 and 7, depending on the desired operating voltage across the anode and cathode. Thus, in equivalent systems, where it is desired to reduce the energy used and/or the voltage across the anode and cathode, e.g., as in the chlor-alkali process, the carbon dioxide or a solution containing dissolved carbon dioxide can be added to the cathode electrolyte to achieve a desired pH difference between the anode electrolyte and cathode electrolyte.

The system may be configured to produce any desired pH difference between the anode electrolyte and the cathode electrolyte by modulating the pH of the anode electrolyte, the pH of the cathode electrolyte, the concentration of hydroxide in the cathode electrolyte, the withdrawal and replenishment of the anode electrolyte, and/or the withdrawal and replenishment of the cathode electrolyte. By modulating the pH difference between the anode electrolyte and the cathode electrolyte, the voltage across the anode and the cathode can be modulated. In some embodiments, the system is configured to produce a pH difference of at least 4 pH units; at least 5 pH units; at least 6 pH units; at least 7 pH units; at least 8 pH units; at least 9 pH units; or between 4-12 pH units; or between 4-9 pH units; or between 3-12 pH units; or between 3-9 pH units; or between 5-12 pH units; or between 5-9 pH units; or between 6-12 pH units; or between 6-9 pH units; or between 7-12 pH units; or between 7-9 pH units; or between 8-12 pH units; or between 8-9 pH units; between the anode electrolyte and the cathode electrolyte. In some embodiments, the system is configured to produce a pH difference of at least 4 pH units between the anode electrolyte and the cathode electrolyte.

In some embodiments, the anode electrolyte and the cathode electrolyte in the electrochemical cell, in the methods and systems provided herein, are operated at room temperature or at elevated temperatures, such as, e.g., at more than 40° C., or more than 50° C., or more than 60° C., or more than 70° C., or more than 80° C., or more, or between 30-70° C., or between 70-150° C.

In some embodiments, the systems provided herein result in low to zero voltage systems that generate alkali as compared to chlor-alkali process or chlor-alkali process with ODC or any other process that oxidizes metal ions from lower oxidation state to the higher oxidation state in the anode chamber. In some embodiments, the systems described herein run at voltage of less than 2.5V; or less than 2V; or less than 1.2V; or less than 1.1V; or less than 1V; or less than 0.9V; or less than 0.8V; or less than 0.7V; or less than 0.6V; or less than 0.5V; or less than 0.4V; or less than 0.3V; or less than 0.2V; or less than 0.1V; or at zero volts; or between 0-1.2V; or between 0-1V; or between 0-0.5 V; or between 0.5-1V; or between 0.5-2V; or between 0-0.1 V; or between 0.1-1V; or between 0.1-2V; or between 0.01-0.5V; or between 0.01-1.2V; or between 1-1.2V; or between 0.2-1V; or 0V; or 0.5V; or 0.6V; or 0.7V; or 0.8V; or 0.9V; or 1V.

As used herein, the "voltage" includes a voltage or a bias applied to or drawn from an electrochemical cell that drives a desired reaction between the anode and the cathode in the electrochemical cell. In some embodiments, the desired reaction may be the electron transfer between the anode and the cathode such that an alkaline solution, water, or hydrogen gas is formed in the cathode electrolyte and the metal ion is oxidized at the anode. In some embodiments, the desired reaction may be the electron transfer between the anode and the cathode such that the metal ion in the higher oxidation state is formed in the anode electrolyte from the metal ion in the lower oxidation state. The voltage may be applied to the electrochemical cell by any means for applying the current across the anode and the cathode of the electrochemical cell. Such means are well known in the art and include, without limitation, devices, such as, electrical power source, fuel cell, device powered by sun light, device powered by wind, and combination thereof. The type of electrical power source to provide the current can be any power source known to one skilled in the art. For example, in some embodiments, the voltage may be applied by connecting the anodes and the cathodes of the cell to an external direct current (DC) power source. The power source can be an alternating current (AC) rectified into DC. The DC power source may have an adjustable voltage and current to apply a requisite amount of the voltage to the electrochemical cell.

In some embodiments, the current applied to the electrochemical cell is at least 50 mA/cm$^2$; or at least 100 mA/cm$^2$; or at least 150 mA/cm$^2$; or at least 200 mA/cm$^2$; or at least 500 mA/cm$^2$; or at least 1000 mA/cm$^2$; or at least 1500 mA/cm$^2$; or at least 2000 mA/cm$^2$; or at least 2500 mA/cm$^2$; or between 100-2500 mA/cm$^2$; or between 100-2000 mA/cm$^2$; or between 100-1500 mA/cm$^2$; or between 100-1000 mA/cm$^2$; or between 100-500 mA/cm$^2$; or between 200-2500 mA/cm$^2$; or between 200-2000 mA/cm$^2$; or between 200-1500 mA/cm$^2$; or between 200-1000 mA/cm$^2$; or between 200-500 mA/cm$^2$; or between 500-2500 mA/cm$^2$; or between 500-2000 mA/cm$^2$; or between 500-1500 mA/cm$^2$; or between 500-1000 mA/cm$^2$; or between 1000-2500 mA/cm$^2$; or between 1000-2000 mA/cm$^2$; or between 1000-1500 mA/cm$^2$; or between 1500-2500 mA/cm$^2$; or between 1500-2000 mA/cm$^2$; or between 2000-2500 mA/cm$^2$.

In some embodiments, the cell runs at voltage of between 0-3V when the applied current is 100-250 mA/cm$^2$ or 100-150 mA/cm$^2$ or 100-200 mA/cm$^2$ or 100-300 mA/cm$^2$ or 100-400 mA/cm$^2$ or 100-500 mA/cm$^2$ or 150-200 mA/cm$^2$ or 200-150 mA/cm$^2$ or 200-300 mA/cm$^2$ or 200-400 mA/cm$^2$ or 200-500 mA/cm$^2$ or 150 mA/cm$^2$ or 200 mA/cm$^2$ or 300 mA/cm$^2$ or 400 mA/cm$^2$ or 500 mA/cm$^2$ or 600 mA/cm$^2$. In some embodiments, the cell runs at between 0-1V. In some embodiments, the cell runs at between 0-1.5V when the applied current is 100-250 mA/cm$^2$ or 100-150 mA/cm$^2$ or 150-200 mA/cm$^2$ or 150 mA/cm$^2$ or 200 mA/cm$^2$. In some embodiments, the cell runs at between 0-1V at an amperic load of 100-250 mA/cm$^2$ or 100-150 mA/cm$^2$ or 150-200 mA/cm$^2$ or 150 mA/cm$^2$ or 200 mA/cm$^2$. In some embodiments, the cell runs at 0.5V at a current or an amperic load of 100-250 mA/cm$^2$ or 100-150 mA/cm$^2$ or 150-200 mA/cm$^2$ or 150 mA/cm$^2$ or 200 mA/cm$^2$.

In some embodiments, the systems and methods provided herein further include a percolator and/or a spacer between the anode and the ion exchange membrane and/or the cathode and the ion exchange membrane. The electrochemical systems containing percolator and/or spacers are described in U.S. Provisional Application No. 61/442,573, filed Feb. 14, 2011, which is incorporated herein by reference in its entirety in the present disclosure.

The systems provided herein are applicable to or can be used for any of one or more methods described herein. In some embodiments, the systems provided herein further include an oxygen gas supply or delivery system operably connected to the cathode chamber. The oxygen gas delivery system is configured to provide oxygen gas to the gas-diffusion cathode. In some embodiments, the oxygen gas delivery system is configured to deliver gas to the gas-diffusion cathode where reduction of the gas is catalyzed to hydroxide ions. In some embodiments, the oxygen gas and water are reduced to hydroxide ions; un-reacted oxygen gas in the system is recovered; and re-circulated to the cathode. The oxygen gas may be supplied to the cathode using any means for directing the oxygen gas from the external source to the cathode. Such means for directing the oxygen gas from the external source to the cathode or the oxygen gas delivery system are well known in the art and include, but not limited to, pipe, duct, conduit, and the like. In some embodiments, the system or the oxygen gas delivery system includes a duct that directs the oxygen gas from the external source to the cathode. It is to be understood that the oxygen gas may be directed to the cathode from the bottom of the cell, top of the cell or sideways. In some embodiments, the oxygen gas is directed to the back side of the cathode where the oxygen gas is not in direct contact with the catholyte. In some embodiments, the oxygen gas may be directed to the cathode through multiple entry ports. The source of oxygen that provides oxygen gas to the gas-diffusion cathode, in the methods and systems provided herein, includes any source of oxygen known in the art. Such sources include, without limitation, ambient air, commercial grade oxygen gas from cylinders, oxygen gas obtained by fractional distillation of liquefied air, oxygen gas obtained by passing air through a bed of zeolites, oxygen gas obtained from electrolysis of water, oxygen obtained by forcing air through ceramic membranes based on zirconium dioxides by either high pressure or electric current, chemical oxygen generators, oxygen gas as a liquid in insulated tankers, or combination thereof. In some embodiments, the source of oxygen may also provide carbon dioxide gas. In some embodiments, the oxygen from the source of oxygen gas may be purified before being administered to the cathode chamber. In some embodiments, the oxygen from the source of oxygen gas is used as is in the cathode chamber.

Reaction with Unsaturated Hydrocarbon or Saturated Hydrocarbon

In some embodiments, the metal formed with a higher oxidation state in the anode electrolyte of the electrochemical systems of FIG. 1A, 1B, 2, 4A, or 4B may be reacted with saturated or unsaturated hydrocarbons to from corresponding halohydrocarbons or sulfohydrocarbons based on the anion attached to the metal. For example, the metal chloride, metal bromide, metal iodide, or metal sulfate etc. may result in corresponding chlorohydrocarbons, bromohydrocarbons, iodohydrocarbons, or sulfohydrocarbons, after the reaction of the unsaturated hydrocarbons with the metal halide or metal sulfate. In some embodiments, the reaction of the metal halide or metal sulfate with the unsaturated hydrocarbons results in the generation of the above described products as well as the metal halide or metal sulfate in the lower oxidation state. The metal ion in the lower oxidation state may then be re-circulated back to the electrochemical system for the generation of the metal ion in the higher oxidation state. The separation and purification of the metal ion before being circulated back to the electrochemical cell are described herein below.

The "halohydrocarbon" or "halogenated hydrocarbon" as used herein, includes halo substituted hydrocarbons where halo may be any number of halogens that can be attached to the hydrocarbon based on permissible valency. The halogens include fluoro, chloro, bromo, and iodo. The examples of halohydrocarbons include chlorohydrocarbons, bromohydrocarbons, and iodohydrocarbons. The chlorohydrocarbons include, but not limited to, monochlorohydrocarbons, dichlorohydrocarbons, trichlorohydrocarbons, etc. For metal halides, such as, but not limited to, metal chloride, metal bromide and metal iodide, the metal chloride, metal bromide or metal iodide with the higher oxidation state produced by the anode chamber can be used for other purposes, such as, but not limited to, generation of chloro, bromo or iodohydrocarbons, such as, but not limited to, monochlorohydrocarbons, dichlorohydrocarbons, trichlorohydrocarbons, monobromohydrocarbons, dibromohydrocarbons, tribromohydrocarbons, monoiodohydrocarbons, diiodohydrocarbons, triiodohydrocarbons, etc. The hydrocarbon in the halo or sulfo hydrocarbon is any hydrocarbon from which the halo or sulfo hydrocarbon is generated. For example, EDC is the halogenated hydrocarbon generated from ethylene by addition of chlorine atoms on the double bond or EDC is the halogenated hydrocarbon generated from ethane by replacement of the hydrogens by the chlorine atoms.

The "sulfohydrocarbons" as used herein include hydrocarbons substituted with one or more of —$SO_3H$ or —$OSO_2OH$ based on permissible valency.

The "unsaturated hydrocarbon" as used herein, includes a hydrocarbon with unsaturated carbon or hydrocarbon with at least one double and/or at least one triple bond between adjacent carbon atoms. The unsaturated hydrocarbon may be linear, branched, or cyclic (aromatic or non-aromatic). For example, the hydrocarbon may be olefinic, acetylenic, non-aromatic such as cyclohexene, aromatic group or a substituted unsaturated hydrocarbon such as, but not limited to, halogenated unsaturated hydrocarbon. The hydrocarbons with at least one double bond may be called olefins or alkenes and may have a general formula of an unsubstituted alkene as $C_nH_{2n}$ where n is 2-20 or 2-10 or 2-8, or 2-5. In some embodiments, one or more hydrogens on the alkene may be further substituted with other functional groups such as but not limited to, halogen (including chloro, bromo, iodo, and fluoro), carboxylic acid (—COOH), hydroxyl (—OH), amines, etc. The unsaturated hydrocarbons include all the isomeric forms of unsaturation, such as, but not limited to, cis and trans isomers, E and Z isomers, positional isomers etc.

Examples of substituted or unsubstituted alkenes include, but not limited to, ethylene, chloro ethylene, bromo ethylene, iodo ethylene, propylene, chloro propylene, hydroxyl propylene, 1-butylene, 2-butylene (cis or trans), isobutylene, 1,3-butadiene, pentylene, hexene, cyclopropylene, cyclobutylene, cyclohexene, etc.

The hydrocarbons with at least one triple bond maybe called alkynes and may have a general formula of an unsubstituted alkyne as $C_nH_{2n+2}$ where n is 2-10 or 2-8, or 2-5. In some embodiments, one or more hydrogens on the alkyne may be further substituted with other functional groups such as but not limited to, halogen, carboxylic acid, hydroxyl, etc. Examples of substituted or unsubstituted alkynes include, but not limited to, acetylene, propyne, chloro propyne, bromo propyne, butyne, pentyne, hexyne, etc.

In some embodiments, the unsaturated hydrocarbon in the aforementioned method and system embodiments and as described herein is C2-C10 alkene or C2-C8 alkene or C2-C6 alkene or C2-C5 alkene or C2-C4 alkene or C2-C3 alkene. In some embodiments, the unsaturated hydrocarbon in the aforementioned method and system embodiments and as described herein is C2-C10 alkyne or C2-C8 alkyne or C2-C6 alkyne or C2-C5 alkyne or C2-C4 alkyne or C2-C3 alkyne. In some embodiments of the methods and systems described herein, the unsaturated hydrocarbon described herein is, ethylene. The halohydrocarbon formed from such unsaturated hydrocarbon is e.g., ethylene dichloride (EDC), chloroethanol, butyl chloride, dichlorobutane, chlorobutanol, etc.

In some method and system embodiments, the anode does not produce chlorine gas. In some method and system embodiments, the treatment of the unsaturated hydrocarbon with the metal ion in the higher oxidation state does not require oxygen gas and/or chlorine gas. In some method and system embodiments, the anode does not produce chlorine gas and the treatment of the unsaturated hydrocarbon with the metal ion in the higher oxidation state does not require oxygen gas and/or chlorine gas.

Figure 6:
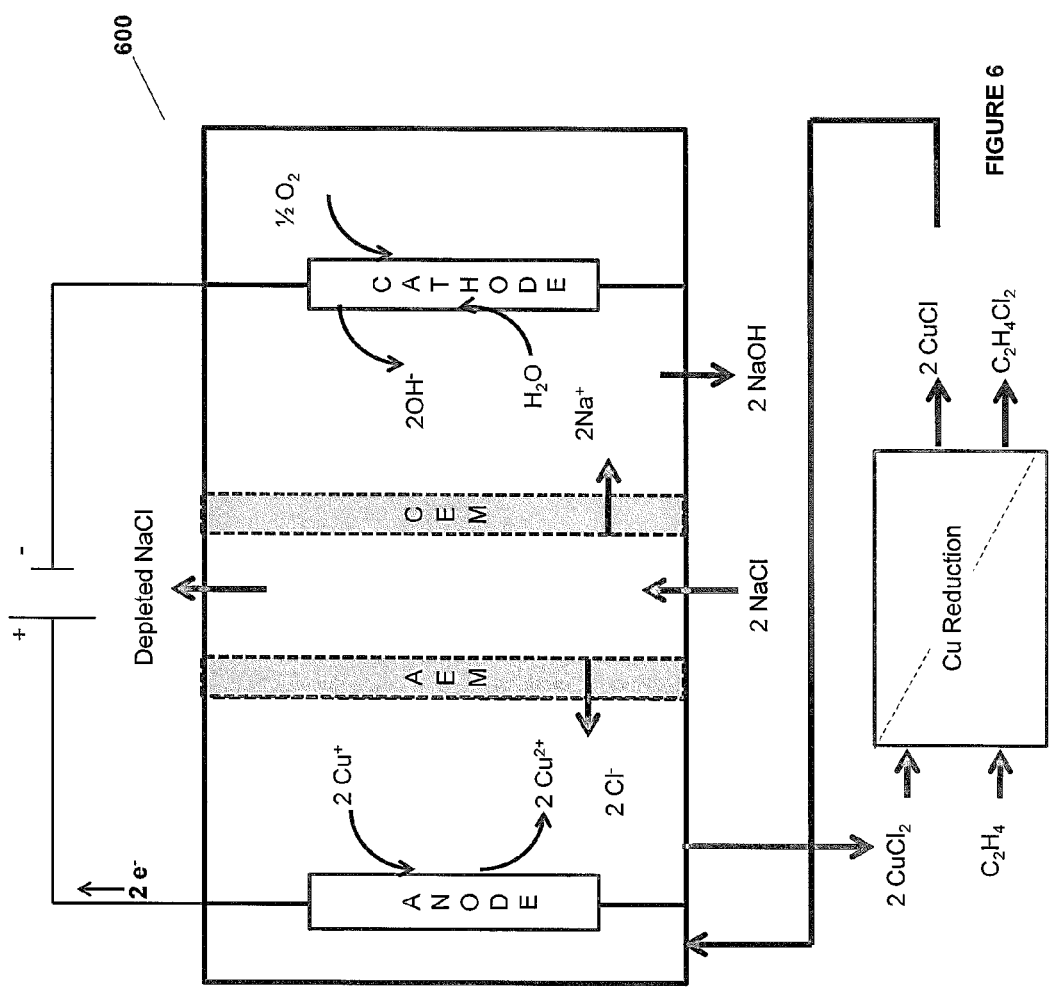
FIG. 6 is an illustration of some embodiments provided herein.

An example of the electrochemical system of FIG. 2, is as illustrated in FIG. 6. It is to be understood that the system 600 of FIG. 6 is for illustration purposes only and other metal ions with different oxidations states, other unsaturated hydrocarbons, and other electrochemical systems forming products other than alkali, such as water or hydrogen gas in the cathode chamber, are equally applicable to the system. In some embodiments, as illustrated in FIG. 6, the electrochemical system 600 includes an oxygen depolarized cathode that produces hydroxide ions from water and oxygen. The system 600 also includes an anode that converts metal ions from 1+ oxidation state to 2+ oxidation state. The $Cu^{2+}$ ions combine with chloride ions to form $CuCl_2$. The metal chloride $CuCl_2$ can be then reacted with an unsaturated hydrocarbon, such as, but not limited to, ethylene to undergo reduction of the metal ion to lower oxidation state to form CuCl and dichlorohydrocarbon, such as, but not limited to, ethylene dichloride. The CuCl is then re-circulated back to the anode chamber for conversion to $CuCl_2$. It is to be understood, as described herein, the anode electrolyte comprising the $CuCl_2$ entering the reactor, may also contain CuCl and the metal solution comprising CuCl exiting the reactor after reaction with ethylene, may also contain $CuCl_2$.

The ethylene dichloride formed by the methods and systems of the invention can be used for any commercial purposes. In some embodiments, the ethylene dichloride is subjected to vinyl chloride monomer (VCM) formation through the process such as cracking/purification. The vinyl chloride monomer may be used in the production of polyvinylchloride. In some embodiments, the hydrochloric acid formed during the conversion of EDC to VCM may be separated and reacted with acetylene to further form VCM. In some embodiments, the HCl generated in the process of VCM formation may be circulated to one or more of the electrochemical systems described herein where HCl is used in the cathode or anode electrolyte to form hydrogen gas or water at the cathode.

In some embodiments, the chlorination of ethylene in an aqueous medium with metal chloride in the higher oxidation state, results in ethylene dichloride, chloroethanol, or combination thereof. In some embodiments of the methods and systems described herein, there is a formation of more than 10 wt %; or more than 20 wt %, or more than 30 wt %, or more than 40 wt %, or more than 50 wt %, or more than 60 wt %, or more than 70 wt %, or more than 80 wt %, or more than 90 wt %, or more than 95 wt %, or about 99 wt %, or between about 10-99 wt %, or between about 10-95 wt %, or between about 15-95 wt %, or between about 25-95 wt %, or between about 50-95 wt %, or between about 50-99 wt %, or between about 50-99.9 wt %, or between about 50-99.99 wt % ethylene dichloride, from ethylene. In some embodiments, the remaining weight percentage may be of chloroethanol optionally also containing other minor side products. In some embodiments, no chloroethanol is formed in the reaction. In some embodiments, less than 0.001 wt % or less than 0.01 wt % or less than 0.1 wt % or less than 0.5 wt % or less than 1 wt % or less than 5 wt % or less than 10 wt % or less than 20 wt % of chloroethanol is formed with the remaining EDC in the reaction (may also contain other minor side products). In some embodiments, less than 0.001 wt % or less than 0.01 wt % or less than 0.1 wt % or less than 0.5 wt % or less than 1 wt % or less than 5 wt % of metal ion is present in EDC product. In some embodiments, less than 0.001 wt % or less than 0.01 wt % or less than 0.1 wt % of chloroethanol and/or metal ion is present in the EDC product. Other side products may also be formed as described herein.

Figure 9A:
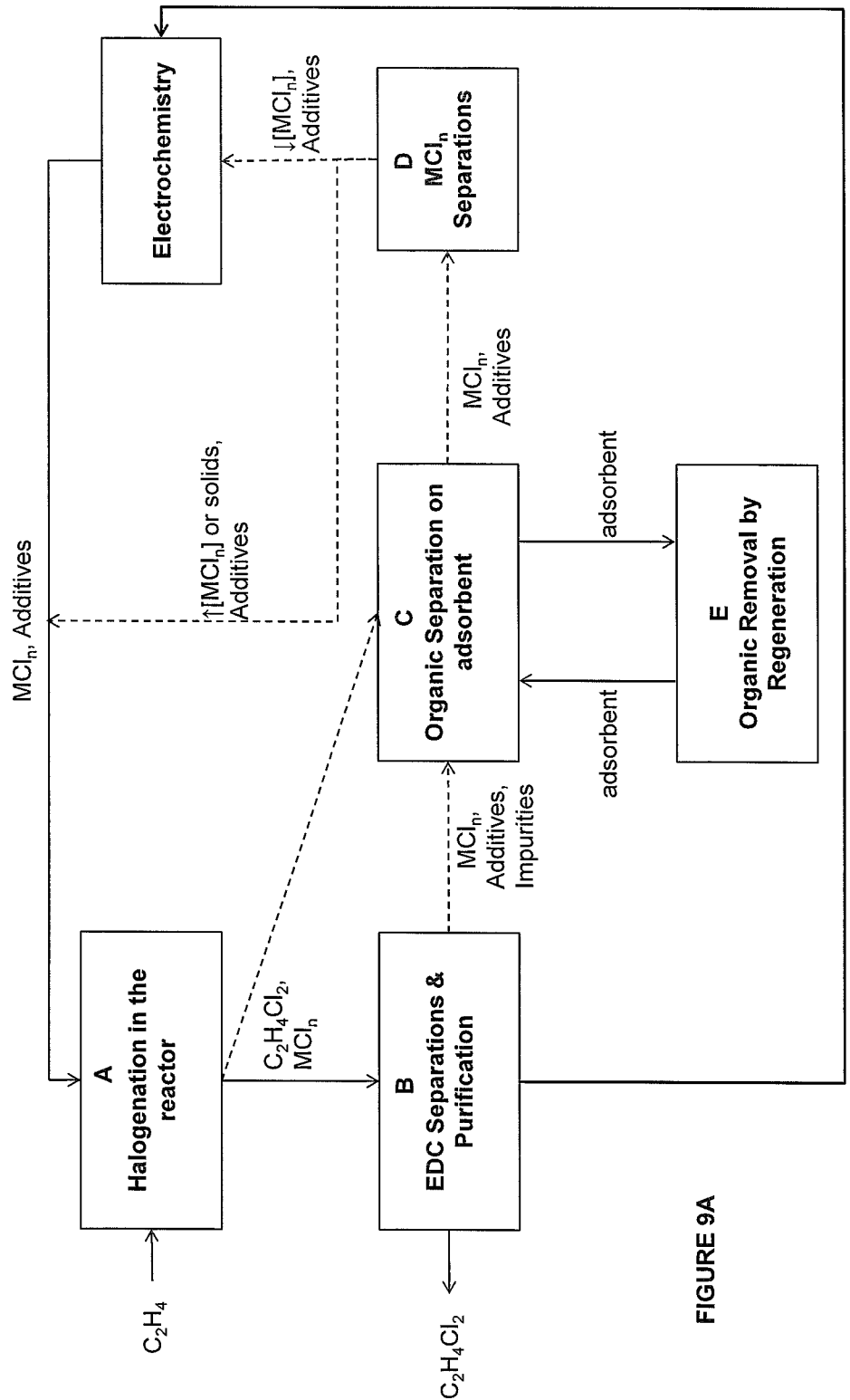
FIG. 9A is an illustration of some embodiments provided herein.
Figure 9B:
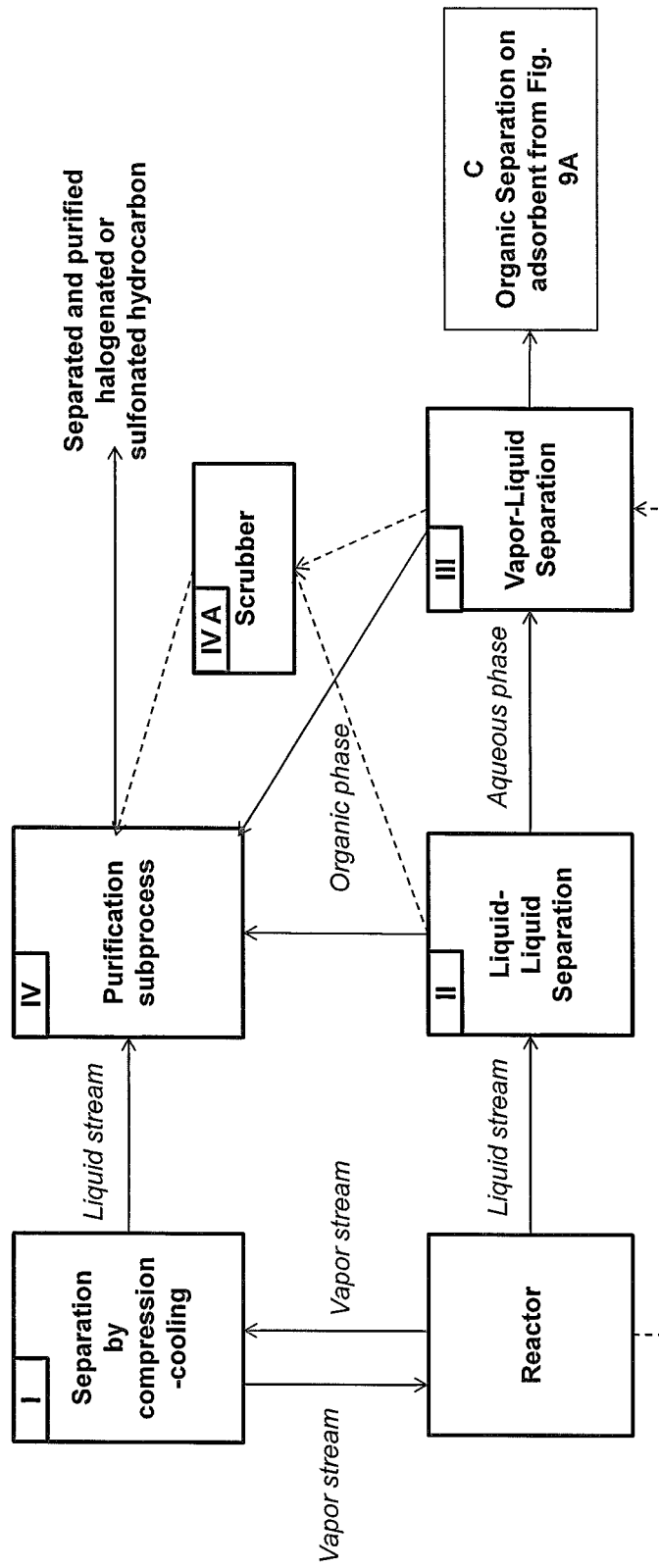
FIG. 9B is an illustration of some embodiments provided herein.
Figure 9C:
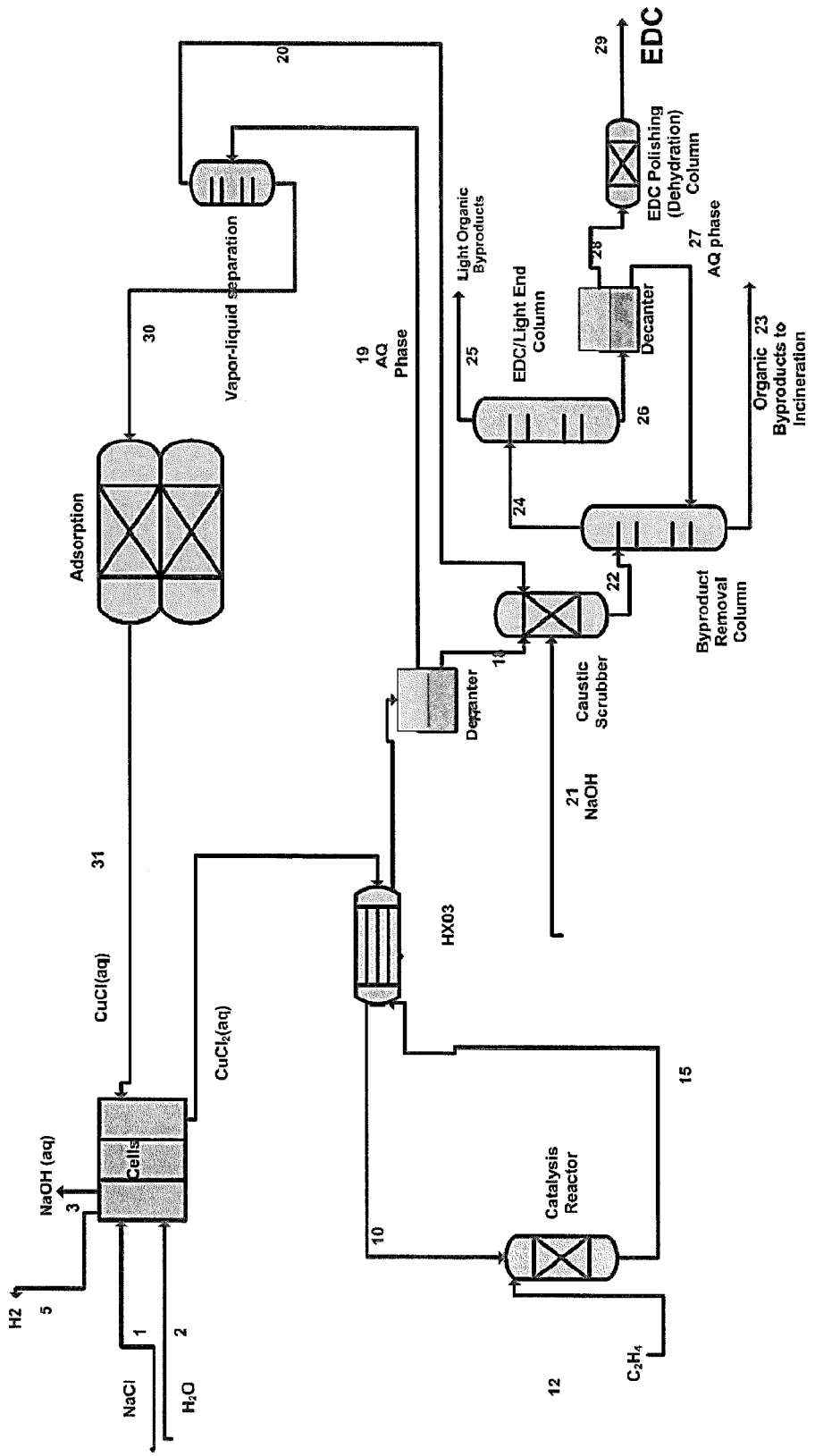
FIG. 9C is an illustration of some embodiments provided herein.

In some embodiments, the EDC product containing the metal ion may be subjected to washing step which may include rinsing with an organic solvent or passing the EDC product through a column to remove the metal ions. In some embodiments, the EDC product may be purified by distillation where any of the side products such as 1,1,2-trichloroethane, 1,1,2,2-tetrachloroethane, pentachloroethane, 1,1-dichloroethene, trichloroethylene, tetrachloroethene, chloral ($CCl_3CHO$) and/or chloral hydrate (2,2,2-trichloroethane-1,1-diol), if formed, may be separated. The separation and purification of the organic product is described and is illustrated in FIGS. 9A, 9B, and 9C as described below.

In some embodiments, the unsaturated hydrocarbon is C3 alkene such as, propene. In some embodiments, the metal ion in the higher oxidation state such as $CuCl_2$ is treated with propene to result in propane dichloride ($C_3H_6Cl_2$) or dichloropropane (DCP) which can be used to make allyl chloride ($C_3H_5Cl$). In some embodiments, the unsaturated hydrocarbon is C4 alkene such as, butene or butylene. In some embodiments, the metal ion in the higher oxidation state such as $CuCl_2$ is treated with butene to result in butane dichloride ($C_4H_8Cl_2$) or dichlorobutene ($C_4H_6Cl_2$) which can be used to make chloroprene ($C_4H_5Cl$). In some embodiments, the unsaturated hydrocarbon is C5 alkene such as, pentene or C6 alkene such as, hexene resulting in corresponding halo products. In some embodiments, the unsaturated hydrocarbon is aromatic such as, benzene. In some embodiments, the metal ion in the higher oxidation state such as $CuCl_2$ is treated with benzene to result in chlorobenzene. In some embodiments, the metal ion in the higher oxidation state such as $CuCl_2$ is treated with C2 alkyne, such as, acetylene to result in chloroacetylene, dichloroacetylene, vinyl chloride, dichloroethene, tetrachloroethene, or combination thereof. In some embodiments, a suitable unsaturated hydrocarbon is treated with metal chloride in higher oxidation state to form a product including, but not limited to, ethylene dichloride, chloroethanol, chloropropene, propylene oxide (further dehydrochlorinated), allyl chloride, methyl chloride, trichloroethylene, tetrachloroethene, chlorobenzene, 1,2-dichloroethane, 1,1,2-trichloroethane, 1,1,2,2-tetrachloroethane, pentachloroethane, 1,1-dichloroethene, chlorophenol, chlorinated toluene, etc.

In some embodiments, the yield of the halogenated hydrocarbon from unsaturated hydrocarbon (e.g. using the reactor described herein), e.g. the yield of EDC from ethylene or yield of DCP from propylene, or dichlorobutene from butene, using the metal ions is more than 90% or more than 95% or between 90-95% or between 90-99% or between 90-99.9% by weight. In some embodiments, the selectivity of the halogenated hydrocarbon from unsaturated hydrocarbon, e.g. the selectivity of EDC from ethylene or selectivity of DCP from propylene, or dichlorobutene from butene, using the metal ions is more than 80% or more than 90% or between 80-99% by weight. In some embodiments, the STY (space time yield) of the halogenated hydrocarbon from unsaturated hydrocarbon, e.g. the STY of EDC from ethylene or STY of DCP from propylene, or dichlorobutene from butene, etc. using the metal ions is more than 0.1, or more than 0.5, or is 1, or more than 1, or more than 2, or more than 3, or more than 4, or more than 5, or between 0.1-3, or between 0.5-3, or between 0.5-2, or between 0.5-1, or between 3-5, or between 3-6, or between 3-8. As used herein the STY is yield per time unit per reactor volume. For example, the yield of product may be expressed in mol, the time unit in hour and the volume in liter (e.g. see Example 9). The volume may be the nominal volume of the reactor, e.g. in a packed bed reactor, the volume of the vessel that holds the packed bed is the volume of the reactor. The STY may also be expressed as STY based on the consumption of the unsaturated or saturated hydrocarbon consumed to form the product. For example only, in some embodiments, the STY of the ethylene dichloride product may be deduced from the amount of ethylene consumed during the reaction (e.g. see Example 10). The selectivity may be the mol of product/mol of the unsaturated or saturated hydrocarbon consumed (e.g. only, mol EDC made/mol ethylene consumed). The yield may be the amount of the product isolated. The purity may be the amount of the product/total amount of all products (e.g. only, amount of EDC/all the organic products formed).

In some embodiments, the metal formed with a higher oxidation state in the anode electrolyte of the electrochemical systems may be reacted with saturated hydrocarbons to from corresponding halohydrocarbons or sulfohydrocarbons based on the anion attached to the metal. For example, the metal chloride, metal bromide, metal iodide, or metal sulfate etc. may result in corresponding chlorohydrocarbons, bromohydrocarbons, iodohydrocarbons, or sulfohydrocarbons, after the reaction of the saturated hydrocarbons with the metal halide or metal sulfate. In some embodiments, the reaction of metal halide or metal sulfate with the saturated hydrocarbons results in the generation of the products as well as the metal halide or metal sulfate in the lower oxidation state. The metal ion in the lower oxidation state may then be re-circulated back to the electrochemical system for the generation of the metal ion in the higher oxidation state.

The "saturated hydrocarbon" as used herein, includes a hydrocarbon with no unsaturated carbon or hydrocarbon. The hydrocarbon may be linear, branched, or cyclic. For example, the hydrocarbon may be substituted or unsubstituted alkanes and/or substituted or unsubstituted cycloalkanes. The hydrocarbons may have a general formula of an unsubstituted alkane as $C_nH_{2n+2}$ where n is 2-20 or 2-10 or 2-8, or 2-5. In some embodiments, one or more hydrogens on the alkane or the cycloalkanes may be further substituted with other functional groups such as but not limited to, halogen (including chloro, bromo, iodo, and fluoro), carboxylic acid (—COOH), hydroxyl (—OH), amines, etc.

Examples of substituted or unsubstituted alkanes $C_nH_{2n+2}$ where n is 2-20 or 2-10 or 2-8, or 2-6 or 2-5 include, but not limited to, methane, ethane, chloroethane, bromoethane, iodoethane, propane, chloropropane, hydroxypropane, butane, chlorobutane, hydroxybutane, pentane, hexane, cyclohexane, cyclopentane, chlorocyclopentane, octane, decane, etc.

It is to be understood that the example of the electrochemical system illustrated in FIG. 6 can be configured for saturated hydrocarbons by replacing the unsaturated hydrocarbon with a saturated hydrocarbon. Accordingly, suitable metal ions may be used such as platinum chloride, palladium chloride, copper chloride etc.

In some embodiments, the chlorination of ethane in an aqueous medium with metal chloride in the higher oxidation state, results in ethane chloride, ethane dichloride, or combination thereof. In some embodiments of the methods and systems described herein, there is a formation of more than 10 wt %; or more than 20 wt %, or more than 30 wt %, or more than 40 wt %, or more than 50 wt %, or more than 60 wt %, or more than 70 wt %, or more than 80 wt %, or more than 90 wt %, or more than 95 wt %, or about 99 wt %, or between about 10-99 wt %, or between about 10-95 wt %, or between about 15-95 wt %, or between about 25-95 wt %, or between about 50-95 wt %, or between about 50-99 wt %, or between about 50-99.9 wt %, or between about 50-99.99 wt % chloroethane (ethane chloride), from ethane. In some embodiments, the remaining weight percentage is of chloroethanol and/or ethylene dichloride optionally including other minor side products. In some embodiments, no chloroethanol is formed in the reaction. In some embodiments, less than 0.001 wt % or less than 0.01 wt % or less than 0.1 wt % or less than 0.5 wt % or less than 1 wt % or less than 5 wt % or less than 10 wt % or less than 20 wt % of chloroethanol is formed with the remaining product in the reaction. In some embodiments, less than 0.001 wt % or less than 0.01 wt % or less than 0.1 wt % or less than 0.5 wt % or less than 1 wt % or less than 5 wt % of metal ion is present in the product. In some embodiments, less than 0.001 wt % or less than 0.01 wt % or less than 0.1 wt % of chloroethanol and/or metal ion is present in the product.

In some embodiments, the yield of the halogenated hydrocarbon from saturated hydrocarbon, e.g. the yield of chloroethane or EDC from ethane, using the metal ions is more than 90% or more than 95% or between 90-95% or between 90-99% or between 90-99.9% by weight. In some embodiments, the selectivity of the halogenated hydrocarbon from saturated hydrocarbon, e.g. the yield of chloroethane or EDC from ethane, using the metal ions is more than 80% or more than 90% or between 80-99% by weight. In some embodiments, the STY (space time yield) of the halogenated hydrocarbon from saturated hydrocarbon is more than 0.1, or 1, or more than 0.5, or more than 1, or more than 2, or more than 3, or more than 4, or more than 5, or between 0.1-3, or between 0.5-3, or between 0.5-2, or between 0.5-1, or between 3-5 or between 3-6 or between 3-8.

The systems provided herein include a reactor operably connected to the anode chamber that carries out the halogenations or sulfonation reactions. The "reactor" as used herein is any vessel or unit in which the halogenation or sulfonation reaction provided herein is carried out. The reactor is configured to contact the metal chloride or metal sulfate in the anode electrolyte with the unsaturated or saturated hydrocarbon. The reactor may be any means for contacting the metal chloride or metal sulfate in the anode electrolyte with the unsaturated or saturated hydrocarbon. Such means or such reactor are well known in the art and include, but not limited to, pipe, column, duct, tank, series of tanks, container, tower, conduit, and the like. Some examples of such reactors are described in FIGS. 7 and 8 herein. The configuration of the reactor is also described herein below. The reactor may be equipped with one or more of controllers to control temperature sensor, pressure sensor, control mechanisms, inert gas injector, etc. to monitor, control, and/or facilitate the reaction.

Figure 7:
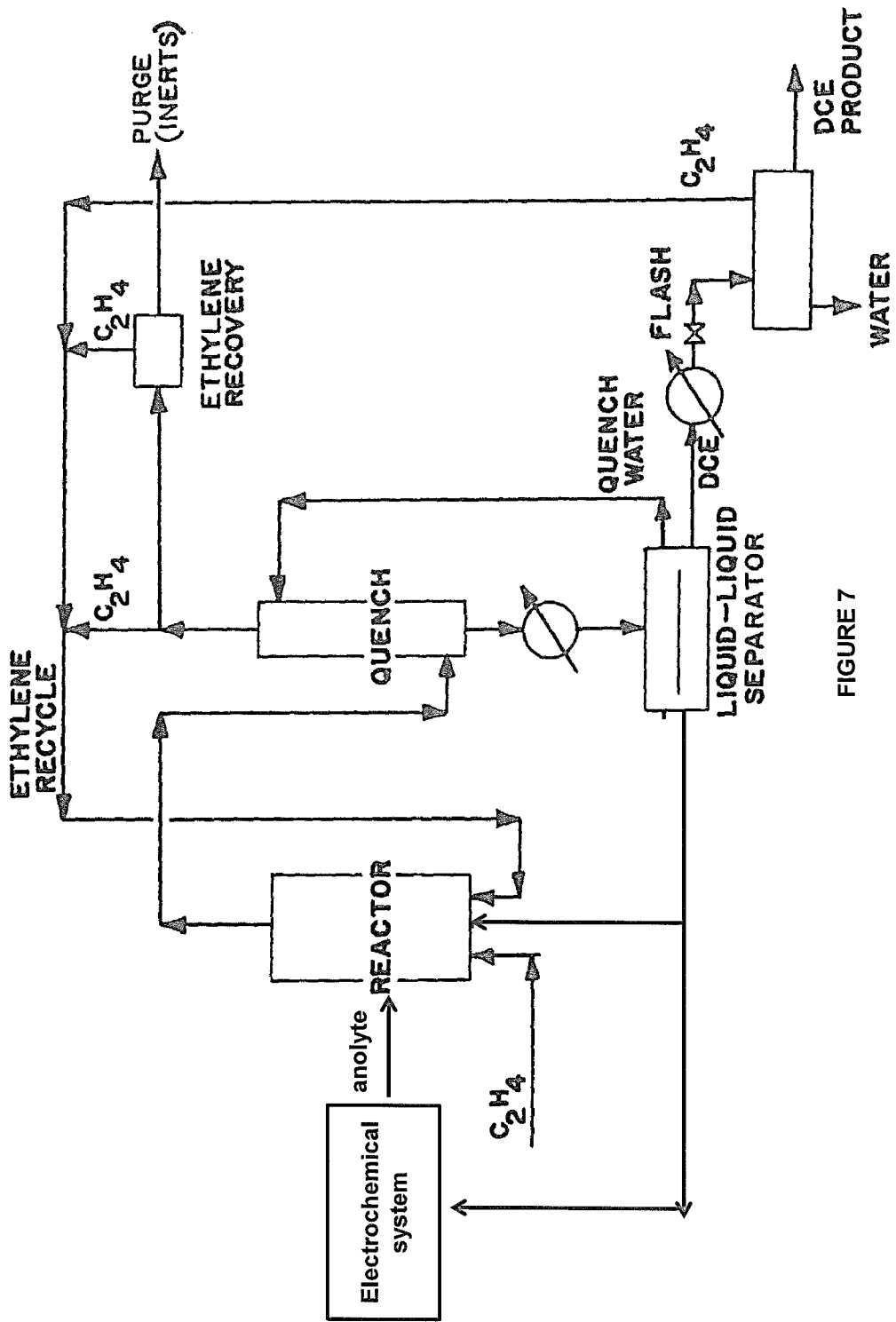
FIG. 7 is an illustration of some embodiments provided herein.

An illustrative example of the reactor that is connected to the electrochemical system is illustrated in FIG. 7. As illustrated in FIG. 7, the anode chamber of the electrochemical system (electrochemical system can be any electrochemical system described herein) is connected to a reactor which is also connected to a source of unsaturated or saturated hydrocarbon, an example illustrated as ethylene ($C_2H_4$) in FIG. 7. In some embodiments, the electrochemical system and the reactor are inside the same unit and are connected inside the unit. The anode electrolyte, containing the metal ion in the higher oxidation state optionally with the metal ion in the lower oxidation state, along with ethylene are fed to a prestressed (e.g., brick-lined) reactor. The chlorination of ethylene takes place inside the reactor to form ethylene dichloride (EDC or dichloroethane DCE) and the metal ion in the lower oxidation state.

The reactor effluent gases may be quenched with water (shown as "quench" reactor in FIG. 7) in the prestressed (e.g., brick-lined) packed tower. The liquid leaving the tower maybe cooled further and separated into the aqueous phase and EDC phase. The aqueous phase may be split part being recycled to the tower as quench water and the remainder may be recycled to the reactor or the electrochemical system. The EDC product may be cooled further and flashed to separate out more water and dissolved ethylene. This dissolved ethylene may be recycled as shown in FIG. 7. The uncondensed gases from the quench tower may be recycled to the reactor, except for the purge stream to remove inerts. The purge stream may go through the ethylene recovery system to keep the over-all utilization of ethylene high, e.g., as high as 95%. Experimental determinations may be made of flammability limits for ethylene gas at actual process temperature, pressure and compositions. The construction material of the plant may include prestressed brick linings, Hastealloys B and C, inconel, dopant grade titanium (e.g. AKOT, Grade II), tantalum, Kynar, Teflon, PEEK, glass, or other polymers or plastics. The reactor may also be designed to continuously flow the anode electrolyte in and out of the reactor.

Figure 8:
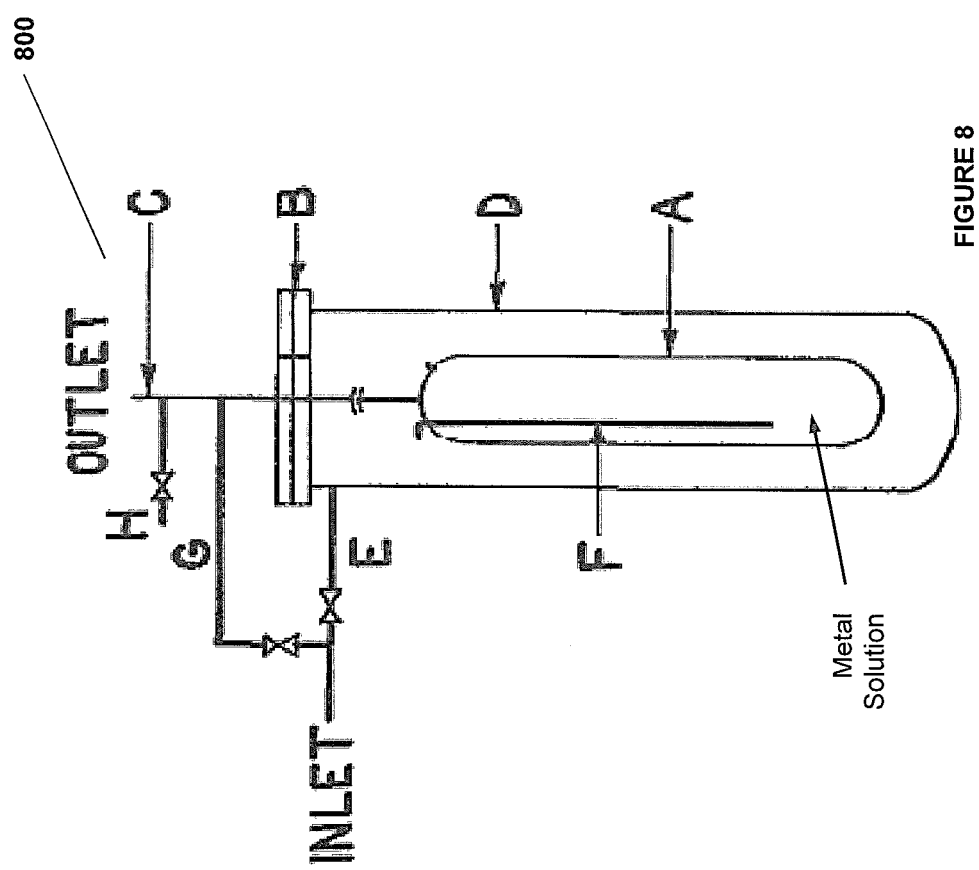
FIG. 8 is an illustration of some embodiments provided herein.

Another illustrative example of the reactor that is connected to the electrochemical system is as illustrated in FIG. 8. As illustrated in FIG. 8, the reactor system 800 is a glass vessel A, suspended from the top portion of a metal flange B, connected to an exit line C, by means of a metal ball socket welded to the head of the flange. The glass reactor is encased in an electrically heated metal shell, D. The heat input and the temperature may be controlled by an automatic temperature regulator. The hydrocarbon may be introduced into the metal shell through an opening E and through the glass tube F, which may be fitted with a fitted glass foot. This arrangement may provide for pressure equalization on both sides of the glass reactor. The hydrocarbon may come into contact with the metal solution (metal in higher oxidation state) at the bottom of the reactor and may bubble through the medium. The volatile products, water vapor, and/or unreacted hydrocarbon may leave via line C, equipped optionally with valve H which may reduce the pressure to atmosphere. The exiting gases may be passed through an appropriate trapping system to remove the product. The apparatus may also be fitted with a bypass arrangement G, which permits the passage of the gas through the pressure zone without passing through the aqueous metal medium. In some embodiments, the reduced metal ions in lower oxidation state that are left in the vessel, are subjected to electrolysis, as described herein, to regenerate the metal ions in the higher oxidation state.

Applicants have found that the conditions in the reactor may be selected in such a way that the halogenated hydrocarbon such as, but not limited to, EDC, is produced with high selectivity, high yield, and/or high STY.

In some embodiments, the reaction between the metal chloride with metal ion in higher oxidation state and the unsaturated or saturated hydrocarbon, is carried out in the reactor provided herein under reaction conditions including, but not limited to, the temperature of between 100-200° C. or between 100-175° C. or between 150-185° C. or between 150-175° C.; pressure of between 100-500 psig or between 100-400 psig or between 100-300 psig or between 150-350 psig or between 200-300 psig, or combinations thereof. The reactor provided herein is configured to operate at the temperature of between 100-200° C. or between 100-185° C. or between 150-200° C. or between 150-175° C.; pressure of between 100-500 psig or between 100-400 psig or between 100-300 psig or between 150-350 psig or between 200-300 psig, or combinations thereof. In some embodiments, the components of the reactor are lined with Teflon to prevent corrosion of the components. In some embodiments, the reactor provided herein may operate under reaction conditions including, but not limited to, the temperature and pressure in the range of between 135-180° C., or between 135-175° C., or between 140-180° C., or between 140-170° C., or between 140-160° C., or between 150-180° C., or between 150-170° C., or between 150-160° C., or between 155-165° C., or 140° C., or 150° C., or 160° C., or 170° C. and 200-300 psig. In some embodiments, the reactor provided herein may operate under reaction conditions including, but not limited to, the temperature and pressure in the range of between 135-180° C., or between 135-175° C., or between 140-180° C., or between 140-170° C., or between 140-160° C., or between 150-180° C. and 200-300 psig. In some embodiments, the temperature and pressure conditions described above, result in the production of the halogenated hydrocarbon such as, but not limited to, EDC, with high selectivity, high yield, and/or high STY. For example, in some embodiments, the above described temperature and pressure results in the production of the halogenated hydrocarbon with more than about 0.1 STY or more than about 0.5 STY or between 0.1-5 STY, or between 0.5-3 STY, or between 0.5-2, or between 0.5-1, or more than about 80% selectivity or between 80-99% selectivity.

One or more of other reaction conditions include, such as, but not limited to, metal ion concentration, ratio of the metal ion in the lower oxidation state to the metal ion in the higher oxidation state in the anode electrolyte, partial pressures of the unsaturated or saturated hydrocarbon (e.g., ethylene) and water vapor, flow rate of the anode electrolyte, flow rate of the unsaturated or saturated hydrocarbon, density (function of metal salt concentration), viscosity, and/or reaction time, can be set to assure high selectivity, high yield, and/or high STY operation. Various reaction conditions have been illustrated in the examples section. For example, the metal ion concentration and the ratio of the metal ion in the lower oxidation state to the metal ion in the higher oxidation state in the anode electrolyte has been described herein in the description as well as in the examples. The flow rate of the anolyte has also been described in the examples 9 and 10 and may be between 150-300 kg/h; or between 150-500 kg/h; or between 150-1000 kg/h; or between 150-250 kg/h.

Reaction heat may be removed by vaporizing water or by using heat exchange units. In some embodiments, a cooling surface may not be required in the reactor and thus no temperature gradients or close temperature control may be needed.

In some embodiments, there is provided a method comprising contacting an anode with an anode electrolyte wherein the anode electrolyte comprises metal ion; oxidizing the metal ion from a lower oxidation state to a higher oxidation state at the anode; and reacting an unsaturated or saturated hydrocarbon with the anode electrolyte comprising the metal ion in the higher oxidation state in an aqueous medium, to form one or more organic compounds comprising halogenated or sulfonated hydrocarbon and the metal ion in the lower oxidation state, wherein the reacting is under one or more of reaction conditions favorable to produce the halogenated or sulfonated hydrocarbon with more than about 0.1 STY or more than about 0.5 STY or between 0.1-5

STY, or between 0.5-3 STY, or more than about 80% selectivity or between 80-99% selectivity. In some embodiments of the aforementioned embodiment, the one or more of reaction conditions include temperature between 100-200° C., or between 150-250° C., pressure of between 100-300 psig, or between 200-300 psig, metal ion concentration e.g. between 1-8M or between 3-8M, ratio of metal ion in the lower oxidation state to the metal ion in the higher oxidation state in the anode electrolyte, partial pressure of the unsaturated or saturated hydrocarbon, partial pressure of water vapor, flow rate of the anode electrolyte e.g. between 150-300 kg/h, flow rate of the unsaturated or saturated hydrocarbon, density of the anode electrolyte or the aqueous medium, viscosity of the anode electrolyte, reaction time, or combinations thereof. In some embodiments of the aforementioned embodiments, the method further includes contacting a cathode with a cathode electrolyte to form an alkali, water, and/or hydrogen gas in the cathode electrolyte. In some embodiments of the aforementioned embodiments, the reaction conditions produce the halogenated hydrocarbon product with an STY of between 0.3-1; or between 0.5-2; or between 0.5-1; or between 0.5-3. In some embodiments of the aforementioned embodiments, the reaction conditions produce the halogenated or sulfonated hydrocarbon product with selectivity of more than 80%; or between about 80-99%; or between about 80-99.9%; or between about 90-99.9%; or between about 95-99.9%. In some embodiments of the aforementioned embodiments, the reaction conditions produce the halogenated or sulfonated hydrocarbon product with yield of more than 80%; or between about 80-99%; or between about 80-99.9%; or between about 90-99.9%; or between about 95-99.9%. In some embodiments of the aforementioned embodiments, the reaction conditions produce the halogenated or sulfonated hydrocarbon product with more than 90% purity (amount of the halogenated hydrocarbon product/amount of all the products) or more than 95% purity or more than 99% purity or more than 99.9% purity. Some embodiments of the aforementioned embodiments further comprise separating and/or purifying the halogenated or sulfonated hydrocarbon from the metal ions solution. Some embodiments of the aforementioned embodiments further comprise recirculating the separated metal ion solution comprising metal ion in the lower oxidation state and optionally comprising metal ion in the higher oxidation state, back to the anode electrolyte. In some embodiments of the aforementioned embodiments, the metal ions, the unsaturated and/or saturated hydrocarbon, and/or the one or more organic compounds comprising halogenated or sulfonated hydrocarbon, have all been described herein. In some embodiments of the aforementioned embodiments, the metal ion is copper. In some embodiments of the aforementioned embodiments, the unsaturated hydrocarbon is ethylene. In some embodiments of the aforementioned embodiments, the saturated hydrocarbon is ethane. In some embodiments of the aforementioned embodiments, the halogenated hydrocarbon is EDC.

Additionally, Applicants have found that design and configuration of the reactor may be selected in such a way that the halogenated or sulfonated hydrocarbon such as, but not limited to, EDC, is produced with high selectivity, high yield, high purity, and/or high STY. The reactor configuration includes, but not limited to, design of the reactor such as, e.g. length/diameter ratio, flow rates of the liquid and gases, material of construction, packing material and type if reactor is packed column or trickle-bed reactor, or combinations thereof. In some embodiments, the systems may include one reactor or a series of multiple reactors connected to each other or operating separately. The reactor may be a packed bed such as, but not limited to, a hollow tube, pipe, column or other vessel filled with packing material. The reactor may be a trickle-bed reactor. In some embodiments, the packed bed reactor includes a reactor configured such that the aqueous medium containing the metal ions and the unsaturated or saturated hydrocarbon (e.g. ethylene gas) flow counter-currently in the reactor or includes the reactor where the aqueous medium containing the metal ions flows in from the top of the reactor and the ethylene gas is pressured in from the bottom at e.g., but not limited to, 250 psi. In some embodiments, in the latter case, the ethylene gas may be pressured in such a way that only when the ethylene gas gets consumed and the pressure drops, that more ethylene gas flows into the reactor. The trickle-bed reactor includes a reactor where the aqueous medium containing the metal ions and the unsaturated or saturated hydrocarbon (e.g. ethylene gas) flow co-currently in the reactor.

In some embodiments, the unsaturated or saturated hydrocarbon feedstock may be fed to the halogenation or sulfonation vessel or the reactor continuously or intermittently. Efficient halogenation or sulfonation may be dependent upon achieving intimate contact between the feedstock and the metal ion in solution and the halogenation or sulfonation reaction may be carried out by a technique designed to improve or maximize such contact. The metal ion solution may be agitated by stirring or shaking or any desired technique, e.g. the reaction may be carried out in a column, such as a packed column, or a trickle-bed reactor or reactors described herein. For example, where the unsaturated or saturated hydrocarbon is gaseous, a counter-current technique may be employed wherein the unsaturated or saturated hydrocarbon is passed upwardly through a column or reactor and the metal ion solution is passed downwardly through the column or reactor. In addition to enhancing contact of the unsaturated or saturated hydrocarbon and the metal ion in the solution, the techniques described herein may also enhance the rate of dissolution of the unsaturated or saturated hydrocarbon in the solution, as may be desirable in the case where the solution is aqueous and the water-solubility of the unsaturated or saturated hydrocarbon is low. Dissolution of the feedstock may also be assisted by higher pressures.

In some embodiments, the reactor (may be a trickle bed or packed bed reactor) is configured in such a way that the length (or the height)/diameter ratio of the reactor is between 2-40 (e.g. 2:1 to 40:1); or between 2-35; or between 2-30; or between 2-20; or between 2-15; or between 2-10; or between 2-5; or between 3-40; or between 3-35; or between 3-30; or between 3-20; or between 3-10; or between 3-5; or between 4-40; or between 4-35; or between 4-30; or between 4-20; or between 4-10; or between 4-5; or between 6-40; or between 6-35; or between 6-30; or between 6-20; or between 6-10; or between 10-40; or between 10-35; or between 10-30; or between 10-25; or between 10-20; or between 10-15; or between 15-40; or between 15-35; or between 15-30; or between 15-25; or between 20-40; or between 20-35; or between 20-30; or between 20-25; or between 25-40; or between 25-35; or between 25-30; or between 30-40. In some embodiments, the foregoing diameter is the outside diameter of the reactor. In some embodiments, the foregoing diameter is the inside diameter of the reactor. For example, in some embodiments, the length/diameter ratio of the reactor is between about 2-15; or 2-20; or 2-25; or 10-15; or 10-25; or 20-25; or 20-30; or 30-40; or 35-40; or 4-25; or 6-15; or between 2:1-40:1; or between 2:1-10:1 or about 3:1 or about 4:1.

A variety of packing material of various shapes, sizes, structure, wetting characteristics, form, and the like may be used in the packed bed or trickle bed reactor, described herein. The packing material includes, but not limited to, polymer (e.g. only Teflon PTFE), ceramic, glass, metal, natural (wood or bark), or combinations thereof. In some embodiments, the packing can be structured packing or loose or unstructured or random packing or combination thereof. The "structured packing" as used herein includes unflowable corrugated metal plates or gauzes. In some embodiments, the structured packing material individually or in stacks fits fully in the diameter of the reactor. The "unstructured packing" or "loose packing" or "random packing" as used herein includes flowable void filling packing material.

Examples of loose or unstructured or random packing material include, but not limited to, raschig rings (such as in ceramic material), pall rings (e.g. in metal and plastic), lessing rings, michael bialecki rings (e.g. in metal), berl saddles, intalox saddles (e.g. in ceramic), super intalox saddles, Tellerette® ring (e.g. spiral shape in polymeric material), etc.

In some embodiments, the size of the unstructured packing material may vary and may be between about 2 mm to about 5 inches or between about ¼ of an inch to about 5 inches. In some embodiments, the size of the packing material is between about 2 mm to about 5 inches; or about 2 mm to about 4 inches; or about 2 mm to about 3 inches; or about 2 mm to about 2 inches; or about 2 mm to about 1 inch; or about 2 mm to about ½ inch; or about 2 mm to about ¼ inch; or about ¼ of an inch to about 5 inches; or about ¼ of an inch to about 4 inches; or about ¼ of an inch to about 3 inches; or about ¼ of an inch to about 2 inches; or about ¼ of an inch to about 1 inch; or about ¼ of an inch to about ½ inch; or about ⅓ of an inch to about 5 inches; or about ⅓ of an inch to about 2 inches; or about ½ of an inch to about 5 inches; or about ½ of an inch to about 4 inches; or about ½ of an inch to about 3 inches; or about ½ of an inch to about 2 inches; or about ½ of an inch to about 1 inch; or about 1 inch to about 5 inches; or about 1 inch to about 4 inches; or about 1 inch to about 3 inches; or about 1 inch to about 2 inches; or about 1 inch to about ½ inches; or about 1 inch to about ¼ inches; or about 2 inch to about 5 inches; or about 3 inch to about 5 inches; or about 4 inch to about 5 inches. In some embodiments, the size of the packing material is between about ¼ of an inch to about 4 inches; or about ½ of an inch to about 3 inches; or about 1 inch to about 2 inches.

Examples of structured packing material include, but not limited to, thin corrugated metal plates or gauzes (honeycomb structures) in different shapes with a specific surface area. The structured packing material may be used as a ring or a layer or a stack of rings or layers that have diameter that may fit into the diameter of the reactor. The ring may be an individual ring or a stack of rings fully filling the reactor. In some embodiments, the voids left out by the structured packing in the reactor are filled with the unstructured packing material.

Examples of structured packing material includes, without limitation, Flexipac®, Intalox®, Flexipac® HC®, etc. In a structured packing material, corrugated sheets may be arranged in a crisscross pattern to create flow channels for the vapor phase. The intersections of the corrugated sheets may create mixing points for the liquid and vapor phases. The structured packing material may be rotated about the column (reactor) axis to provide cross mixing and spreading of the vapor and liquid streams in all directions. The structured packing material may be used in various corrugation sizes and the packing configuration may be optimized to attain the highest efficiency, capacity, and pressure drop requirements of the reactor. The structured packing material may be made of a material of construction including, but not limited to, titanium, stainless steel alloys, carbon steel, aluminum, nickel alloys, copper alloys, zirconium, thermoplastic, etc. The corrugation crimp in the structured packing material may be of any size, including, but not limited to, Y designated packing having an inclination angle of 45° from the horizontal or X designated packing having an inclination angle of 60° from the horizontal. The X packing may provide a lower pressure drop per theoretical stage for the same surface area. The specific surface area of the structured packing may be between 50-800 $m^2/m^3$; or between 75-350 $m^2/m^3$; or between 200-800 $m^2/m^3$; or between 150-800 $m^2/m^3$; or between 500-800 $m^2/m^3$.

In some embodiments, the structured or the unstructured packing material as described above is used in the distillation or flash column described herein for separation and purification of the products.

Accordingly, in some embodiments there are provided systems comprising an electrochemical system comprising an anode chamber comprising an anode in contact with an anode electrolyte comprising metal ions wherein the anode is configured to oxidize the metal ions from a lower oxidation state to a higher oxidation state; and a reactor operably connected to the anode chamber and configured to contact the anode electrolyte comprising the metal ions in the higher oxidation state with an unsaturated and/or saturated hydrocarbon to form one or more organic compounds comprising halogenated or sulfonated hydrocarbon and the metal ion in the lower oxidation state, wherein the reactor has a length: diameter ratio of between 2-40, or 2-30, or 4-25, or 2-10, or 15-40, or 30-40 (e.g. 30:1-40:1). In some embodiments of the aforementioned embodiment, the electrochemical system further includes a cathode chamber comprising a cathode in contact with a cathode electrolyte wherein the cathode is configured to form an alkali, water, and/or hydrogen gas in the cathode electrolyte. In some embodiments of the aforementioned embodiments, the reactor is a packed-bed reactor or a trickle-bed reactor. In some embodiments of the aforementioned embodiments, the reactor is packed with a packing material including, but not limited to, structured packing, unstructured packing, or combination thereof. Examples of loose or unstructured or random packing material include, but not limited to, raschig rings (such as in ceramic material), pall rings (e.g. in metal and plastic), lessing rings, michael bialecki rings (e.g. in metal), berl saddles, intalox saddles (e.g. in ceramic), super intalox saddles, Tellerette® ring (e.g. spiral shape in polymeric material), etc. Examples of structured packing material include, but not limited to, thin corrugated metal plates or gauzes (honeycomb structures) in different shapes. In some embodiments of the aforementioned embodiments, the size of the unstructured packing material may vary and may be between about 2 mm to about 5 inches; or about ¼ of an inch to about 5 inches; or between 3 mm to about ¼ of an inch; or between ¼ of an inch to about ½ of an inch. In some embodiments of the aforementioned embodiments, the reactor is configured to produce the halogenated or sulfonated hydrocarbon product with an STY of more than 0.5; or between 0.3-1; or between 0.5-2; or between 0.5-1; or between 0.5-3. In some embodiments of the aforementioned embodiments, the reactor is configured to produce the halogenated or sulfonated hydrocarbon product with a selectivity of more than 80%; or between about 80-99%; or between about 80-99.9%; or between about 90-99.9%; or between about 95-99.9%. Some embodiments of the aforementioned embodiments further comprise a separator to separate and/or purify the halogenated or sulfonated hydrocarbon from the metal ions solution. Some embodiments of the aforementioned embodiments further comprise a recirculation system to recirculate the separated metal ion solution comprising metal ion in the lower oxidation state and optionally comprising metal ion in the higher oxidation state, back to the anode electrolyte. In some embodiments of the aforementioned embodiments, the metal ions, the unsaturated and/or saturated hydrocarbon, and/or the one or more organic compounds comprising halogenated hydrocarbon, have all been described herein. In some embodiments of the aforementioned embodiments, the metal ion is copper. In some embodiments of the aforementioned embodiments, the unsaturated hydrocarbon is ethylene. In some embodiments of the aforementioned embodiments, the saturated hydrocarbon is ethane. In some embodiments of the aforementioned embodiments, the halogenated hydrocarbon is EDC.

Various examples of the reactor configurations and the packing materials have been provided herein.

In some embodiments, the reactor may be configured for both the reaction and separation of the products. Detailed description of such reactors is provided herein below in the separation and purification section.

The processes and systems described herein may be batch processes or systems or continuous flow processes or systems.

All the electrochemical and reactor systems and methods described herein are carried out in more than 5 wt % water or more than 6 wt % water or aqueous medium. In one aspect, the methods and systems provide an advantage of conducting the metal oxidation reaction in the electrochemical cell and reduction reaction outside the cell, all in an aqueous medium. The use of aqueous medium, in the halogenations or sulfonation of the unsaturated or saturated hydrocarbon, not only resulted in high yield and high selectivity of the product (shown in examples herein) but also resulted in the generation of the reduced metal ion with lower oxidation state in the aqueous medium which could be re-circulated back to the electrochemical system. In some embodiments, since the electrochemical cell runs efficiently in the aqueous medium, no removal or minimal removal of water (such as through azeotropic distillation) is required from the anode electrolyte containing the metal ion in the higher oxidation state which is reacted with the unsaturated or saturated hydrocarbon in the aqueous medium. Therefore, the use of the aqueous medium in both the electrochemical cell and the catalysis system provides efficient and less energy intensive integrated systems and methods of the invention.

The reaction of the unsaturated or saturated hydrocarbon with the metal ion in the higher oxidation state, as described in the aspects and embodiments herein, is carried out in the aqueous medium. In some embodiments, such reaction may be in a non-aqueous liquid medium which may be a solvent for the hydrocarbon feedstock. The liquid medium or solvent may be aqueous or non-aqueous. Suitable non-aqueous solvents being polar and non-polar aprotic solvents, for example dimethylformamide (DMF), dimethylsulphoxide (DMSO), halogenated hydrocarbons, for example only, dichloromethane, carbon tetrachloride, and 1,2-dichloroethane, and organic nitriles, for example, acetonitrile. Organic solvents may contain a nitrogen atom capable of forming a chemical bond with the metal in the lower oxidation state thereby imparting enhanced stability to the metal ion in the lower oxidation state. In some embodiments, acetonitrile is the organic solvent.

In some embodiments, when the organic solvent is used for the reaction between the metal ion in the higher oxidation state with the hydrocarbon, the water may need to be removed from the metal containing medium. As such, the metal ion obtained from the electrochemical systems described herein may contain water. In some embodiments, the water may be removed from the metal ion containing medium by azeotropic distillation of the mixture. In some embodiments, the solvent containing the metal ion in the higher oxidation state and the unsaturated or saturated hydrocarbon may contain between 5-90%; or 5-80%; or 5-70%; or 5-60%; or 5-50%; or 5-40%; or 5-30%; or 5-20%; or 5-10% by weight of water in the reaction medium. The amount of water which may be tolerated in the reaction medium may depend upon the particular halide carrier in the medium, the tolerable amount of water being greater, for example, for copper chloride than for ferric chloride. Such azeotropic distillation may be avoided when the aqueous medium is used in the reactions.

In some embodiments, the reaction of the metal ion in the higher oxidation state with the unsaturated or saturated hydrocarbon may take place when the reaction temperature is above 50° C. up to 350° C. In aqueous media, the reaction may be carried out under a super atmospheric pressure of up to 1000 psi or less to maintain the reaction medium in liquid phase at a temperature of from 50° C. to 200° C., typically from about 120° C. to about 180° C.

In some embodiments, the reaction of the metal ion in the higher oxidation state with the unsaturated or saturated hydrocarbon may include a halide carrier. In some embodiments, the ratio of halide ion:total metal ion in the higher oxidation state is 1:1; or greater than 1:1; or 1.5:1; or greater than 2:1 and or at least 3:1. Thus, for example, the ratio in cupric halide solutions in concentrated hydrochloric acid may be about 2:1 or 3:1. In some embodiments, owing to the high rate of usage of the halide carrier it may be desired to use the metal halides in high concentration and to employ saturated or near-saturated solutions of the metal halides. If desired, the solutions may be buffered to maintain the pH at the desired level during the halogenation reaction.

In some embodiments, a non-halide salt of the metal may be added to the solution containing metal ion in the higher oxidation state. The added metal salt may be soluble in the metal halide solution. Examples of suitable salts for incorporating in cupric chloride solutions include, but are not limited to, copper sulphate, copper nitrate and copper tetrafluoroborate. In some embodiments a metal halide may be added that is different from the metal halide employed in the methods and systems. For example, ferric chloride may be added to the cupric chloride systems at the time of halogenations of the unsaturated hydrocarbon.

Mixtures of saturated, unsaturated hydrocarbons and/or partially halogenated hydrocarbons may be employed. In some embodiments, partially-halogenated products of the process of the invention which are capable of further halogenation may be recirculated to the reaction vessel through a product-recovery stage and, if appropriate, a metal ion in the lower oxidation state regeneration stage. In some embodiments, the halogenation reaction may continue outside the halogenation reaction vessel, for example in a separate regeneration vessel, and care may need to be exercised in controlling the reaction to avoid over-halogenation of the unsaturated or saturated hydrocarbon.

Separation and Purification of Products and Metals

In some embodiments, the methods and systems described herein include separation and purification of the halogenated hydrocarbon and/or other organic products (formed during and/or after the reaction of the saturated or unsaturated hydrocarbon with metal ion in higher oxidation state, as described herein) from the metal ions and the separation and purification of the metal ions before circulating the metal ion solution back in the electrochemical cell (e.g. FIG. 1A). In some embodiments, it may be desirable to remove the organics from the aqueous medium containing metal ions before the metal ion solution is circulated back to the electrochemical cell to prevent the fouling of the membranes in the electrochemical cell. As described herein above, the aqueous medium containing the metal ions, after the reaction with the unsaturated or saturated hydrocarbon, contains the organic products such as, but not limited to, halogenated hydrocarbon and other side products (may be present in trace amounts). For example, the metal ion solution containing the metal ion in the higher oxidation state is reacted with ethylene to form the metal ion in the lower oxidation state and ethylene dichloride. Other side products may be formed including, but not limited to, chloroethanol, dichloroacetaldehyde, trichloroacetaldehyde (chloral), etc. There are provided methods and systems to separate and purify the organic products from the metal ions in the aqueous medium and to separate and purify the metal ion solution (containing both the metal ion in the higher oxidation state and the metal ion in the lower oxidation state) before circulating the aqueous medium containing the metal ions back to the electrochemical cell. The aqueous medium may be a mixture of both the metal ion in the lower oxidation state and the metal ion in the higher oxidation state, the ratio of the lower and higher oxidation state will vary depending on the aqueous medium from the electrochemical cell (where lower oxidation state is converted to higher oxidation state) and the aqueous medium after reaction with the hydrocarbon (where higher oxidation state is converted to the lower oxidation state).

Illustrated in FIG. 9A are some embodiments of the methods and systems provided herein. It is to be understood that one or more steps from the flow diagram illustrated in FIG. 9A may be omitted or one or more steps may be combined to carry out the methods and systems of the invention. The order of the steps may also be altered or modified to achieve ease of use, lower costs, higher purity and selectivity of the products. Similar steps may be also be used for the sulfonation reaction of the hydrocarbons to form sulfohydrocarbons. At step A, the hydrocarbon (illustrated as ethylene) is subjected to halogenation in the reactor, as described herein and in FIGS. 6-8. The halogenated hydrocarbon (illustrated as ethylene dichloride) along with metal salts $MCl_n$ may be subjected to separation and purification at step B. It is to be understood that $MCl_n$ shown in the figures illustrated herein, is a mixture of the metal ion in the lower oxidation state as well as the metal ion in the higher oxidation state. The integer n in $MCl_n$ merely represents the metal ion in the lower and higher oxidation state and may be from 1-5 or more depending on the metal ion. For example, in some embodiments, where copper is the metal ion, the $MCl_n$ may be a mixture of $CuCl$ and $CuCl_2$. This mixture of copper ions in the anode electrolyte may be then contacted with the unsaturated hydrocarbon and/or saturated hydrocarbon to form respective products.

Some examples of the reaction in the reactor and the configuration of the reactor have been described herein above.

Accordingly, in some embodiments, there is provided a method comprising contacting an anode with an anode electrolyte wherein the anode electrolyte comprises metal ion; oxidizing the metal ion from a lower oxidation state to a higher oxidation state at the anode; reacting an unsaturated or saturated hydrocarbon with the anode electrolyte comprising the metal ion in the higher oxidation state in an aqueous medium, to form one or more organic compounds comprising halogenated hydrocarbon and the metal ion in the lower oxidation state; and separating and purifying the one or more organic compounds comprising halogenated hydrocarbon from the aqueous medium. Accordingly, there is provided a system including an electrochemical system comprising an anode chamber comprising an anode in contact with an anode electrolyte comprising metal ion wherein the anode is configured to oxidize the metal ion from a lower oxidation state to a higher oxidation state; a reactor operably connected to the anode chamber and configured to react an unsaturated hydrocarbon or saturated hydrocarbon in an aqueous medium with the anode electrolyte comprising the metal ion in the higher oxidation state to form one or more organic compounds comprising halogenated hydrocarbon and the metal ion in the lower oxidation state; and a separator configured to separate and purify the one or more organic compounds comprising halogenated hydrocarbon from the aqueous medium. The "separator" as used herein includes one or more vessels or units that are configured to separate the organic compound(s) (such as halo or sulfo hydrocarbon) from the aqueous metal ion solution. The separator may further purify the organic compound and the aqueous metal ion solution. Various examples of the separation and purification process as well as the systems configured to carry out the separation and purification process (the separator) are as described below.

In some embodiments, as illustrated in FIG. 9A, the step A of the halogenation reaction in the reactor may be combined with the step B of the separation of the products, referred to herein as "reactive separation" or "reaction separation". As used herein, "reactive separation" or "reaction separation" includes reaction of the hydrocarbon as well as partial or full separation of the halogenated or sulfonated product(s). As used herein, "reactive separation reactor" or "reaction separation reactor" includes reactors that are configured to carry out the reaction of the hydrocarbon as well as partial or full separation of the halogenated or sulfonated product(s). Examples of reaction separation as well as reaction separation reactor are described herein. In some embodiments, the separation of the products may be partial or full but some element of the separation of the products is combined with the reaction. The reactive separation may result in the ease of operation and separation, lower costs, and higher selectivity in the reactor. In some embodiments, the reactive separation can be beneficial in reactions that are carried out in series where the product once formed undergoes further reactions to form byproducts. For example, EDC once formed from ethylene may undergo further reaction to form chloroethanol and other side products described herein. In such reactions, the reactive separation may be beneficial in reducing the separation cost and achieving high selectivity of EDC.

Accordingly, in some embodiments, there is provided a method including contacting an anode with an anode electrolyte wherein the anode electrolyte comprises metal ion; oxidizing the metal ion from a lower oxidation state to a higher oxidation state at the anode, causing reaction separation of an unsaturated or saturated hydrocarbon with the anode electrolyte comprising the metal ion in the higher oxidation state in an aqueous medium, to form and separate one or more organic compounds comprising halogenated or sulfonated hydrocarbon from the aqueous medium comprising the metal ion in the lower oxidation state and the metal ion in the higher oxidation state. In some embodiments of the foregoing method, the method further comprises recirculating the aqueous medium comprising metal ion in the lower oxidation state and the metal ion in the higher oxidation state back to the anode electrolyte. In some embodiments of the foregoing methods, the unsaturated hydrocarbon, the saturated hydrocarbon, the halogenated hydrocarbon, the metal ions, etc. have all been described in detail herein. In some embodiments of the foregoing methods, the metal ion is copper, the unsaturated hydrocarbon is ethylene and the organic compound comprises EDC. In some embodiments of the aforementioned methods, the reactive separation may include, but not limited to, reactive distillation (vapor-liquid separation), reactive extraction (liquid-liquid separation), or combinations thereof.

In some embodiments of the aforementioned methods, the reactive separation of an unsaturated or saturated hydrocarbon with the anode electrolyte comprising the metal ion in the higher oxidation state in an aqueous medium, to form and separate one or more organic compounds comprising halogenated or sulfonated hydrocarbon from the aqueous medium comprising the metal ion in the lower oxidation state and the metal ion in the higher oxidation state, is reactive distillation. In reactive distillation, a low boiling point product once formed in the reactor, may be removed from the reactor in a vapor phase. For example only, EDC has a lower boiling point (83.6° C.) than water (100° C.) and may be removed from the metal chloride containing liquid phase as a vapor. Chloroethanol which may be the major side product with EDC has a higher boiling point than water and would stay in the liquid phase. Therefore, reactive distillation can be used to separate the desired product from the byproducts. The reactive distillation method may be aided by other factors. For example only, the presence of dissolved salts in the liquid phase may increase the boiling point of water through boiling point elevation effects. Additionally, EDC may form a low boiling azeotrope with water which may increase the effective volatility of EDC. These factors may further help the reactive distillation of the desired product, such as, e.g. EDC. In some embodiments, the vapor phase from the reactor containing the organic product, such as, but not limited to EDC may also contain the unreacted reactant gas e.g. ethylene. In such embodiments, EDC is removed from ethylene using a compression-cooling process described in detail herein below in reference to FIG. 9B.

In some embodiments, there is provided a system, comprising an anode in contact with an anode electrolyte comprising metal ion wherein the anode is configured to oxidize the metal ion from a lower oxidation state to a higher oxidation state; and a reaction separation reactor operably connected to the anode chamber and configured to cause reaction separation of an unsaturated hydrocarbon or saturated hydrocarbon in an aqueous medium with the anode electrolyte comprising the metal ion in the higher oxidation state to form and separate one or more organic compounds comprising halogenated or sulfonated hydrocarbon from the aqueous medium comprising the metal ion in the lower oxidation state and the metal ion in the higher oxidation state. In some embodiments of the foregoing systems, the unsaturated hydrocarbon, the saturated hydrocarbon, the halogenated hydrocarbon, the metal ions, etc. have all been described in detail herein. In some embodiments of the foregoing systems, the metal ion is copper, the unsaturated hydrocarbon is ethylene and the organic compound comprises EDC.

In some embodiments of the foregoing systems, the reaction separation reactor operably connected to the anode chamber and configured to cause reaction separation of an unsaturated hydrocarbon or saturated hydrocarbon in an aqueous medium with the anode electrolyte comprising the metal ion in the higher oxidation state to form and separate one or more organic compounds comprising halogenated or sulfonated hydrocarbon from the aqueous medium comprising the metal ion in the lower oxidation state and the metal ion in the higher oxidation state, is a reactive distillation reactor. In some embodiments, the reactive distillation reactor may be configured with various components that aid in the reactive distillation process. For example, the reactive distillation reactor may be a stirred tank and may include an ethylene sparger with a vapor phase removed from the top. The reactor may operate at temperature between 140-175° C. and pressure between 10-20 atm or between 12-18 atm. In some embodiments, the reactive distillation reactor may further include a gas-entrainment stirrer to increase vapor-liquid contacting. In some embodiments, the reactive distillation reactor may include a gas-entrainment stirrer without the ethylene sparger. In some embodiments, the reactive distillation reactor may be a packed bed with metal solution flowing in from the top and out from the bottom of the reactor and the ethylene entering from the bottom of the reactor and product flowing out of the top of the reactor. In some embodiments, the reactive distillation reactor may be a tray or plate column with metal solution flowing in from the top and out from the bottom of the reactor and the ethylene entering from the bottom of the reactor and product flowing out of the top of the reactor. Accordingly, in some embodiments, the reactive distillation reactor may include components such as, but not limited to, stirred tank, ethylene sparger, gas-entrainment stirrer, packed bed, tray or plate column, or combinations thereof.

In some embodiments of the aforementioned methods, the reactive separation of an unsaturated or saturated hydrocarbon with the anode electrolyte comprising the metal ion in the higher oxidation state in an aqueous medium, to form and separate one or more organic compounds comprising halogenated or sulfonated hydrocarbon from the aqueous medium comprising the metal ion in the lower oxidation state and the metal ion in the higher oxidation state, is reactive extraction. In reactive extraction, the low solubility of the organic product in aqueous phase may result in the extraction of the organic product from the aqueous phase. For example only, EDC has relatively low solubility in water, it tends to form a separate organic phase which is typically less dense than the salt-containing aqueous phase and may be removed as a separate phase. In some embodiments, the removal of EDC may be facilitated by the use of an organic extractant which may serve to remove (extract) EDC from the aqueous phase.

In some embodiments of the aforementioned systems, the reaction separation reactor operably connected to the anode chamber and configured to cause reaction separation of an unsaturated hydrocarbon or saturated hydrocarbon in an aqueous medium with the anode electrolyte comprising the metal ion in the higher oxidation state to form and separate one or more organic compounds comprising halogenated or sulfonated hydrocarbon from the aqueous medium comprising the metal ion in the lower oxidation state and the metal ion in the higher oxidation state, is a reactive extraction reactor. In some embodiments, the reactive extraction reactor may be configured with various components that aid in the reactive extraction process. For example, the reactive extraction reactor may be a stirred tank and may include an ethylene sparger with a vapor phase removed from the top. The reactor may operate at temperature between 140-175° C. and pressure between 10-20 atm or between 12-18 atm. In some embodiments, the reactive extraction reactor may further include a gas-entrainment stirrer to increase vapor-liquid contacting. In some embodiments, the reactive extraction reactor may include a gas-entrainment stirrer without the ethylene sparger. In some embodiments, the reactive extraction reactor may be a packed bed with metal solution and organic extractant flowing in from the top and out of the bottom of the reactor and the ethylene entering from the bottom of the reactor and product along with ethylene in the vapor phase flowing out of the top of the reactor.

An organic liquid phase containing EDC and other byproducts may be removed from the bottom of the reactor that may also include an aqueous phase as the lower layer. The feeds in this reactor may include ethylene, aqueous $MCl_n$, and the extractant and the organic product, such as EDC is extracted in the extractant (liquid-liquid separation described below). For example, the reactive extraction reactor may be integrated with a decanter which may be a separate vessel attached to the reactor. The liquid and vapor phases may then enter the decanter where the final separation of the phases may take place so that the effluents may include a liquid $MCl_n$-containing aqueous phase, a liquid organic phase, and optionally a vapor phase containing ethylene, EDC, water, and other organic compounds. The decanter may be attached to the reactor or may be a separate vessel that is in connection with the reactor. This organic liquid phase is then subjected to the decanter for the separation of the organic layer with the aqueous layer. In some embodiments, the reactive extraction reactor may be a tray or plate column with metal solution and organic extractant flowing in from the top and out of the bottom of the reactor and the ethylene entering from the bottom of the reactor and product along with ethylene in the vapor phase flowing out of the top of the reactor. An organic liquid phase containing EDC and other byproducts is removed from the bottom of the reactor that also includes an aqueous phase as the lower layer. This organic liquid phase is then subjected to the decanter for the separation of the organic layer with the aqueous layer. Accordingly, in some embodiments, the reactive extraction reactor may include components, but not limited to, stirred tank, ethylene sparger, gas-entrainment stirrer, packed bed, tray or plate column, or combinations thereof optionally along with a decanter attached to the reactor or a separate vessel from the reactor. As is understood from above, the reaction separation reactor may be a combination of the distillation reactor and the extraction reactor. In some embodiments, the reaction separation reactor may operably be connected to the compression-cooling system described below.

At step B illustrated in FIG. 9A, maximum amount of organic product may be removed (>50%, or >90% or >95% by mass) before the stream is sent to organic impurities separation step C. At step B, the separated organic product may be subjected to purification to improve the purity of the organic product for commercial use. In some embodiments, step B may be skipped and the organic product may be separated at step C. In some embodiments, step A may be a combined halogenations and separation B (reactive separation described above) and may or may not lead to step B for further separation and purification.

Step B is illustrated in detail in FIG. 9B. At step B, the organic product may be removed from the aqueous phase and further purified using various processes, such as, but not limited to, compression-cooling process, liquid-liquid separation process, vapor-liquid separation process, scrubbing process, purification subprocess, and combinations thereof. Accordingly, in some embodiments, there is provided a method including contacting an anode with an anode electrolyte wherein the anode electrolyte comprises metal ion; oxidizing the metal ion from a lower oxidation state to a higher oxidation state at the anode; reacting an unsaturated or saturated hydrocarbon with the anode electrolyte comprising the metal ion in the higher oxidation state in an aqueous medium, to form one or more organic compounds comprising halogenated hydrocarbon and the metal ion in the lower oxidation state; and separating and purifying the one or more organic compounds comprising halogenated hydrocarbon using processes including, but not limited to, reaction separation process, compression-cooling process, liquid-liquid separation process, vapor-liquid separation process, scrubbing process, purification subprocess, or combinations thereof. In some embodiments of the foregoing methods, the method further comprises recirculating the aqueous medium comprising metal ion in the lower oxidation state and the metal ion in the higher oxidation state back to the anode electrolyte. In some embodiments of the foregoing methods, the unsaturated hydrocarbon, the saturated hydrocarbon, the halogenated hydrocarbon, the metal ions, etc. have all been described in detail herein. In some embodiments of the foregoing methods, the metal ion is copper, the unsaturated hydrocarbon is ethylene and the halogenated hydrocarbon comprises EDC. In some embodiments of the foregoing methods, the method includes reaction separation as described above, and/or remaining organic separation (adsorbent in step C) as described further herein below.

In some embodiments, the order of the separation and purification process may be selected in such a way that a maximum amount of the product is isolated with minimum thermal requirements and maximum economical benefit. For example, in some embodiments, the aqueous stream exiting the reactor may be subjected first to vapor-liquid separation process where the vapors are separated and condensed followed by the liquid-liquid separation process in order to achieve high yield of the product with high purity and high economics and efficiency. In some embodiments, there is provided a method including contacting an anode with an anode electrolyte wherein the anode electrolyte comprises metal ion; oxidizing the metal ion from a lower oxidation state to a higher oxidation state at the anode; reacting an unsaturated or saturated hydrocarbon with the anode electrolyte comprising the metal ion in the higher oxidation state in an aqueous medium, to form one or more organic compounds comprising halogenated hydrocarbon and the metal ion in the lower oxidation state; and separating and purifying the one or more organic compounds comprising halogenated hydrocarbon using vapor-liquid separation process followed by liquid-liquid separation process.

In some embodiments, there is provided a system, comprising an electrochemical system comprising an anode chamber comprising an anode in contact with an anode electrolyte comprising metal ion wherein the anode is configured to oxidize the metal ion from a lower oxidation state to a higher oxidation state; a reactor operably connected to the anode chamber and configured to react an unsaturated hydrocarbon or saturated hydrocarbon in an aqueous medium with the anode electrolyte comprising the metal ion in the higher oxidation state to form one or more organic compounds comprising halogenated hydrocarbon and the metal ion in the lower oxidation state; and a separator configured to separate and purify the one or more organic compounds comprising halogenated hydrocarbon from the aqueous medium, wherein the separator includes but not limited to, reaction separation reactor system, compression-cooling system, liquid-liquid separator system, vapor-liquid separator system, scrubbing system, purification subprocess system, or combinations thereof. In some embodiments, there is provided a system, comprising an electrochemical system comprising an anode chamber comprising an anode in contact with an anode electrolyte comprising metal ion wherein the anode is configured to oxidize the metal ion from a lower oxidation state to a higher oxidation state; a reactor operably connected to the anode chamber and configured to react an unsaturated hydrocarbon or saturated hydrocarbon in an aqueous medium with the anode electrolyte comprising the metal ion in the higher oxidation state to form one or more organic compounds comprising halogenated hydrocarbon and the metal ion in the lower oxidation state; and a separator configured to separate and purify the one or more organic compounds comprising halogenated hydrocarbon from the aqueous medium, wherein the separator includes vapor-liquid separator system operably connected to the reactor followed by liquid-liquid separator system operably connected to the vapor-liquid separator system.

In some embodiments of the foregoing systems, the unsaturated hydrocarbon, the saturated hydrocarbon, the halogenated hydrocarbon, the metal ions, etc. have all been described in detail herein. In some embodiments of the foregoing systems, the metal ion is copper, the unsaturated hydrocarbon is ethylene and the organic compound comprises EDC. In some embodiments of the foregoing systems, the system further includes reaction separation reactor (e.g. distillation reactor or extraction reactor) as described above, and/or remaining organic separator (adsorbent in step C) as described further herein below.

At step B, the organic product in the vapor phase may also contain the hydrocarbon reactant, e.g. ethylene that may be recovered and recycled back to the reactor. The reactor may contain exiting stream containing a vapor stream and a liquid stream which may be separately subjected to separation and purification. For example, the vapor stream containing ethylene, water, EDC, and volatile byproducts may be removed from the reactor and fed to a compression-cooling system I configured to cause the compression-cooling process where the vapor stream is compressed to a pressure above that of the reactor, followed by cooling (or in the reverse order, i.e. cooling followed by compressing) in order to condense EDC, water, and byproducts as a liquid phase. "The compression-cooling process" or "the compression-cooling system" used herein includes any process or system that compresses and cools the vapor phase to condense it to form a liquid phase. The compression pressure may be between 150-900 psig, or between 250-800 psig, or between 400-600 psig. The cooling may be between 75-225° C., or between 100-200° C., or between 125-175° C. A phase separation may allow the separation of the liquid phase which may further be fed to the purification subprocess system IV. In some embodiments, the liquid phase from I may be fed to the liquid-liquid separation process II. Ethylene containing reduced amount of EDC, water, and byproducts may be then recycled back to the reactor as vapor stream. The compression cooling system may be any system configured to increase the pressure and reduce (or in reverse order) the temperature of the vapor stream. For example only, the vapor phase may be cooled at reactor pressure to 25-35° C., the condensed phases may be separated, and then the phase may be compressed to make up the pressure lost.

In some embodiments, the liquid stream leaving the reactor or the vapor-liquid separator and/or compression-cooling separator, may be fed to a liquid-liquid separator system II configured to cause the liquid-liquid separation, in which an organic rich liquid stream may be separated from the metal salt-containing aqueous stream. "The liquid-liquid separator process" or "the liquid-liquid separator system" used herein includes any process or system that partially or fully separates the organic liquid from the aqueous liquid. In such a process, a substantial quantity of organics may be removed. In some embodiments, the liquid-liquid separation may be a useful tool for removing compounds with low volatility and which typically cannot be easily removed by vapor-liquid separation. For example, chloroethanol (CE), that has a normal boiling point above that of water. Without limitation, the two options for liquid-liquid separator include, but not limited to, a decanter in which the organics formed in the reactor are allowed to separate into a separate phase; and an extraction unit in which additional organic (extractant) is fed to the liquid-liquid separation to assist in the removal of organics with a high affinity for water. In the decanter, the temperature may be between the reactor and electrochemical cell temperatures, i.e. between 70-175° C. or between 90-150° C. or between 120-140° C. The additional organic that is fed into the extraction unit may have requirements including, but not limited to, forming a phase separate from the aqueous phase, high affinity for organic components, separability from the other organic components and from the aqueous phase at low costs, likely through a difference in volatility (boiling point), and relatively inert relative to reaction with the aqueous metal chloride system. CE may be an example of the extractant with a high affinity for water (tends to remain in the aqueous phase). Other examples of extractants include, but not limited to, ethyl acetate, any ketone or alcohol, EDC, monochloro acetic acid (MCA), dichloro acetic acid (DCA), trichloro acetic acid (TCA), alkane with 4-10 carbon atoms e.g. heptanes or hexane, cycloalkane with 4-10 carbon atoms, e.g. cyclohexane, or combinations thereof. Any extractant known in the art may be used in the extraction unit provided herein. In either the decanter or the extraction case, the organic phase may be removed and fed to the purification subprocess IV to be separated into e.g., EDC and byproducts and the aqueous phase may optionally be continued to a vapor-liquid separation unit III. In some embodiments, the aqueous phase containing the metal ion may be fed directly to the electrochemical system or may be fed to the scrubber IVA.

"The vapor-liquid separator process" or "the vapor-liquid separator system" used herein includes any process or system that separates the volatile components as vapor stream from the liquid stream. In some embodiments, the liquid phase from the reactor is fed directly to the vapor-liquid separator system. The vapor-liquid separation system III may either be a distillation column or a flash drum (a single stage distillation). In the flash drum, volatile components such as EDC may be allowed to leave the vessel as vapor stream. The remaining liquid phase may continue onto organic impurities separation as liquid stream. In addition to water and dissolved salts, this liquid stream may contain residual organic. The flash unit is operated at pressure between 0.5-20 atm or between 1-5 atm and temperature of between 70-175° C. The distillation column may be similar to the flash drum, but may provide multiple stages as well as a condenser at the top of the column and a reboiler at the bottom of the column to result in greater organic removal efficiency and possibly higher water retention in the aqueous phase. Configurations for columns include, but not limited to, rectifying column-condenser at the top and no reboiler at the bottom, column with both condenser and reboiler, and stripping column with only reboiler. The column may be operated at pressure between 0.5-20 atm. In some embodiments, the distillation column may be a rectifying column with packing/trays only above the feed; a stripping column with packing/trays only under the feed; a column with packing/trays above and under the feed.

Various combinations of the process separation and purification steps and corresponding systems as described above, may be combined. For example, the extraction at the liquid-liquid separation step may be combined with distillation at the vapor-liquid separation step; the extraction at the liquid-liquid separation step may be combined with flash at the vapor-liquid separation step; the decanter at the liquid-liquid separation step may be combined with distillation at the vapor-liquid separation step; or the decanter at the liquid-liquid separation step may be combined with flash at the vapor-liquid separation step. In some embodiments, the liquid-liquid separation step is omitted and the liquid stream from the reactor is directly subjected to vapor-liquid separation such as, flash or distillation. In some embodiments, the liquid-liquid separation step is repeated after following the liquid-liquid separation step and the vapor-liquid separation step. In some embodiments, the steps may be reversed such that the vapor-liquid separation step precedes the liquid-liquid separation step. In a given process, each step of FIG. 9B may repeated more than once in the process depending on the organic products and the impurities that need to be separated. Any of the aforementioned combinations may or may not be in combination with compression-cooling unit. Further, any of the aforementioned combinations may or may not be in combination with reaction separation reactor, described above. It is to be understood that various combinations of the separation and purification systems described herein can be combined in order to achieve a high purity organic product and high efficiency of the overall process and all of such embodiments are well within the scope of the invention.

Some combinations of the separation and purification systems or processes are listed in Table II below:

TABLE II

| | Liquid-liquid separation | | Vapor-liquid separation | | |
|---|---|---|---|---|---|
| | Extraction | Decanter | Distillation | Flash | Compression-cooling |
| 1 | X | | X | | X |
| 2 | X | | | X | X |
| 3 | | X | X | | X |
| 4 | | X | | X | X |
| 5 | | | X | | X |
| 6 | | | | X | X |
| 7 | X | | X | | |
| 8 | X | | | X | |
| 9 | | X | X | | |
| 10 | | X | | X | |
| 11 | | | X | | |
| 12 | | | | X | |

It is to be understood that the methods and systems for separation and purification of the stream exiting the reactor illustrated in Table II are not in any particular order and include vapor-liquid separation followed by liquid-liquid separation followed by compression-cooling, or liquid-liquid separation followed by vapor-liquid separation followed by compression-cooling or compression-cooling followed by vapor-liquid separation followed by liquid-liquid separation or vapor-liquid separation followed by compression-cooling followed by liquid-liquid separation etc. Any of the aforementioned methods and systems may be optionally combined with purification subprocess.

As described above, the organic liquid phases obtained from the compression-cooling process I, liquid-liquid separation process II and/or vapor-liquid separation process III may be subjected to purification subprocess IV in the purification subprocess system. "The purification subprocess" or "the purification subprocess system" used herein includes any process or system that further reduces the water content in the organic product. For example, in the purification subprocess, the liquid phase may be subjected to decanter, dehydration, distillation, or combinations thereof. Optionally, the dehydration and distillation may be repeated to obtain optimum results. The order of dehydration and distillation may also vary. For example, the liquid phase may be distilled first followed by dehydration and second distillation; or dehydration-distillation-distillation-dehydration; or dehydration-distillation-distillation; or distillation-distillation-dehydration; etc. The dehydration process may substantially remove water from the liquid phase and the distillation may remove organics such as EDC from other byproducts. The dehydration may be carried out using sorbents such as, but not limited to, molecular sieves. The distillation may be carried out in e.g. distillation columns. The decanter has been explained above.

In some embodiments, the organic liquid phases obtained from the compression-cooling process I, the liquid-liquid separation process II and/or the vapor-liquid separation process III may be subjected to scrubbing process IVA before optionally being subjected to the purification subprocess IV. "The scrubbing process" or "the scrubbing system" used herein includes any process or system that causes or is configured to cause a reaction of an alkali with some organic byproducts and separation of the products. For example only, the scrubber may be a column or tank or a collection of columns with one or more columns containing an alkali such as, but not limited to, hydroxide, such as for example only, caustic (NaOH) which is or are configured to react with some organic byproducts to form other products which may easily be separable. In some embodiments, the sodium hydroxide is obtained from the cathode compartment of the electrochemical cell of the system. For example, the chloroacetaldehydes formed during the formation of EDC from ethylene may be treated with caustic to form sodium formate and/or chloromethanes, such as, but not limited to, methyl chloride, dichloromethane, chloroform, etc. The stream from the scrubber may be fed to a byproduct removal column in which heavier impurities, such as, but not limited to, chloroethanol, sodium formate etc. may leave as a bottom product. The overhead in the column may further be fractionated in a column to remove impurities such as chloromethanes. The liquid phase of the fractionation column may be fed back to the liquid separator unit II such as the decanter to remove for example, an EDC rich phase which may be sent to the purification subprocess unit IV.

Any number of combinations of the compression-cooling process/system I, the liquid-liquid separation process/system II, the vapor-liquid separation process/system III, the scrubbing process/system IVA and/or the purification subprocess/system IV may be employed in the separation and purification of the products so long as the halogenated hydrocarbon is separated with a yield of more than 80%, or more than 90%, or more than 95%, or between 80-99%, or between 80-99.9%. In some embodiments, the combinations of the various systems results in the purity of the product of more than 80%, or more than 90%, or more than 95%, or between 80-99%, or between 80-99.9%. In some embodiments, the combinations of the various systems result in the aqueous phase or the metal ion solution with less than 0.1% or less than 1% organic compound, or between 0.001%-1% organic compound. In some embodiments, the metal ion solution is recirculated back to the electrochemical system.

As illustrated in FIG. 9A, after step B is step C where, in some embodiments, the separation of the remaining organic products from the metal ions in the aqueous medium is carried out using adsorbents. In some embodiments, step C may be omitted and the aqueous medium from step B may go directly to electrochemical cell.

The "adsorbent" as used herein includes a compound that has a high affinity for the organic compounds and none or very low affinity for the metal ions. In some embodiments, the adsorbent does not have or has very low affinity for water in addition to none or low affinity for metal ions. Accordingly, the adsorbent may be a hydrophobic compound that adsorbs organics but repels metal ions and water. The "organic" or "organic compound" or "organic products" as used herein includes any compound that has carbon in it.

In some embodiments, the foregoing methods include using adsorbents such as, but not limited to, activated charcoal, alumina, activated silica, polymers, etc., to remove the organic products from the metal ion solution. These adsorbents are commercially available. Examples of activated charcoal that can be used in the methods include, but not limited to, powdered activated charcoal, granular activated charcoal, extruded activated charcoal, bead activated carbon, impregnated carbon, polymer coated carbon, carbon cloth, etc. The "adsorbent polymers" or "polymers" used in the context of the adsorbent herein includes polymers that have high affinity for organic compounds but none or low affinity for metal ions and water. Examples of polymer that can be used as adsorbent include, but not limited to, polyolefins. The "polyolefin" or "polyalkene" used herein includes a polymer produced from an olefin (or an alkene) as a monomer. The olefin or the alkene may be an aliphatic compound or an aromatic compound. Examples include, but not limited to, polyethylene, polypropylene, polystyrene, polymethylpentene, polybutene-1, polyolefin elastomers, polyisobutylene, ethylene propylene rubber, polymethylacrylate, poly(methylmethacrylate), poly(isobutylmethacrylate), and the like.

In some embodiments, the adsorbent used herein adsorbs more than 90% w/w organic compounds; more than 95% w/w organic compounds; or more than 99% w/w; or more than 99.99% w/w organic compounds; or more than 99.999% w/w organic compounds, from the aqueous medium containing metal ions, organic compounds, and water. In some embodiments, the adsorbent used herein adsorbs less than 2% w/w metal ions; or less than 1% w/w metal ions; or less than 0.1% w/w metal ions; or less than 0.01% w/w metal ions; or less than 0.001% w/w metal ions from the aqueous medium containing metal ions, organic compounds, and water. In some embodiments, the adsorbent used herein does not adsorb metal ions from the aqueous medium.

In some embodiments, the aqueous medium obtained after passing through the adsorbent and/or obtained after using the separation/purification systems provided herein (and that is recirculated back to the electrochemical cell) contains less than 1000 ppm or less than 800 ppm or less than 500 ppm or less than 250 ppm or less than 100 ppm, or less than 50 ppm, or less than 10 ppm, or less than 1 ppm, of the organic compound.

The adsorbent may be used in any shape and form available commercially. For example, in some method and system embodiments, the adsorbent is a powder, plate, mesh, beads, cloth, fiber, pills, flakes, blocks, and the like. In some method and system embodiments, the adsorbent is in the form of a bed, a packed column, and the like. In some method and system embodiments, the adsorbent may be in the form of series of beds or columns of packed adsorbent material. For example, in some method and system embodiments, the adsorbent is one or more of packed columns (arranged in parallel or in series) containing activated charcoal powder, polystyrene beads or polystyrene powder.

In some method and system embodiments, the adsorbent is regenerated (step E in FIG. 9A) after the adsorption of the organic products by using various desorption techniques including, but not limited to, purging with an inert fluid (such as water), change of chemical conditions such as pH, increase in temperature, reduction in partial pressure, reduction in the concentration, purging with inert gas at high temperature, such as, but not limited to, purging with steam, nitrogen gas, argon gas, or air at >100° C., etc. In some embodiments, the anode electrolyte exiting the electrochemical cell system (with higher concentration of the metal ion in the higher oxidation state than the metal ion solution entering the anode electrolyte) may be used to regenerate the adsorbent or the adsorption column before the anode electrolyte is sent to the reactor for reaction with the unsaturated or saturated hydrocarbon. The use of the anode electrolyte for the regeneration of the adsorbent may reduce the amount of external fluids needed for the process, thereby favorably affecting the overall economics of the process. The use of the anode electrolyte in the regeneration process may also assist in heat integration of the whole process as described below.

In some method and system embodiments, the adsorbent may be disposed, burnt, or discarded after the desorption process. In some method and system embodiments, the adsorbent is reused in the adsorption process after the desorption. In some method and system embodiments, the adsorbent is reused in multiple adsorption and regeneration cycles before being discarded. In some method and system embodiments, the adsorbent is reused in one, two, three, four, five, or more adsorption and regeneration cycles before being discarded.

In some embodiments, the removal of the organic products and impurities in the decanter during the liquid-liquid separation process/system II in FIG. 9B, allows the adsorption backwash/regeneration to be fed back to the reactor maintaining water/salt balance and avoiding losses of either.

In some embodiments, the electrochemical cell system, the reactor, and the separation/purification systems described herein may also be integrated with heat exchange systems in order to increase the heat efficiency and economics of the system. The "heat exchange process" or "heat exchange system" used herein include process or system that causes or is configured to cause the heating or cooling of the streams of the process. The lesser amount of external heat used during the system is beneficial since it lowers the energy load or electricity consumption of the process. The heat efficiency may also make the process environment friendly leading to greener chemicals generated during the process.

In some embodiments of the methods and systems described herein, the average temperature of the electrochemical system (and therefore the temperature of the entering and exiting anode electrolyte with the metal ions) is between 55-105° C., or between 65-100° C., or between 70-95° C., or between 80-95° C., or between 70-85° C., or 70° C., or 80° C., or 85° C., or 90° C. In some embodiments, the average temperature of the reactor (and hence the entering anode electrolyte and ethylene gas to the reactor and exiting aqueous solution from the reactor containing the one or more organic compounds comprising halogenated hydrocarbon and the metal ions) is between 135-180° C., or between 135-175° C., or between 140-180° C., or between 140-170° C., or between 140-160° C., or between 150-180° C., or between 150-170° C., or between 150-160° C., or between 155-165° C., or 140° C., or 150° C., or 160° C., or 170° C. The heat gradient between the electrochemical system and the reactor allows for one or more heat exchanges between the streams entering and exiting the electrochemical and reactor systems during the process thereby reducing the overall heat requirement of the process or the system. In addition to the temperature gradient between the electrochemical process and the reactor process, there may be heat released or absorbed during various steps of the processes depending on the thermodynamic requirements of the processes. This may lead to hotter or cooler streams during the process which heat may be exchanged during the process to reduce the overall external heat needed during the process.

In some embodiments, the electrochemical cell system, the reactor, and the separation/purification systems described herein are connected via heat exchange systems in such a way that the overall process is self-sustainable and may not require additional heat source. In some embodiments, the overall heat exchanges of the process is in such a way that not more than 1 ton steam or not more than 0.7 ton steam or not more than 0.5 ton steam is required per ton of the organic product produced. For example, in some embodiments, the overall heat integration of the process is in such a way that not more than 1 ton steam or not more than 0.7 ton steam or not more than 0.5 ton steam is required per ton of the EDC produced. The streams in the entire process may be integrated in such a way that the streams from one system may heat or cool the streams of the other systems depending on the temperature requirement.

Accordingly, in some embodiments, there is provided a method including contacting an anode with an anode electrolyte wherein the anode electrolyte comprises metal ion, oxidizing the metal ion from a lower oxidation state to a higher oxidation state at the anode, reacting an unsaturated or saturated hydrocarbon with the anode electrolyte comprising the metal ion in the higher oxidation state in an aqueous medium, to form one or more organic compounds comprising halogenated or sulfonated hydrocarbon and the metal ion in the lower oxidation state, separating and purifying the one or more organic compounds comprising halogenated or sulfonated hydrocarbon, and integrating one or more heat exchange(s) between the entering and exiting streams of processes. In some embodiments, there is provided a method including contacting an anode with an anode electrolyte wherein the anode electrolyte comprises metal ion, oxidizing the metal ion from a lower oxidation state to a higher oxidation state at the anode, reacting an unsaturated or saturated hydrocarbon with the anode electrolyte comprising the metal ion in the higher oxidation state in an aqueous medium, to form one or more organic compounds comprising halogenated or sulfonated hydrocarbon and the metal ion in the lower oxidation state, separating and purifying the one or more organic compounds comprising halogenated or sulfonated hydrocarbon using processes including, but not limited to, compression-cooling process, liquid-liquid separation process, vapor-liquid separation process, scrubbing process, purification subprocess, and combinations thereof, and integrating one or more heat exchange(s) between the entering and exiting streams of processes.

In some embodiments, the entering and exiting streams of processes stated above include, but not limited to, the anode electrolyte, the unsaturated or saturated hydrocarbon, the aqueous medium comprising the metal ion in the lower and higher oxidation state, steam, water, or combinations thereof. In some embodiments, the one or more heat exchange(s) between the entering and exiting streams of processes includes the heat exchange between the exiting anode electrolyte from the electrochemical process and the exiting aqueous medium from the reactor comprising the one or more organic compounds comprising halogenated hydrocarbon and the metal ions. In some embodiments of the aforementioned embodiments, the integration of the one or more heat exchange(s) between the entering and exiting streams of processes, reduces the external heat requirement to less than 1 ton of steam per ton of the organic compound/product produced. For example, in some embodiments of the aforementioned embodiments, the integration of the one or more heat exchange(s) between the entering and exiting streams of processes, reduces the external heat requirement to less than 1 ton of steam per ton of the EDC produced. Various examples of the one or more heat exchange(s) between the entering and exiting streams of processes are described herein below.

In some embodiments of the foregoing methods, the method further comprises recirculating the aqueous medium comprising metal ion in the lower oxidation state and the metal ion in the higher oxidation state back to the anode electrolyte. In some embodiments of the foregoing methods, the unsaturated hydrocarbon, the saturated hydrocarbon, the halogenated hydrocarbon, the metal ions, etc. have all been described in detail herein. In some embodiments of the foregoing methods, the metal ion is copper, the unsaturated hydrocarbon is ethylene and the organic compound comprises EDC. In some embodiments of the foregoing methods, the method further includes reaction separation as described above, and/or remaining organic separation (adsorbent in step C) as described further herein below.

In some embodiments, there is provided a system, comprising an anode in contact with an anode electrolyte comprising metal ion wherein the anode is configured to oxidize the metal ion from a lower oxidation state to a higher oxidation state; a reactor operably connected to the anode chamber and configured to cause reaction of an unsaturated hydrocarbon or saturated hydrocarbon in an aqueous medium with the anode electrolyte comprising the metal ion in the higher oxidation state to form one or more organic compounds comprising halogenated or sulfonated hydrocarbon and the metal ion in the lower oxidation state; a separator configured to separate and purify the one or more organic compounds comprising halogenated or sulfonated hydrocarbon; and one or more heat exchange units configured to cause heat exchange(s) between the entering and exiting streams of the systems. In some embodiments, there is provided a system, comprising an anode in contact with an anode electrolyte comprising metal ion wherein the anode is configured to oxidize the metal ion from a lower oxidation state to a higher oxidation state; a reactor operably connected to the anode chamber and configured to cause reaction of an unsaturated hydrocarbon or saturated hydrocarbon in an aqueous medium with the anode electrolyte comprising the metal ion in the higher oxidation state to form one or more organic compounds comprising halogenated or sulfonated hydrocarbon and the metal ion in the lower oxidation state; a separator configured to separate and purify the one or more organic compounds comprising halogenated or sulfonated hydrocarbon using systems including, but not limited to, compression-cooling system, liquid-liquid separator system, vapor-liquid separator system, scrubbing system, purification subprocess system, and combinations thereof; and one or more heat exchange units configured to cause heat exchange(s) between the entering and exiting streams of the systems. In some embodiments of the aforementioned embodiments, the one or more heat exchange units are configured to exchange heat between the anode electrolyte, the unsaturated or saturated hydrocarbon, the aqueous medium comprising the metal ion in the lower and higher oxidation state, steam, water, or combinations thereof.

In some embodiments, the one or more heat exchange(s) units between the entering and exiting streams of systems includes the heat exchange unit between the exiting anode electrolyte from the electrochemical system and the exiting aqueous medium from the reactor comprising the one or more organic compounds comprising halogenated hydrocarbon and the metal ions. In some embodiments of the aforementioned embodiments, the one or more heat exchange(s) units between the entering and exiting streams of systems, reduces the external heat requirement to less than 1 ton of steam per ton of the organic compound/product produced. For example, in some embodiments of the aforementioned embodiments, the one or more heat exchange(s) units between the entering and exiting streams of the systems, reduces the external heat requirement to less than 1 ton of steam per ton of the EDC produced. Various examples of the one or more heat exchange(s) units between the entering and exiting streams of the systems are described herein below.

In some embodiments of the foregoing systems, the unsaturated hydrocarbon, the saturated hydrocarbon, the halogenated hydrocarbon, the metal ions, etc. have all been described in detail herein. In some embodiments of the foregoing systems, the metal ion is copper, the unsaturated hydrocarbon is ethylene and the organic compound comprises EDC. In some embodiments of the foregoing systems, the system further includes reaction separation reactor (e.g. distillation reactor or extraction reactor) as described above, and/or remaining organic separator (adsorbent in step C) as described further herein below.

The heat exchange system can be any unit configured to exchange heat between the streams. The heat exchange unit may be a double walled hollow tube, pipe or a tank to let the two streams pass each other counter-currently inside the tube separated by a wall so that the heat exchange may take place. In some embodiments, the tube may comprise one or more smaller tubes such that the streams flow counter currently through several hollow tubes inside one main tube. The material of the tube or the pipe may be corrosion resistant such as made from titanium. In some embodiments, the inner tube is made from titanium and not the outer tube or vice versa depending on the stream passing through the tube. For example only, the stream from the electrochemical system containing the metal ions may need a corrosion resistant material but the tube carrying hot water may not need to be corrosion resistant.

Without limitation, some examples of the one or more heat exchange(s) units between the entering and exiting streams of the systems are as described herein. While the exiting hotter stream of the catalysis reactor may be used to heat the relatively cooler stream exiting from the electrochemical system (and in turn cool itself down), both the exiting hot streams from the electrochemical as well as the reactor system can be used to heat the ethylene gas and/or distillation columns or other columns in the separation/purification systems of the invention. Similarly, the ethylene gas may be used to cool the condenser portion of the distillation columns in the system. Example of another hot stream is the sodium hydroxide solution generated in the cathode compartment of the electrochemical system which may be used to heat ethylene gas entering the reactor, heat the solution entering the distillator of the vapor-liquid separation system, heat the fractionation distillation column of the scrubber system, or combinations thereof. In some embodiments, cold water may be needed to cool the stream such as to cool the condenser portion of the distillation column. In some embodiments, steam may be needed to heat the stream but as noted above, no more than 1 ton of steam may be needed per ton of the organic product produced in the system or the process.

An illustrative example of the systems and methods of the invention including, but not limited to, the electrochemical cell, the reactor, the separation and purification system including but not limited to, the liquid-liquid separation II (as in FIG. 9B), the vapor-liquid separation III, the scrubbing IVA, the purification subprocess IV, the adsorbent, and the heat exchange units, is as illustrated in FIG. 9C. It is to be understood that FIG. 9C is for illustration purposes only and shows ethylene as an example of the unsaturated hydrocarbon. This process may be applied to any unsaturated or saturated hydrocarbon as described herein. Further, the components shown in the figure are also for illustrative purposes only. Many variations of such separation/purification systems and heat exchange units including change in the order of the systems and/or addition or removal of some systems, are applicable to the process and all are well within the scope of the invention.

As shown in FIG. 9C, sodium chloride 1 and water 2 along with a recycled stream of CuCl-rich aqueous solution 31 may be fed to an electrochemical process, producing aqueous sodium hydroxide 3 and hydrogen gas 5 at a cell temperature between 55-105° C., or between 65-100° C., or between 70-95° C., or between 80-95° C., or between 70-85° C., or 70° C., or 80° C., or 85° C., or 90° C. The hot sodium hydroxide solution possesses heat that may be utilized in a heat exchanger for heating other streams, such as, but not limited to, ethylene or the distillation columns.

In the anode chamber of the electrochemical cell, CuCl in stream 31 is converted to $CuCl_2$. The $CuCl_2$ stream may be warmed in a heat exchanger HX03, exchanging heat with the reactor effluent 15. The $CuCl_2$ stream may be warmed by a series of heat exchanging units in order to achieve the optimum temperature for entering the reactor. In some embodiments, the CuCl$_2$ stream may be used to regenerate a spent adsorption bed by passing it through the bed which may strip organic from the bed (e.g. ethylene dichloride and chloroethanol along with other byproducts) which may be then pumped through heat exchanger to the reactor (not shown in the figure). This hot stream 10 may be optionally heated with steam (if more heating is required) and fed to the EDC production reactor. Ethylene is fed to the process as stream 12. This cold stream 12 requires heat to reach reactor temperature and in turn can be used to provide cooling elsewhere in the process. The heating of stream 12 can be achieved by using it to cool NaOH 3 or EDC product 29. In some embodiments, ethylene may additionally be heated using steam.

Following the heat exchange in HX03, the cooler reactor effluent 15 containing the one or more organic compounds and metal ions may be subjected to liquid-liquid separation process using a decanter, when an organic phase is removed as 18. The aqueous phase 19 may be subjected to a vapor-liquid separation process and may be passed through a distillation column, in which organics are stripped at an overhead stream, leaving the salt-containing aqueous stream 30 to pass to the adsorption column in which the organic content may be further reduced prior to return to the electrochemical cells as stream 31.

The organic phase from the decanter 18 and organic stripper overhead 20 may be fed to a scrubber, such as caustic scrubber 21 in which NaOH may react with byproducts, such as, but not limited to, chloroacetaldehydes, producing products such as, aqueous sodium formate and chloromethanes (e.g. methyl chloride, dichloromethane, chloroform). It is to be understood that any chemical other than sodium hydroxide may be used depending on the desired reaction and also dependent on the organic products. The product of the caustic scrubber may be fed to a byproduct removal column in which heavier impurities, such as but not limited to, chloroethanol and sodium formate may leave as a bottom product 23. The overhead 24 from this scrubbing system (scrubber and byproduct removal column) may then be sent to the purification subprocess system containing distillation column, decanter and dehydration column.

In some embodiments, the scrubber may be replaced with a flash distillation (vapor-liquid separation) where the organics are removed by incineration and the aqueous phase is sent to the byproduct removal column.

The overhead 24 may be fractionated in a distillation column, resulting in an overhead 25 containing chloromethanes which may be incinerated or sold as a product. The bottom of the column, stream 26, may be fed to a decanter, which may remove an EDC-rich phase 28 containing less than 2 wt % of water. This EDC phase may be subjected to dehydration on a drying bed, to form substantially pure EDC 29. The drying bed may, for example, be molecular sieves. The water 27 may contain some EDC and may be fed back to the byproduct removal column, with the water eventually leaving with stream 23 for treatment, and the EDC being largely recovered in overhead 24. In some embodiments, the water 27 may be sent to membrane or activated carbon bed to remove water from the remaining byproducts which are further incinerated.

While this figure illustrates streams and components of the ethylene reaction to form EDC, variations from this figure including other separation and purifications systems, more heat exchange units, and other inflow and outflow of the streams are all well within the scope of the invention.

Referring back to FIG. 9A, after step C is step D where, in some embodiments, the metal salts with metal ions in the lower oxidation state are separated from the metal salts with metal ions in the higher oxidation state. In some embodiments, step D may be omitted such that the aqueous medium from step B may or may not go through step C before entering the electrochemical cell. As described herein, the metal salt solution after the separation of the organic products is sent back to the electrochemical cell for the oxidation of the metal ion from the lower oxidation state to the higher oxidation state. Applicants have unexpectedly and surprisingly found that the desired concentration and/or the ratio of the metal ions in the lower oxidation state and the metal ions in the higher oxidation state, is different in the electrochemical system from that in the reactor system. For example only, lower voltage is observed for electrochemical system run with higher concentration of the metal ion in the lower oxidation state such as, e.g. high Cu(I) concentration and higher selectivity is observed in the reactor system run with higher concentration of the metal ion in the higher oxidation state such as, e.g. higher Cu(II) concentrations. Therefore, in some embodiments, the metal ion in the higher oxidation state may be partially or fully separated from the metal ion in the lower oxidation state before feeding the metal ion solution containing predominantly metal in the lower oxidation state to the electrochemical system. The metal solution from the electrochemical system may be replenished with more metal ion in the higher oxidation state before the metal solution is fed into the reactor system, as illustrated in FIG. 9A.

Accordingly, in some embodiments, there is provided a method including contacting an anode with an anode electrolyte wherein the anode electrolyte comprises metal ion, oxidizing the metal ion from a lower oxidation state to a higher oxidation state at the anode, reacting an unsaturated or saturated hydrocarbon with the anode electrolyte comprising the metal ion in the higher oxidation state in an aqueous medium, to form one or more organic compounds comprising halogenated hydrocarbon and the metal ion in the lower oxidation state, and separating the metal ion in the lower oxidation state from the metal ion in the higher oxidation state before circulating the aqueous medium comprising the metal ion in the lower oxidation state back to the anode electrolyte. In some embodiments of the foregoing methods, the aqueous medium that is circulated back to the anode electrolyte comprises substantially only the metal ion in the lower oxidation state and no or very low concentration (less than 3M, or less than 2M, or less than 1M or less than 0.5M) of the metal ion in the higher oxidation state. In some embodiments of the foregoing methods, the unsaturated hydrocarbon, the saturated hydrocarbon, the halogenated hydrocarbon, the metal ions, etc. have all been described in detail herein. In some embodiments of the foregoing methods, the metal ion is copper, the unsaturated hydrocarbon is ethylene and the organic compound comprises EDC. In some embodiments of the foregoing methods, the method further includes reaction separation as described above, and/or remaining organic separation (step C) as described above. In some embodiments of the foregoing methods, the method further includes separating and purifying (step B) the one or more organic compounds comprising halogenated hydrocarbon using processes including, but not limited to, compression-cooling process, liquid-liquid separation, vapor-liquid separation, and combinations thereof.

In some embodiments, there is provided a system, comprising an anode in contact with an anode electrolyte comprising metal ion wherein the anode is configured to oxidize the metal ion from a lower oxidation state to a higher oxidation state; a reactor operably connected to the anode chamber and configured to cause reaction of an unsaturated hydrocarbon or saturated hydrocarbon in an aqueous medium with the anode electrolyte comprising the metal ion in the higher oxidation state to form one or more organic compounds comprising halogenated hydrocarbon and the metal ion in the lower oxidation state; and a metal separator configured to separate the metal ion in the lower oxidation state from the metal ion in the higher oxidation state before circulating the aqueous medium comprising the metal ion in the lower oxidation state back to the anode electrolyte. In some embodiments of the foregoing systems, the metal separator is configured to separate the metal ions such that the aqueous medium that is circulated back to the anode electrolyte comprises substantially only the metal ion in the lower oxidation state and no or very low concentration (less than 3M, or less than 2M, or less than 1M or less than 0.5M) of the metal ion in the higher oxidation state. In some embodiments of the foregoing systems, the unsaturated hydrocarbon, the saturated hydrocarbon, the halogenated hydrocarbon, the metal ions, etc. have all been described in detail herein. In some embodiments of the foregoing systems, the metal ion is copper, the unsaturated hydrocarbon is ethylene and the organic compound comprises EDC. In some embodiments of the foregoing systems, the system further includes reaction separation reactor as described above, and/or remaining organic separator (adsorbent) as described further herein below. In some embodiments of the foregoing systems, the system further includes a separator configured to separate and purify the one or more organic compounds comprising halogenated hydrocarbon using systems including, but not limited to, compression-cooling system, liquid-liquid separator, vapor-liquid separator, and combinations thereof.

The metal separation or the metal separator system may include, but not limited to, precipitation, nanofiltration, kinetic dissolution, or combinations thereof. In some embodiments, the metal ions are separated by precipitation technique. In the methods and systems provided herein, the electrochemical cells are run at lower temperature than the reactors. Therefore, the metal solution exiting the reactor may need to be cooled down before being fed into the electrochemical system. In some embodiments, the cooling of the metal solution may result in the precipitation of the metal ions. Depending on the solubility differences between the metal ions in the lower oxidation state and the metal ions in the higher oxidation state, the metal ions in the two different oxidations states may be separated. For example only, in the Cu(I)/Cu(II) solution system, the reactor may operate at ~150° C. while the electrochemical system may operate at much lower temperature, e.g. ~70° C. Therefore, the copper solution needs to be cooled before feeding into the electrochemical cell. It was observed that the cooling of the copper solution resulted in the precipitation of the Cu(II) salt as compared to the Cu(I) salt (an experiment described in Example 6 below). The Cu(I) salt solution thus obtained may be fed into the electrochemical cell. The solid containing the Cu(II) may be used to supplement the metal solution exiting the electrochemical cell and entering the reactor.

In some embodiments, the metal ions are separated by nanofiltration. Nanofiltration (NF) is a membrane filtration process which uses diffusion through a membrane, under pressure differentials that may be considerable less than those for reverse osmosis. NF membranes may have a slightly charged surface, with a negative charge at neutral pH. This surface charge may play a role in the transportation mechanism and separation properties of the membrane. For example only, Sterlitech CF042 membrane cell is a lab scale cross flow filtration unit. In this unit, a single piece of rectangular NF membrane is installed in the base of the cell and a polytetrafluoroethylene (PTFE) support membrane is used as a permeate carrier. In a typical operation, a feed stream is pumped from the feed vessel to the feed inlet, which is located on the cell bottom. Flow continues through a manifold into the membrane cavity. Once in the cavity, the solution flows tangentially across the membrane surface. A portion of the solution permeates the membrane and flows through the permeate carrier, which is located on top of the cell. The permeate flows to the center of the cell body top, is collected in a manifold and then flows out of the permeate outlet connection into a collection vessel. The concentrate stream, which contains the material rejected by the membrane, continues sweeping over the membrane then flows out of the concentrate tube back into the feed vessel. Examples of other NF membranes, without limitation include, Dow NF (neutral), Dow NF90 (neutral), Dow NF270 (neutral), TriSep XN45 (neutral), Koch HFM-183 (positively charged), Koch HFP-707 (negatively charged), CEM 2030, FAA130, and FAS130.

In some embodiments, the metal ions are separated by kinetic or transient dissolution technique. In this technique, metal ions that have different kinetics of dissolution can be separated. For example, Cu(II) dissolves faster than Cu(I). Example 7 described herein illustrates the separation of Cu(I) from Cu(II) using kinetics of their dissolution.

In some embodiments, the reactor and/or separator components in the systems of the invention may include a control station, configured to control the amount of the hydrocarbon introduced into the reactor, the amount of the anode electrolyte introduced into the reactor, the amount of the aqueous medium containing the organics and the metal ions into the separator, the adsorption time over the adsorbents, the temperature and pressure conditions in the reactor and the separator, the flow rate in and out of the reactor and the separator, the regeneration time for the adsorbent in the separator, the time and the flow rate of the aqueous medium going back to the electrochemical cell, etc.

The control station may include a set of valves or multivalve systems which are manually, mechanically or digitally controlled, or may employ any other convenient flow regulator protocol. In some instances, the control station may include a computer interface, (where regulation is computer-assisted or is entirely controlled by computer) configured to provide a user with input and output parameters to control the amount and conditions, as described above.

The methods and systems of the invention may also include one or more detectors configured for monitoring the flow of the ethylene gas or the concentration of the metal ion in the aqueous medium or the concentration of the organics in the aqueous medium, etc. Monitoring may include, but is not limited to, collecting data about the pressure, temperature and composition of the aqueous medium and gases. The detectors may be any convenient device configured to monitor, for example, pressure sensors (e.g., electromagnetic pressure sensors, potentiometric pressure sensors, etc.), temperature sensors (resistance temperature detectors, thermocouples, gas thermometers, thermistors, pyrometers, infrared radiation sensors, etc.), volume sensors (e.g., geophysical diffraction tomography, X-ray tomography, hydroacoustic surveyers, etc.), and devices for determining chemical makeup of the aqueous medium or the gas (e.g, IR spectrometer, NMR spectrometer, UV-vis spectrophotometer, high performance liquid chromatographs, inductively coupled plasma emission spectrometers, inductively coupled plasma mass spectrometers, ion chromatographs, X-ray diffractometers, gas chromatographs, gas chromatography-mass spectrometers, flow-injection analysis, scintillation counters, acidimetric titration, and flame emission spectrometers, etc.).

In some embodiments, detectors may also include a computer interface which is configured to provide a user with the collected data about the aqueous medium, metal ions and/or the organics. For example, a detector may determine the concentration of the aqueous medium, metal ions and/or the organics and the computer interface may provide a summary of the changes in the composition within the aqueous medium, metal ions and/or the organics over time. In some embodiments, the summary may be stored as a computer readable data file or may be printed out as a user readable document.

In some embodiments, the detector may be a monitoring device such that it can collect real-time data (e.g., internal pressure, temperature, etc.) about the aqueous medium, metal ions and/or the organics. In other embodiments, the detector may be one or more detectors configured to determine the parameters of the aqueous medium, metal ions and/or the organics at regular intervals, e.g., determining the composition every 1 minute, every 5 minutes, every 10 minutes, every 30 minutes, every 60 minutes, every 100 minutes, every 200 minutes, every 500 minutes, or some other interval.

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Various modifications of the invention in addition to those described herein will become apparent to those skilled in the art from the foregoing description and accompanying figures. Such modifications fall within the scope of the appended claims. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

In the examples and elsewhere, abbreviations have the following meanings:

| | | |
|---|---|---|
| AEM | = | anion exchange membrane |
| Ag | = | silver |
| Ag/AgCl | = | silver/silver chloride |
| $cm^2$ | = | centimeter square |
| ClEtOH | = | chloroethanol |
| CV | = | cyclic voltammetry |
| DI | = | deionized |
| EDC | = | ethylene dichloride |
| g | = | gram |
| HCl | = | hydrochloric acid |
| h or hr | = | hour |
| Hz | = | hertz |
| kA | = | kiloamps |
| Kg | = | kilogram |
| kHz | = | kilohertz |
| l or L | = | liter |
| M | = | molar |
| mA | = | milliamps |
| $mA/cm^2$ | = | milliamps/centimeter square |
| mg | = | milligram |
| min | = | minute |
| mmol | = | millimole |
| mol | = | mole |
| μl | = | microliter |
| μm | = | micrometer |
| ml | = | milliliter |
| ml/min | = | milliliter/minute |
| mV | = | millivolt |
| mV/s or $mVs^{-1}$ | = | millivolt/second |
| NaCl | = | sodium chloride |
| NaOH | = | sodium hydroxide |
| nm | = | nanometer |
| $\Omega cm^2$ | = | ohms centimeter square |
| Pd/C | = | palladium/carbon |
| psi | = | pounds per square inch |
| psig | = | pounds per square inch guage |
| Pt | = | platinum |
| PtIr | = | platinum iridium |
| rpm | = | revolutions per minute |
| STY | = | space time yield |
| V | = | voltage |
| w/v | = | weight/volume |
| w/w | = | weight/weight |

EXAMPLES

Example 1

Formation of Halohydrocarbon from Unsaturated Hydrocarbon

Formation of EDC from Ethylene Using Copper Chloride

This experiment is directed to the formation of ethylene dichloride (EDC) from ethylene using cupric chloride. The experiment was conducted in a pressure vessel. The pressure vessel contained an outer jacket containing the catalyst, i.e. cupric chloride solution and an inlet for bubbling ethylene gas in the cupric chloride solution. The concentration of the reactants was, as shown in Table 1 below. The pressure vessel was heated to 160° C. and ethylene gas was passed into the vessel containing 200 mL of the solution at 300 psi for between 30 min-1 hr in the experiments. The vessel was cooled to 4° C. before venting and opening. The product formed in the solution was extracted with ethyl acetate and was then separated using a separatory funnel. The ethyl acetate extract containing the EDC was subjected to gas-chromatography (GC).

TABLE 1

| Time (hrs) | $CuCl_2$ | CuCl | NaCl | HCl (M) | EDC (mg) | Chloroethanol (mg) | Cu Utilization (EDC) | STY | Mass Selectivity: EDC/(EDC + ClEtOH) % |
|---|---|---|---|---|---|---|---|---|---|
| 0.5 | 6 | 0.5 | 1 | 0.03 | 3,909.26 | 395.13 | 8.77% | 0.526 | 90.82% |
| 0.5 | 4.5 | 0.5 | 2.5 | 0.03 | 3,686.00 | 325.50 | 11.03% | 0.496 | 91.89% |

Formation of Dichloropropane from Propylene Using Copper Chloride

This experiment is directed to the formation of 1,2-dichloropropane (DCP) from propylene using cupric chloride. The experiment was conducted in a pressure vessel. The pressure vessel contained an outer jacket containing the catalyst, i.e. cupric chloride solution and an inlet for bubbling propylene gas in the cupric chloride solution. A 150 mL solution of 5M $CuCl_2$, 0.5M CuCl, 1M NaCl, and 0.03M HCl was placed into a glass-lined 450 mL stirred pressure vessel. After purging the closed container with $N_2$, it was heated to 160° C. After reaching this temperature, propylene was added to the container to raise the pressure from the autogenous pressure, mostly owing from water vapor, to a pressure of 130 psig. After 15 minutes, more propylene was added to raise the pressure from 120 psig to 140 psig. After an additional 15 minutes, the pressure was 135 psig. At this time, the reactor was cooled to 14° C., depressurized, and opened. Ethyl acetate was used to rinse the reactor parts and then was used as the extraction solvent. The product was analyzed by gas chromatography which showed 0.203 g of 1,2-dichloropropane that was recovered in the ethyl acetate phase.

Example 2

Low Voltage of the Electrochemical Reaction

This example illustrates low voltage of the electrochemical reaction when the corrugated anode and PK membrane was used in the electrochemical cell. The cell configuration on the 40 cm² active area lab cell was of Ti-base corrugation bridged with coated Ti mesh anode, Ni flynet meshed cathode with platinum group metal catalyst coating, FAA-3-PK-30 anion exchange membrane (FuMA-Tech), and N2030 cation exchange membrane (Dupont). The cell conditions were an anolyte composed of 4.5 M $CuCl_2$, 1.5M CuCl, 2.5M NaCl, a brine feed of 300 g/NaCl at a pH of 2, and a catholyte of 30 wt % sodium hydroxide. The operating temperature of the cell was 90° C. The run time for the electrochemical reaction was 30 min. These conditions achieved a cell voltage of 2.35V at 3 kA/m².

Example 3

Adsorption of Organics on Adsorbent

Figure 10:
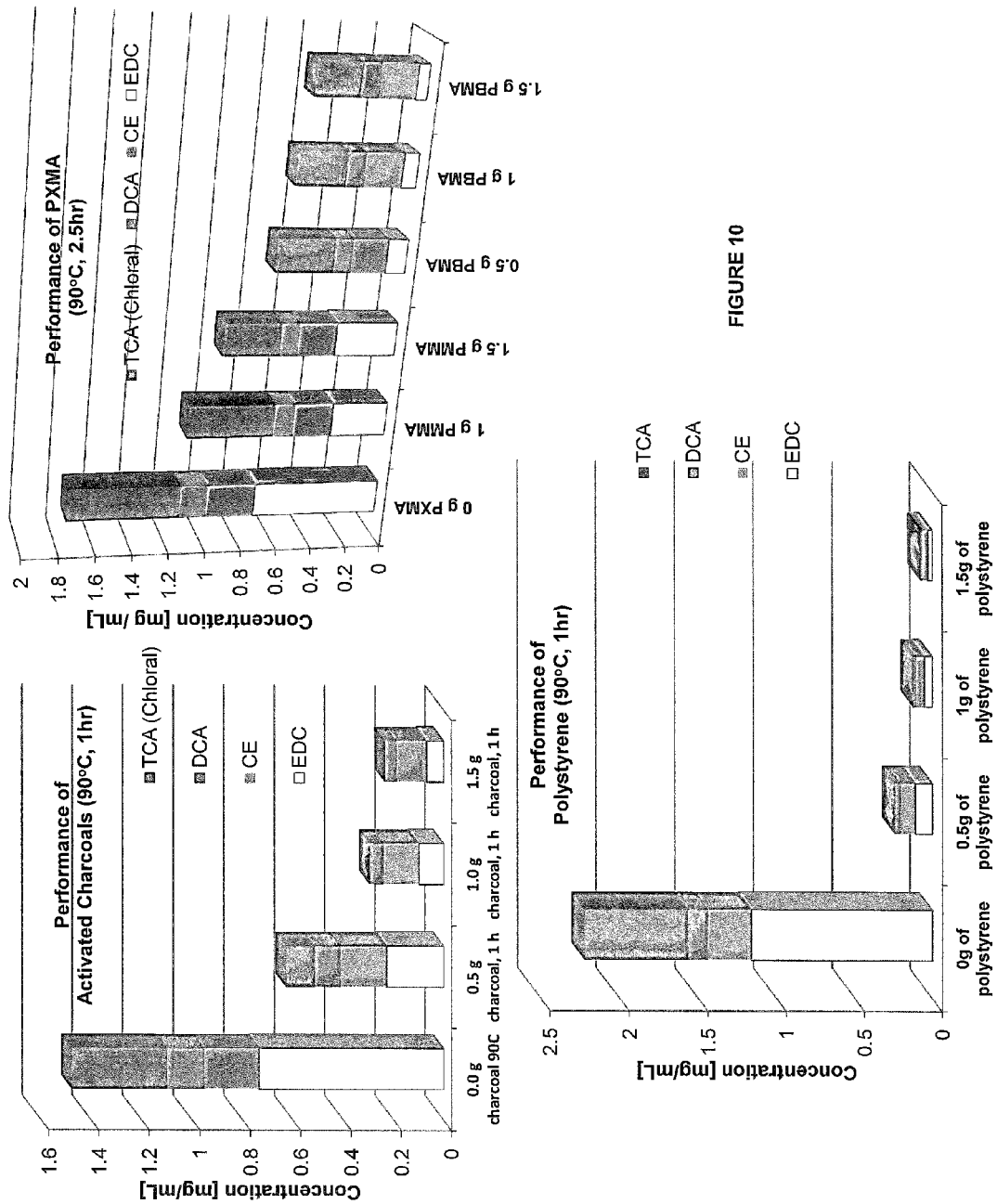
FIG. 10 is an illustrative graph for different adsorbents, as described in Example 3 herein.

In this experiment, the adsorption of the organics from the aqueous metal solution using different adsorbents was tested. The adsorbents tested were: activated charcoal (Aldrich, 20-60 mesh), pelletized PMMA ((poly(methyl methacrylate) average Mw 120,000 by GPC, Aldrich) and pelletized PBMA ((poly(isobutyl methacrylate) average Mw 130,000, Aldrich) (both PMMA and PBMA shown as PXMA in FIG. 10) and cross-linked PS (Dowex Optipore® L-493, Aldrich). The PS (Dowex Optipore® L-493, Aldrich) was 20-50 mesh beads with a surface area of 1100 m²/g, average pore diameter of 4.6 nm, and average crush strength of 500 g/bead.

Static adsorption experiments were performed in 20 mL screw cap vials. An aqueous stock solution containing 4M $CuCl_2(H_2O)_2$, 1M CuCl, and 2M NaCl was doped with small amounts of ethylene dichloride (EDC), chloroethanol (CE), dichloroacetaldehyde (DCA) and trichloroacetaldehyde (TCA). The organic content of the solution was analyzed by extracting the aqueous solution with 1 mL of EtOAc and analyzing the organics concentration of the EtOAc extractant. A 6 mL of the stock solution was stirred at 90° C. with different amounts of adsorbent material for a specific time as indicated in the graph illustrated in FIG. 10. After filtration, the organic content of the treated aqueous solution was analyzed by extraction and GCMS analysis of the organic phase. It was observed that with the increasing amount of the adsorbent material, an increasing reduction of organic content was achieved. The highest reduction was observed with the crosslinked PS.

Figure 11:
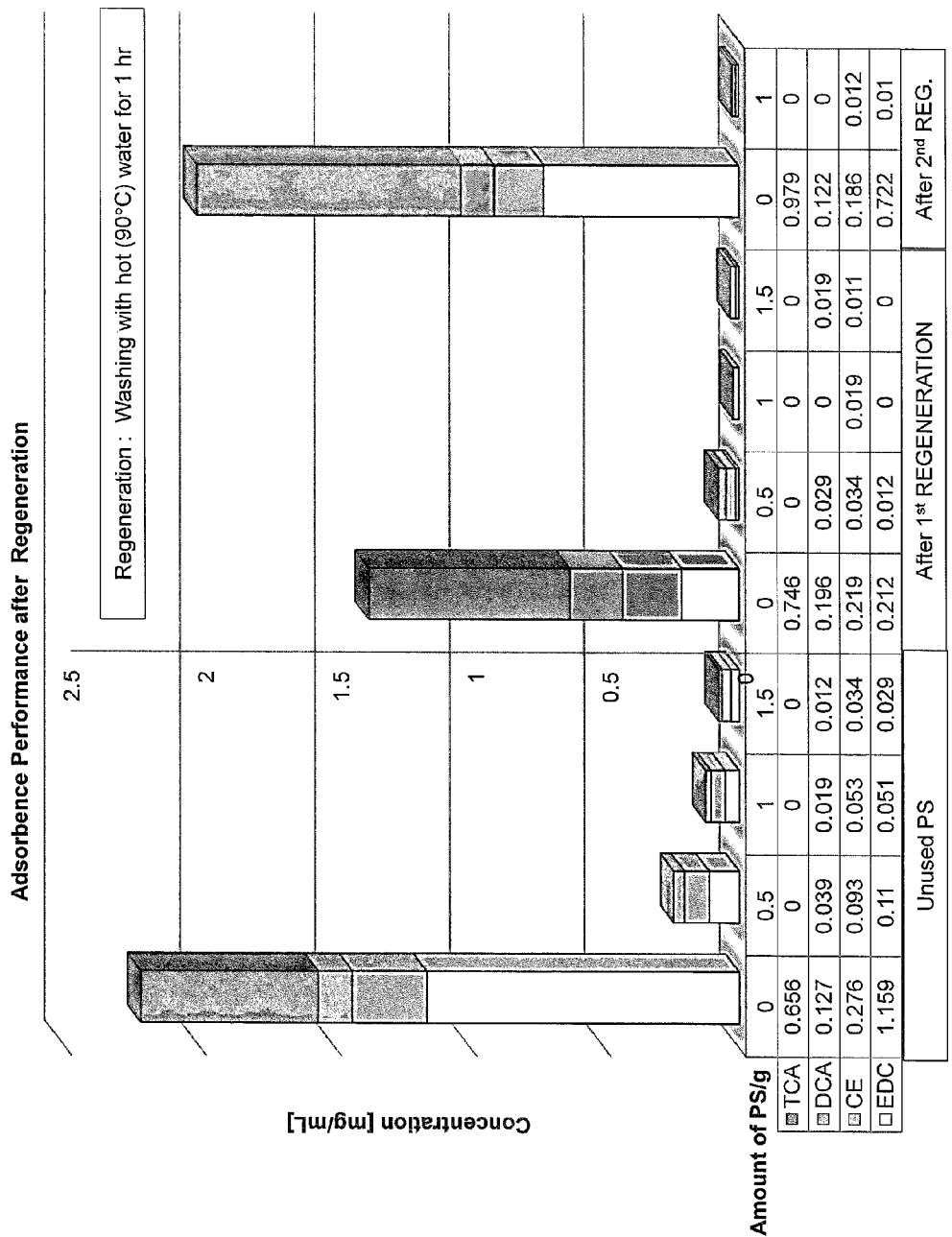
FIG. 11 is an illustrative graph for adsorption and regeneration, as described in Example 3 herein.

In this experiment, the regeneration capability of the adsorbent was tested by repeatedly adsorbing organics from a Cu containing solution on a given adsorbing material (Dowex Optipore® 495-L), washing the material with cold and hot water, drying the material and then using the washed material for adsorption again. Results of the experiment are illustrated in FIG. 11. It was observed that the adsorbance performance even after the second regeneration was very similar to the unused material. It was also observed that ultraviolet (UV) measurement of the Cu concentration after the organics adsorbance with Dowex material did not show significant change. With unused material, around 10% reduction of overall Cu concentration was observed, and with a regenerated material only between 1 and 2% reduction of Cu Concentration was observed. These findings point towards the advantage of the repeated use of the polymeric adsorbing material as the polymeric material adsorbs organics from a copper ion containing solution without retaining the majority of the Cu ions even after multiple use cycles. So the adsorbent material can be regenerated after its adsorption capacity is exhausted and after regeneration the adsorbent material can be reused for the adsorption.

It was observed that the adsorption and desorption profiles and times may be influenced by parameters such as flow rate, temperature, column dimension and others. These parameters can be used to optimize the technique for the removal of organics from the exit stream before entering the electrochemical cell.

Example 4

Corrosion Testing of the Electrochemical Cell

Corrosion testing was conducted for a wide range of metals and polymers (see Table 2) in highly concentrated copper chloride solutions at 90° C. and 160° C. Select materials were also tested with 5 mg/mL ethylene dichloride (EDC). The change in weight was measured after 10 days and 1000 hours. These materials were all candidates for applications in tank materials, piping, heat exchangers, pumps, reactors, cell housings, cell frames, electrodes, instrumentation, valves, and all other balance of plant materials.

TABLE 2

Summary of long term corrosion testing in copper chloride solutions

| Material | CuCl$_2$/CuCl/NaCl (mol/L) | T ° C. | Initial (g) 10 Day | Final (g) 10 Day | Initial (g) 1000 Hours | Final (g) 1000 Hours |
|---|---|---|---|---|---|---|
| Polyvinylidene fluoride | 4.5/0.5/2.5 | 90 | 0.7948 | 0.7954 | 1.3233 | 1.3244 |
| Polyvinylidene fluoride | 5.5/0.5/2.5 + 5 mg/mL EDC | 90 | 0.3955 | 0.3961 | 0.4235 | 0.4238 |
| Polyvinylidene fluoride | 4.5/0.5/2.5 | 160 | 0.4791 | 0.4805 | 0.5941 | 0.5988 (Severe attack) |
| Viton ™ | 4.5/0.5/2.5 | 90 | 1.3341 | 1.3513 | 1.2879 | 1.3287 |
| Polyether ether ketone | 4.5/0.5/2.5 | 90 | 0.4798 | 0.4802 | 0.8595 | 0.8607 |
| Polyether ether ketone | 4.5/0.5/2.5 | 160 | 0.3262 | 0.3265 | 0.4792 | 0.4795 |
| Fluorinated ethylene propylene | 4.5/0.5/2.5 | 90 | 1.3692 | 1.3693 | 1.6849 | 1.6849 |
| Fibre-reinforced plastic | 4.5/0.5/2.5 | 90 | 1.028 | 1.0371 | 1.1164 | 1.1334 |
| Halar ™ | 4.5/0.5/2.5 | 90 | 0.7125 | 0.7125 | 0.74 | 0.7402 |
| Ultem (PEI) | 4.5/0.5/2.5 | 90 | 0.8079 | 0.8093 | 0.8566 | 0.8579 |
| Perfluoroalkoxy | 4.5/0.5/2.5 | 90 | 0.4149 | 0.415 | 0.3931 | 0.3931 |
| Tefzel ™ | 4.5/0.5/2.5 | 90 | 1.0066 | 1.0064 | 1.0066 | 1.0058 |
| Tivar ™ | 4.5/0.5/2.5 | 90 | 0.4725 | 0.4729 | 0.4725 | 0.4727 |
| Fibre-reinforced plastic-coated with Derakane 441-400 resin | 4.5/0.5/2.5 | 90 | 4.4412 | 4.4476 | 4.4412 | 4.4444 |
| Graphite | 5.5/0.5/2.5 | 160 | 1.7623 | 2.002 | 1.7196 | 1.9908 |
| Graphite | 5.5/0.5/2.5 + 5 mg/mL EDC | 160 | 1.7526 | 1.971 | 1.7198 | 1.9694 |
| Akot | 4.5/0.5/2.5 | 160 | 0.4554 | 0.4555 | 0.4604 | 0.46 |
| Tantalum | 4.5/0.5/2.5 | 160 | 3.3288 | 3.3288 | 3.3272 | 3.3272 |
| Hastelloy C2000 | 4.5/0.5/2.5 | 160 | 1.3384 | 0 | 1.3292 | 0 |
| Titanium Gr. 7 | 4.5/0.5/2.5 | 160 | 0.9148 | 0.9148 | 0.8225 | 0.8186 |
| Titanium Gr. 2 | 4/0.9/2.5 | 90 | 7.189 | 7.189 | — | — |
| Titanium Gr. 2 | 4/0.9/2.5 + 0.02M HCl | 90 | 2.5906 | 2.59 | — | — |
| Titanium Gr. 2 | 4/0.9/2.5 | 160 | 2.2913 | 2.291 | — | — |

Ti Gr. 2 was found to be a lead candidate material for many of the applications mentioned above. Anodic polarization tests were conducted to estimate the corrosion rate in the test environment. Potentiodynamic sweeps were carried out in a standard three electrode cell with Titanium Gr. 2 working electrode, platinum gauze counter electrode, and saturated calomel electrode reference electrode. The corrosion potential ($E_{corr}$) was determined to be 0.94V vs SHE in a solution of 4.5M CuCl$_2$/2.5M NaCl at 90° C. The potential was scanned at a rate of 0.5 mV/s from 0.55V to 1.2V. Tafel slopes ($\beta$) and resistance (R) were measured from the V vs log(i) plots generated from the potentiodynamic sweep. Using Eq(1), the corrosion rate ($i_{corr}$) was calculated to be <0.5 mpy (mils per year) which is typically considered high stability in the given operating conditions.

$$R = \beta_a \beta_c / [2.3 * i_{corr} * (\beta_a + \beta_c)] \quad \text{Eq(1)}$$

Example 5

Testing of the AEMs in the Electrochemical Cell

Figure 12:
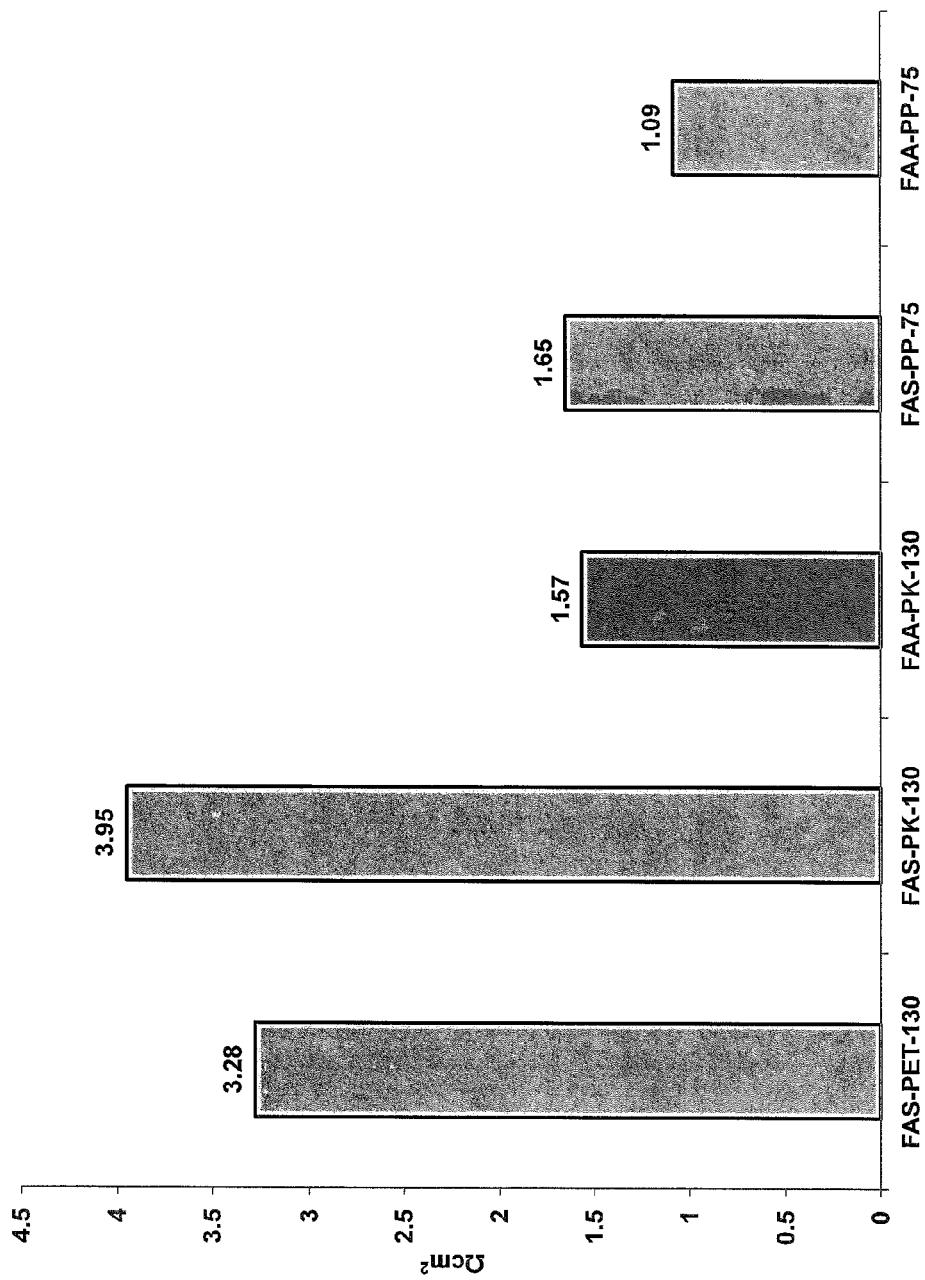
FIG. 12 is an illustrative graph for anion exchange membranes (AEMs), as described in Example 5 herein.

In this study, anion exchange membranes (AEMs) from FuMA-Tech's Fumasep series were tested. The selected AEMs were of the form FAS and FAA with a thickness ranging from 20 um to 130 um and different reinforcements including polyethylene (PET), polypropylene (PP), glass fibers, and polyether ether ketone (PK). The through-plane area resistance was measured using AC impedance. The test setup was a two-electrode flow through cell with Pt-foil electrodes and an active area of 4.91 cm$^2$. The applied DC current was 5 mA with AC amplitude of 1 mA. The frequency sweep was between 35 kHz and 10$^{-3}$ Hz. The test solution was 40 g/L NaCl at 25° C. The results are summarized in FIG. 12. Minimum resistance was seen for FAA-PP-75. It was observed that the resistance was a function of ionomer, reinforcement, thickness, and combinations thereof.

Example 6

Separation of the Metal Salts by Precipitation

In this study, the metal salts in different oxidation state were separated using precipitation technique. The initial composition of the solution was 0.9M of Cu(I)/4.55M of Cu(II)/XM where X=1M, 2.5M and 4M of [NaCl]. The solids were weighed and placed into beakers. DI water was added to make 100 ml volume solutions, which were then heated to 90° C. After 30 min of stirring, the samples were withdrawn for titration measurements (for [Cu(II)] and [total Cu]). The hot mixtures were then left to cool for ~4 hours at room temperature. After the precipitates were formed, they were separated from the residual liquid by filtration. Both materials (permeate liquid and filtrated solid) were analyzed using Cu(I)/Cu(II)/Total Cu titration measurements to evaluate a possible separation of Cu(I) from Cu(II) using precipitation/dissolution.

The concentration of Cu(I) in the cold liquid was found to be approximately the same as in the original hot solution. The absolute [Cu(II)] concentrations of the cold liquid were ~25-30% less than starting [Cu(II)]. Therefore, the CuI:CuII ratio increased in the cold liquid from 0.9M/4.5M to 0.9M/3M. The Cu(I):Cu(II) ratio of the solid filtrate was found to be ~2× less than of the cold liquid and ~1.5× less than of the hot mix, i.e. there was much less Cu(I) in the solid precipitate. Based on these results, it was observed that the Cu(I)/Cu(II) separation efficiency can be improved with liquid separation from solid phase at low temperatures: centrifugation or multiple filtrations.

In the next series of the experiments, three different, 100 ml mixtures of Cu(I)/Cu(II)/NaCl were prepared (1M/3.5M/2.5M, 1M/4.5M/2.5M, and 1M/5.5M/2.5M). The mixtures were thoroughly stirred and heated at 90° C. for full dissolution. Afterwards, 4 ml samples were taken from each mixture and titrated to determine Cu(I) and Cu(II) concentrations. After cooling for about 4 hours, all three mixtures were partially solidified. The liquid phase was separated from solid by simple filtration and the titrations of the permeated liquids and residual solids were carried out.

It was observed that the concentrations of Cu(I) in both the hot solution mixture and cold supernatant were approximately the same, which implied that all the Cu(I) stayed in the liquid phase. The concentration of Cu(II) in the cold supernatant decreased from the hot mix concentration (3.5M to 2.4M, 4.5M to 2.7M, and largest drop in 5.5M to 2.8M). According to both results of titration and visual appearance (blue crystals), the solid precipitate was pure Cu(II) with possible some low levels of NaCl. Negligible Cu(I) might be present as a low-level impurity. This result was confirmed by XRD.

The results of the catalytic performance (reaction with hydrocarbons to form halogenated hydrocarbons) of the metals received by precipitation technique (re-dissolved added water) was tested. The catalytic activities were found to be in line with the catalysis results obtained with metal ions not obtained through precipitation. Samples with 1.46 g metal in solution were run in the reactor under nitrogen @ 160° C. for 60 minutes pressurized to 200 PSI w/ Ethylene at t=60 minutes at pressure 230 PSI. The organic phase was extracted w/ 2 mL EtOAc. The results showed EDC formation along with byproducts.

In another experiment, the metal solution was cooled to 90° C. as compared to cooling to room temperature. A 1M/6.5M/2.5M mixture was heated to 150° C. for 30 min. to equilibrate and then the temperature was lowered to 90° C. where, using a pre-heated filtrating syringe, the liquid and solid were separated. The resulting solutions were then titrated. It was observed that there was no Cu(I) in solid samples. The concentration of liquid phase after filtration was Cu(I)-rich with an approximate Cu(II) concentration around 3M.

Example 7

Separation of the Metal Salts by Kinetic Dissolution

In this experiment, a mixture of Cu(I)/Cu(II)/NaCl at 0.9M/4.5M/2.5M was placed into a beaker. Water was introduced at 20° C. up to 100 ml. 10 ml samples were taken after 1 min, 3 min, 5 min and 30 min. It was observed that the concentration of Cu(I) was close to zero at 1 min and rose to ~0.3M after 30 min while the concentration of Cu(II) was close to 1.2M at 1 min and rose to ~1.8M after 30 min. The change in the color of solution was also observed as function of time. Thus, the ratio of Cu(I):Cu(II) was found to increase with time.

Example 8

Start-Up of the Electrochemical Cell

During start-up of e-chem cell, the current density is increased from zero to the design current density such as, for example, 300 mA/cm$^2$. As the higher operating current density is reached, the anolyte is switched to the process solution comprising of metal halide, such as, copper chloride. Normally, the stat-up solution of the e-chem cell may be sodium sulfate that can avoid the AEM fouling by metal such as copper containing entities at low current densities. However, use of sodium sulfate alone was seen to result in oxygen generation at the anode. The oxygen was found to be deleterious to the anode materials. This experiment shows that the use of ferrous sulfate in association with sodium sulfate suppressed the oxygen generation and resulted in low voltage. Any concentration of Fe(++)=0.1 to saturation can be used. The solution was acidified to prevent iron from getting oxidized by oxygen in air and $Na_2SO_4$ was added to improve the conductivity of the solution. Following Table 3 provides the cell voltage and solution compositions for the experiment with ferrous sulfate and the experiment without ferrous sulfate.

TABLE 3

| Composition of the anode electrolyte | Materials and conditions | Cell Voltage @300 mA/cm$^2$ for start up | Cell Voltage @300 mA/cm$^2$ for process condition | Observation |
|---|---|---|---|---|
| 0.5M $Na_2SO_4$ | Corrugated anode, AEM = FAA-130, 3 mm brine gap | >4 | 2.9 | Gas evolved at anode for start-up |
| 0.5M $Na_2SO_4$, 1M $FeSO_4$, 0.8% $H_2SO_4$ | Corrugated + bridge anode (flat expanded mesh on top of the | 2.1 | 2.5 | No gas at anode during start-up |

TABLE 3-continued

| Composition of the anode electrolyte | Materials and conditions | Cell Voltage @300 mA/cm² for start up | Cell Voltage @300 mA/cm² for process condition | Observation |
|---|---|---|---|---|
| | corrugated anode), AEM = FAA-70, and 1 mm brine gap | | | |

Example 9

Reactor Configuration and Reaction Conditions

A reactor was set up to perform halogenation of ethylene to EDC. An aqueous metal solution containing about 38-40 wt % $CuCl_2$, 4.9-5.1 wt % CuCl and 8.5 wt % NaCl (anolyte) corresponding to about 4.4-4.6M Cu(II)$Cl_2$, 0.4-0.6M Cu(I)Cl, 2.2-2.3M NaCl, was used for the reaction in the reactor. The density of the metal solution was measured by a Coriolis meter at 90° C. The metal solution was preheated to 90° C. in a non-metallic tank and pumped through an oil heater set to 180-195° C. into a reactor pressurized with ethylene. The catalysis reactor was a titanium trickle bed reactor. The reactor dimensions and packing material are described in Table 4 below. The flow rate of the metal solution (anolyte) and the resulting time averaged temperature and pressure parameters in the reactor are also illustrated in Table 4. Ethylene was fed into the reactor to keep a constant pressure. The liquid phase containing the metal solution and the product left the reactor through a liquid level control valve at the bottom of the reactor that ensured a liquid level of 2-5 liter in the bottom of the reactor.

The liquid phase containing the metal solution and product was allowed to decompress to 10-20 psig in the vapor-liquid separator (V-L separator). The vapors were removed and condensed separately by cooling to 5° C. and the condensate of the vapors was collected in a liquid-liquid separator (decanter). It is to be understood that the procedure may also alternatively include first cooling of the vapors in the V-L separator followed by decompression. The EDC product was separated from the water phase in the decanter. The water phase from the decanter contained small amount of products which was measured.

The liquid phase (after removing the vapors) in the V-L separator left the V-L separator through a level control valve at the bottom of the separator and was collected in a non-metallic tank. The metal solution contained a small amount of products which was measured. The metal solution could be recirculated back to the initial non-metallic tank before entering the reactor.

TABLE 4

| Experiment # | 1 | 2 | 3 | 4 | 5 | 6 |
|---|---|---|---|---|---|---|
| Reactor length or height [inch] | 75 | 75 | 98 | 56 | 102 | 102 |
| Reactor diameter [inch] | 6 | 6 | 4 | 4 | 3 | 3 |
| Packing size | ½" | ¼" | ¼" | ¼" | ¼" | 3 mm |
| Packing geometry | Ceramic Saddles | Ceramic Rashig Rings | Ceramic Rashig Rings | Ceramic Rashig Rings | Ceramic Rashig Rings | Glass Spheres |
| Reaction time | 2 h | 1.8 h | 1.4 h | 2 h | 0.75 h | 2 h |
| Time averaged reactor temperature [° C.] | 164 | 162 | 160 | 161 | 162 | 161 |
| Time averaged reactor pressure [psig] | 246 | 245 | 246 | 252 | 263 | 267 |
| Average anolyte flow [kg/h] | 180 | 220 | 216 | 235 | 200 | 230 |
| Density [g/ml] | 1.52 | 1.54 | 1.53 | 1.56 | 1.53 | 1.53 |
| STY Isolated EDC total [mol/l/h] | 0.04 | 0.08 | 0.12 | 0.15 | 0.32 | 0.26 |

The space time yield (STY) was determined by the total of collected product in the EDC phase and the product that was measured in the water condensate phase and the metal solution. The total amount of product was divided by the reaction time at target conditions and the nominal packed reactor volume determined by diameter and height of the packed bed.

Figure 13:
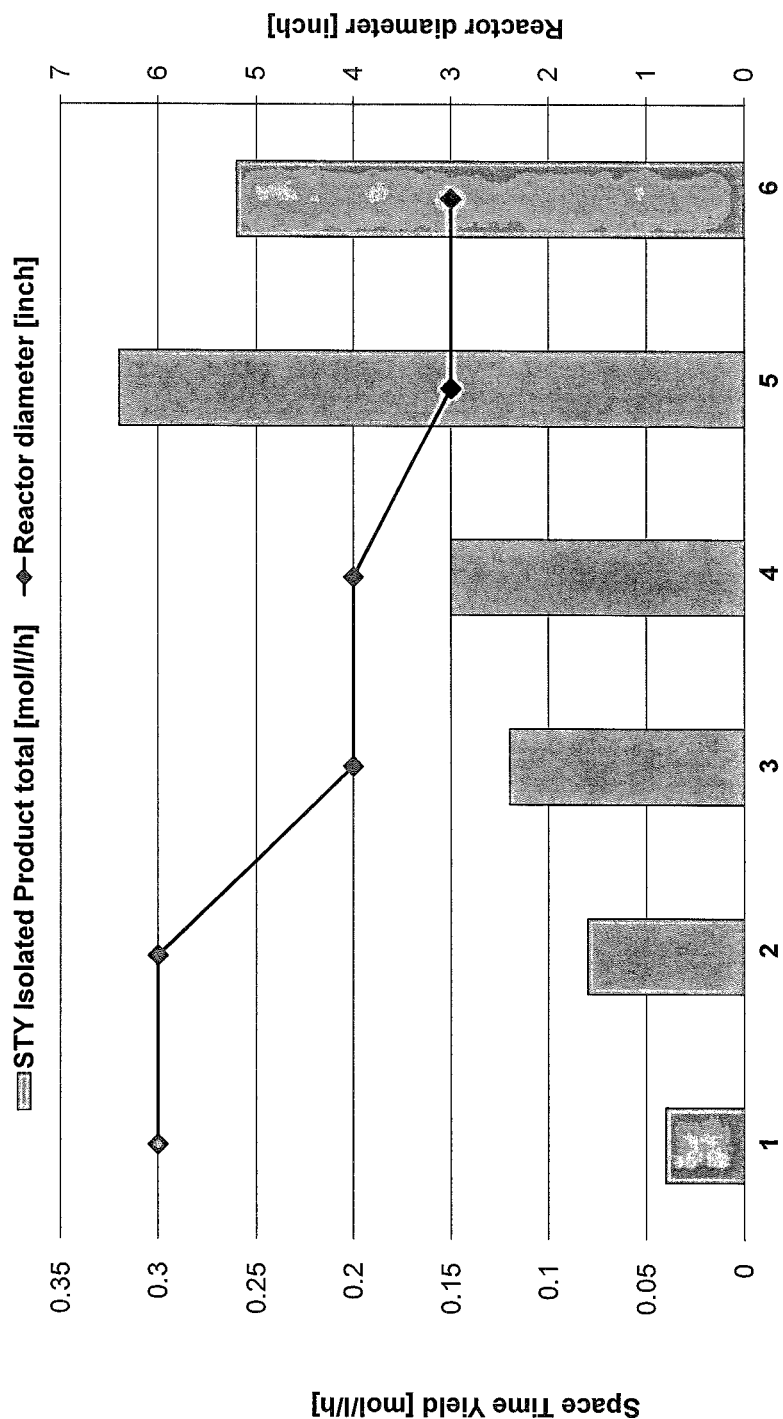
FIG. 13 is an illustrative graph for the effect of reactor configurations on STY of the product, as described in Example 9 herein.

As illustrated in Table 4 and FIG. 13, the STY progressively increased as the length of the reactor increased or the ratio of the length/diameter of the reactor increased. This illustrates the correlation between the length of the reactor or the ratio of the length/diameter of the reactor and the STY of the halogenated product. It was also observed that the type of the packing material as well as the packing material size also affected the STY of the product (experiment 1 and 2 or 5 and 6). Therefore, the reactor configuration including, but not limited to, the length of the reactor, the ratio of the length/diameter of the reactor, packing material type, packing material size, or combinations thereof, affect the STY of the product formed.

Example 10

Reactor Configuration and Reaction Conditions

A reactor was set up to perform halogenation of ethylene to EDC. An aqueous metal solution containing about 39-47 wt % $CuCl_2$, 4.9-6.5 wt % CuCl and 8-9 wt % NaCl corresponding to about 4-5.3 M $CuCl_2$, 0.5-1.2M CuCl and 2.2-2.5M NaCl (anolyte) was used for the reaction in the reactor. The density of the metal solution was measured by a Coriolis meter at 90° C. For each experiment, the metal solution was preheated to 90° C. in a non-metallic tank and pumped through an oil heater set to 175-195° C. into a reactor pressurized with ethylene. The catalysis reactor was a titanium trickle bed reactor with temperature probes at the inlet and outlet of the reactor as well as pressure probes. The reactor dimensions and packing material used are described in Tables 5 and 6 below. The flow rate of the metal solution (anolyte) and the resulting time averaged temperature and pressure parameters in the reactor are also illustrated in Tables 5 and 6. Ethylene was fed into the reactor to keep a constant pressure. The liquid phase containing the metal solution and the product left the reactor through a liquid level control valve at the bottom of the reactor that ensured a liquid level of 2-5 liter in the bottom of the reactor.

The liquid phase exiting the reactor containing the metal solution and product was allowed to decompress to 10-20 psig in the vapor-liquid separator (V-L separator). The vapors were removed and condensed separately by cooling to 5° C. and the condensate of the vapors was collected in a liquid-liquid separator (decanter). The EDC product was separated from the water phase in the decanter. The water phase contained small amount of products which was measured.

The remaining metal solution (after removing the vapors) left the V-L separator through a level control valve at the bottom of the separator and was collected in a non-metallic tank. The metal solution contained a small amount of products which was measured.

TABLE 5

| Experiment # 7 | | | | |
|---|---|---|---|---|
| Reactor length or height [inch] | 102 | 102 | 102 | 102 |
| Reactor diameter [inch] | 3 | 3 | 3 | 3 |
| Packing size | ¼" | ¼" | ¼" | ¼" |
| Packing geometry | Ceramic Rashig Rings | Ceramic Rashig Rings | Ceramic Rashig Rings | Ceramic Rashig Rings |
| Time averaged Reactor pressure [psig] | 266-267 | 266-268 | 266-269 | 266-270 |
| Time averaged Reactor temperature [° C.] | 172 | 167 | 163 | 159 |
| Average anolyte flow [kg/h] | 240 | 240 | 240 | 240 |
| Density [g/ml] | 1.64 | 1.64 | 1.64 | 1.64 |
| STY based on consumed ethylene [mol/l/h] | 0.78 | 0.66 | 0.61 | 0.52 |

TABLE 6

| Experiment # 8 | | | | |
|---|---|---|---|---|
| Reactor length or height [inch] | 102 | 102 | 102 | 102 |
| Reactor diameter [inch] | 3 | 3 | 3 | 3 |
| Packing size | ¼" | ¼" | ¼" | ¼" |
| Packing geometry | Ceramic Rashig Rings | Ceramic Rashig Rings | Ceramic Rashig Rings | Ceramic Rashig Rings |
| Time averaged Reactor pressure [psig] | 266-267 | 266-268 | 266-269 | 266-270 |
| Time averaged Reactor temperature [C.] | 169 | 170 | 170 | 169 |
| Average anolyte flow [kg/h] | 130 | 175 | 240 | 280 |
| Density [g/ml] | 1.65 | 1.65 | 1.65 | 1.65 |
| STY based on consumed ethylene [mol/l/h] | 0.51 | 0.65 | 0.81 | 0.86 |

Experiments #7 and #8, describe two single parameter change experiments. In these experiments, the ethylene flow into reactor and out through the vent was measured with flow meters over a period of 20-40 minutes under steady conditions. The total ethylene consumed was determined by subtracting the total ethylene flow out through the vent from the total ethylene flow into reactor over a time period with steady conditions. The STY was determined by the total amount of ethylene consumed in mol divided by the time period at steady conditions and the nominal packed reactor volume.

As illustrated in Table 5, in experiment #7 as the temperature of the reactor was increased (keeping all the other parameters constant), the reactivity of the ethylene or the ethylene consumption increased. The consumption of the ethylene can be directly correlated to the STY of the EDC product as higher is the amount of ethylene consumed, higher is the amount of EDC formed. Therefore, temperature of the reactor is directly correlated to the STY of the product. The selectivity of the entire run in experiment #7 averaged over all temperature conditions was 86.6 mol % (mol EDC/mol ethylene).

Also illustrated in Table 6 is the effect of the increase in the flow of the metal solution (anolyte) to the reactor on the reactivity of the ethylene or the ethylene consumption. It was observed that as the flow of the anolyte to the reactor increased, the consumption of the ethylene also increased. As explained above, the consumption of the ethylene can be directly correlated to the STY of the EDC product as higher is the amount of ethylene consumed, higher is the amount of EDC formed. Therefore, flow of the anolyte to the reactor is directly correlated to the STY of the product. The selectivity of the entire run in experiment #8 averaged over all flow conditions was 85.6 mol % (mol EDC/mol ethylene).

Example 11

Separation and Purification of the Organic Products

Figure 14:
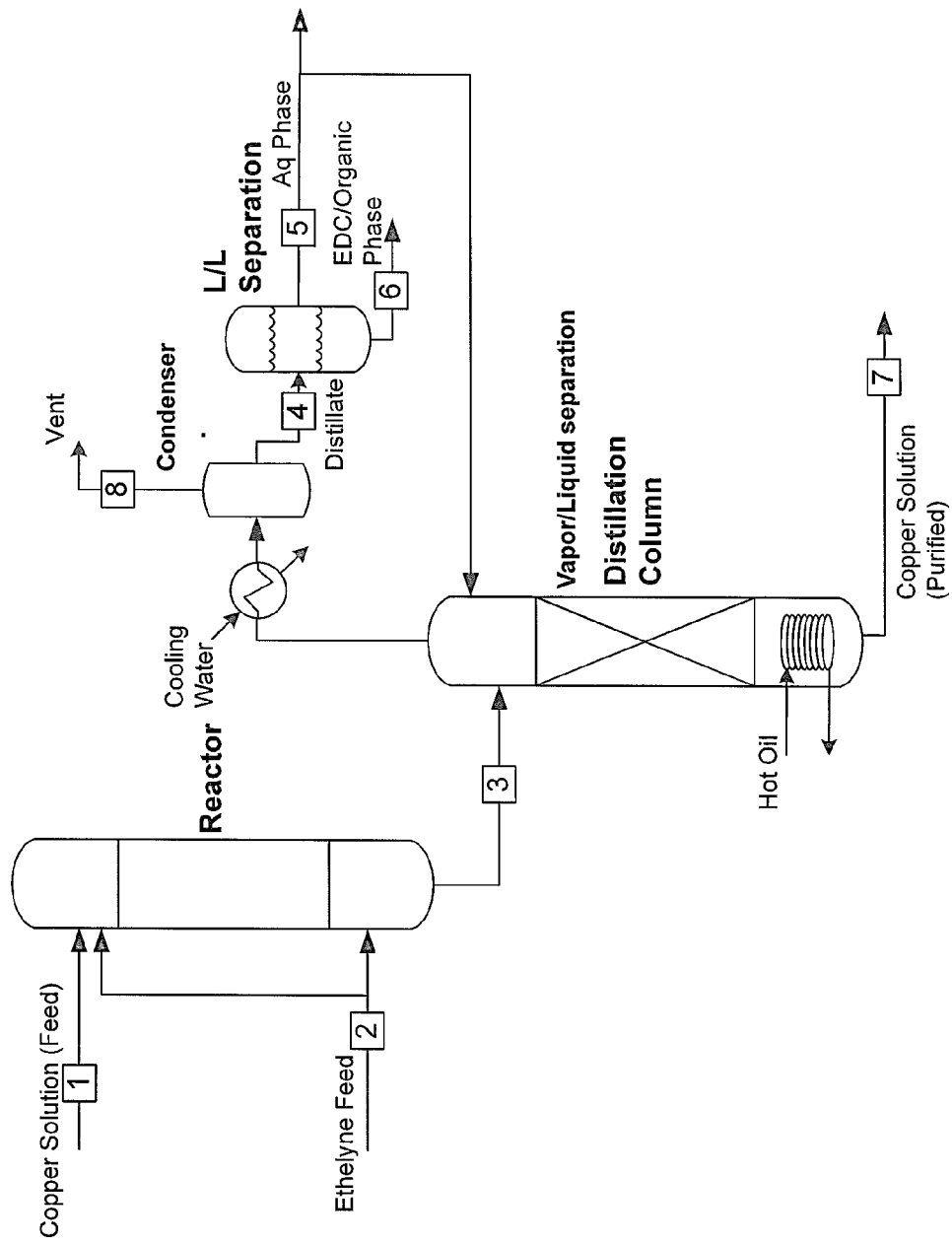
FIG. 14 illustrates separation embodiments, as described in Example 11 herein.

FIG. 14 illustrates a reactor and separation scheme that used a multistage distillation column to recover ethylene dichloride from the reactor product stream. An aqueous copper solution (1) which contained a mixture of Cu(I)Cl and Cu(II)Cl$_2$ was fed to the top of a trickle bed reactor. Ethylene (2) was fed to the bottom and/or top of the reactor. The reactor was constructed of 3" Schedule 40 pipe (inside an insulated section, 8.5' high), packed with ¼" ceramic Raschig rings. The temperature was controlled by preheating the copper feed (1), and the pressure was controlled by feeding pressurized ethylene (2) to maintain a pressure set point. The reactor product (3), which contained the copper solution, the EDC produced in the reactor, and other chlorinated organic by-products, was subjected to a vapor-liquid separation process started by feeding to the top of a distillation column. Steam was generated at the bottom of the distillation column by circulating hot oil through coil (the reboiler) which was in contact with the copper solution at the bottom of the column. The flow rate of the copper solution leaving the column (7) was controlled to keep the solution liquid level above the coil. The contact between the steam going up the column and the liquid copper solution going down the column removed the light components (organics) from the copper solution into the distillate stream (4). The distillate stream was condensed and cooled in a condenser and flowed into the separation vessel where non-condensable vapors/gases were separated. The liquid stream from the separation vessel flowed to a liquid/liquid separation vessel. In the liquid/liquid separation vessel, the distillate separated into two phases, a heavy organic phase containing mainly EDC which was taken as the product (6), and a light aqueous phase which could be recycled back to the top of the column or sent for further processing.

The distillation column was constructed of 3" Schedule 40 pipe, and had a 5' packed section containing ⅜" Intalox ceramic packing. The amount of heat input to the distillation column reboiler was calculated from measuring the flow rate and inlet and outlet temperature of the heating oil. The pressure in the distillation column was controlled by controlling the vent (8) flow rate.

Experiment 1:

The separation system described in FIG. 14 was used for a separation experiment. 280 kg/hr of aqueous copper solution (1) which contained a mixture of Cu(I)Cl and Cu(II)Cl$_2$ was fed to the top of the reactor. Feed temperature was varied during the 2.5 hour run between 165-174° C. and outlet temperature was 152-164° C. correspondingly. Ethylene was fed to the bottom of the reactor by pressure control, controlling the reactor pressure to 270 psig. The distillation column pressure was maintained at 15 psig, and reboiler temperature was at 127° C. The distillate aqueous phase (5) was not recycled back to the column, and instead DI water at the same mass rate was fed to the top of the column, in order to maintain the same copper concentration in stream 7 as in stream 1.

Periodic samples of stream 5 and 7 were taken and analyzed by gas chromatography for EDC, 2-chloroethnol (CE), monochloroacetaldehyde (MCA), dichloroacetaldehyde (DCA), and trichloroacetaldehyde (TCA). The amount of EDC produced (6) was measured.

Figure 15:
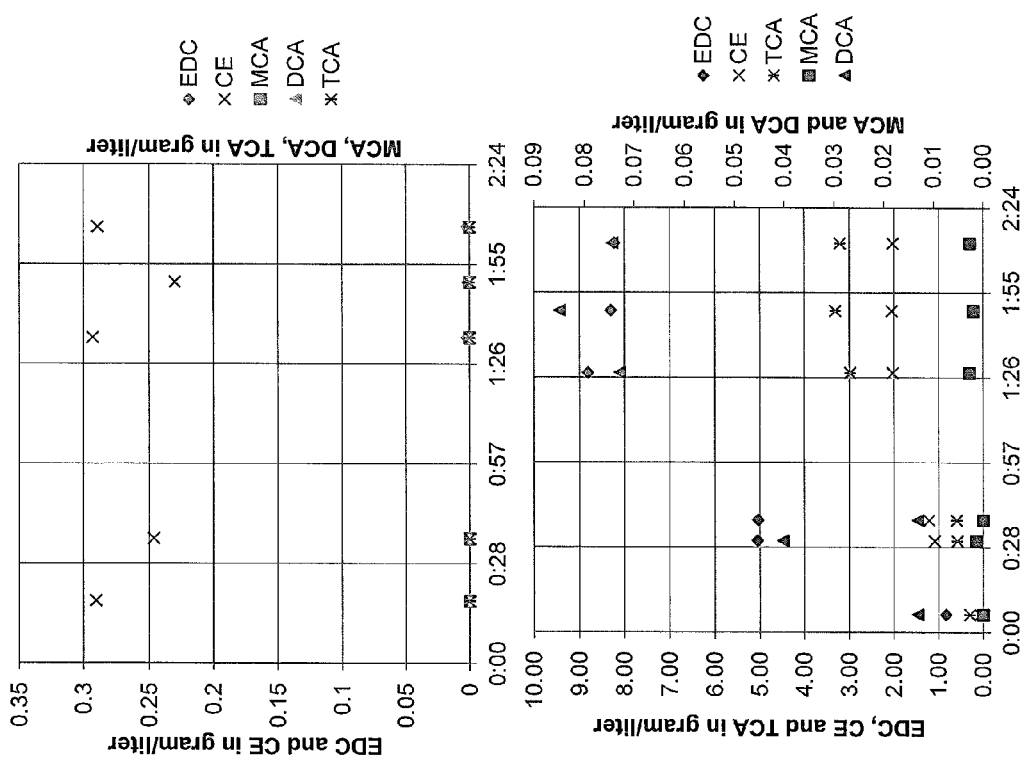
FIG. 15 illustrates separation embodiments, as described in Example 11 herein.

FIG. 15 illustrates the concentration in grams per liter vs. time of the above components in the bottom (7) and aqueous distillate (5) stream over the course of the run. The graph on the top shows concentrations in the bottoms stream (7) and the graph on the bottom shows concentrations in aqueous distillate stream (5).

Table 7 demonstrates the total mass of each component for the duration of the experiment in the combine distillate stream (4) and the bottoms stream (7). The % recovered calculation shows the percent recovered/removal of each component (to the distillate stream) by the distillation column. The percent removal of each component is calculated as the component mass in the distillate over the combined mass in the bottoms and distillate.

It was found that the EDC, MCA, DCA, and TCA were fully recovered in the distillate. For CE removal was lower. An Aspen Plus model of the distillation column shows that a much higher percent removal is expected for MCA and DCA than CE. Therefore it is anticipated that the DCA and MCA in the bottoms streams were originating from CE reacting in the distillation column reboiler and not from the reactor feed to the column (3).

TABLE 7

|  | EDC | CE | MCA | DCA | TCA |
|---|---|---|---|---|---|
| Total gram in Distillate (5) + (6) | 1010.78 | 50.73 | 0.06 | 1.86 | 70.32 |
| Total gram in bottoms stream (7) | 0.33 | 66.61 | 0.00 | 0.00 | 0.00 |
| % Recovered in distillate [(5) + (6)]/ [(5) + (6) + (7)] | 99.97% | 43.24% | 100.00% | 100.00% | 100.00% |

Experiment 2:

The separation system described in FIG. 14 was used for a separation experiment. In this experiment, similar conditions were used as Experiment 1, except that the feed temperature varied during the 3.5 hour run between 167-171° C. and outlet temperature was 155-161° C. correspondingly. Further exception was that the distillate aqueous phase (5) was recycled back to the column and at the end of the run all the aqueous phase in the liquid/liquid separation vessel was sampled. It was observed (Table 8) that the EDC, DCA and TCA were fully recovered in the distillate. For CE, removal was lower than the previous example where the aqueous phase was not recycled.

TABLE 8

|  | EDC | CE | MCA | DCA | TCA |
|---|---|---|---|---|---|
| Total gram in Distillate (5) + (6) | 1189.23 | 8.92 | 0.00 | 0.38 | 1.59 |
| Total gram in bottoms stream (7) | 0.00 | 49.06 | 6.19 | 0.00 | 0.00 |
| % Recovered in distillate [(5) + (6)]/ [(5) + (6) + (7)] | 100.00% | 15.39% | 0.00% | 100.00% | 99.79% |

Experiment 3:

The separation system described in FIG. 14 was used for a separation experiment with few modifications. The distillation column was replaced with a single stage flash distillation vessel. The heat for the flash was supplied by the hot pressurized reactor stream (159° C., 270 psig) flashing into the flash vessel which was maintained at 15 psig. The flash vessel temperature was 119° C. The reactor used was constructed out of 4" schedule 40 pipe with the same packing.

180 kg/hr of aqueous copper solution (1) which contained a mixture of Cu(I)Cl and Cu(II)Cl$_2$ was fed to the top of the reactor in the 30 minutes of the run, for the last hour of the run the flow was increased to 260 Kg/hr. Feed temperature during the 2 hour run was 159° C. and outlet temperature was 161° C. correspondingly. Ethylene was fed to the bottom of the reactor by pressure control, controlling the reactor pressure to 270 psig. The flash vessel pressure was maintained at 15 psig. The distillate aqueous phase (5) was not recycled back to the column.

Periodic samples of stream 5 and 7 were taken and analyzed by gas chromatography for EDC, 2-chloroethnol (CE), monochloroacetaldehyde (MCA), dichloroacetaldehyde (DCA), and trichloroacetaldehyde (TCA). The amount of EDC produced (6) was measured.

Figure 16:
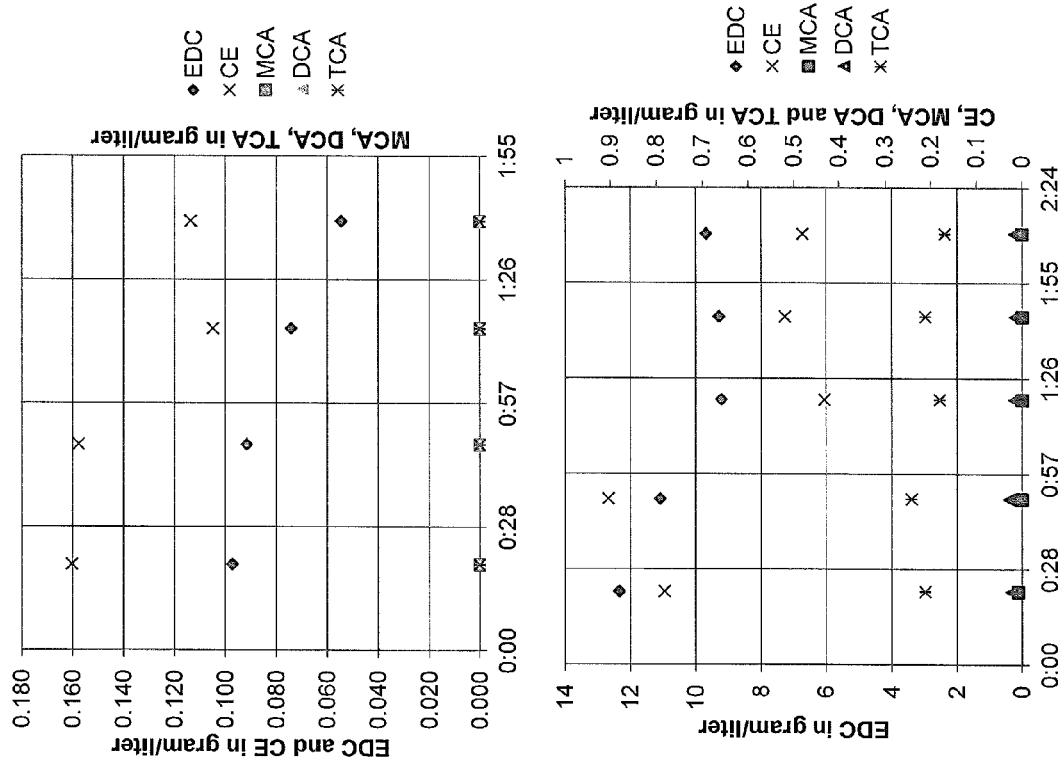
FIG. 16 illustrates separation embodiments, as described in Example 11 herein.

FIG. 16 illustrates the concentration in grams per liter vs. time of the above components in the bottom (7) and aqueous distillate (5) stream over the course of the run. The graph on the top shows concentrations in the bottoms stream (7) and the graph on the bottom shows concentrations in aqueous distillate stream (5).

Table 9 demonstrates the total mass of each component for the duration of the experiment in the combine distillate stream (4) and the bottoms stream (7). The percent removal of each component is calculated as the component mass in the distillate over the combined mass in the bottoms and distillate.

TABLE 9

|  | EDC | CE | MCA | DCA | TCA |
|---|---|---|---|---|---|
| Total gram in Distillate (5) + (6) | 412.71 | 4.20 | 0.00 | 0.13 | 1.39 |
| Total gram in bottoms stream (7) | 21.85 | 37.43 | 0.00 | 0.00 | 0.00 |
| % Recovered in distillate [(5) + (6)]/ [(5) + (6) + (7)] | 94.97% | 10.10% | n/a | 100.00% | 100.00% |

It was observed that the EDC and CE removal was lower than previous examples where a distillation column was used. This can also be seen in FIG. 16 that the EDC concentrations in the bottoms stream (7) were higher than previous examples and CE concentration in distillate (5) was lower.

What is claimed is:

1. A system, comprising:
an electrochemical system comprising an anode chamber comprising an anode in contact with an anode electrolyte comprising CuCl, $CuCl_2$, NaCl, and water wherein the anode is configured to oxidize the CuCl to $CuCl_2$;
a reactor operably connected to the anode chamber and configured to contact the anode electrolyte comprising CuCl, $CuCl_2$, NaCl, and water with ethylene to form one or more organic compounds comprising ethylene dichloride (EDC) and chloroethanol (CE) where $CuCl_2$ reduces to CuCl in an aqueous medium, wherein the reactor is configured to exit vapor stream comprising EDC and liquid stream comprising EDC, CE, CuCl, $CuCl_2$, NaCl, and water; and
a separator configured to separate and purify the one or more organic compounds comprising ethylene dichloride (EDC) and chloroethanol (CE) from the aqueous medium comprising CuCl, $CuCl_2$, NaCl, and water wherein the separator comprises
vapor-liquid separation system operably connected to the reactor and configured to separate the liquid stream exiting the reactor into a vapor stream comprising EDC and CE and a liquid stream comprising EDC, CE, CuCl, $CuCl_2$, NaCl, and water;
compression-cooling system operably connected to the reactor and configured to condense the vapor stream comprising EDC exiting the reactor to a liquid stream;
a liquid-liquid separation system operably connected to the vapor-liquid separation system and the compression-cooling system configured to separate the liquid stream exiting the vapor-liquid separation system and the compression-cooling system into a first liquid stream comprising EDC and CE and a second liquid stream comprising CuCl, $CuCl_2$, NaCl, and water, and
a scrubbing system operably connected to the vapor-liquid separation system and/or operably connected to the liquid-liquid separation system and configured to react an alkali with the liquid stream exiting the vapor-liquid separation system and/or the second liquid stream exiting the liquid-liquid separation system,
to separate the one or more organic compounds comprising EDC and CE and the aqueous medium comprising CuCl, $CuCl_2$, NaCl, and water, wherein the aqueous medium obtained after the separator comprises less than about 1% or no organic compound.

2. The system of claim 1, wherein the separator further comprises reactive separation reactor system, purification subprocess system, adsorbent, or combinations thereof.

3. The system of claim 1, wherein the vapor-liquid separation system comprises flash column, a distillation column, or combination thereof.

4. The system of claim 1, wherein the liquid-liquid separation system comprises decanter, extraction unit, or combination thereof.

5. The system of claim 1, wherein the alkali is NaOH.

6. The system of claim 1 further comprising a byproduct removal column operably connected to the scrubbing system and configured to remove heavier impurities from liquid stream from the scrubbing system.

7. The system of claim 6, further comprising a fractionating column operably connected to the byproduct removal column and configured to fractionate overhead product to remove lighter impurities.

8. The system of claim 1, further comprising purification subprocess system operably connected to the scrubbing system and/or operably connected to the liquid-liquid separation system and configured to remove water content from a liquid stream exiting the scrubbing system and/or the first liquid stream exiting the liquid-liquid separation system.

9. The system of claim 8, wherein the purification subprocess system comprises decanter, sorbent, distillation column, or combinations thereof.

10. The system of claim 1, wherein the reactor is a reactive separation reactor selected from the group consisting of reactive distillation reactor, reactive extraction reactor, or combination thereof.

11. The system of claim 8, wherein the liquid-liquid separation system comprises decanter, extraction unit, or combination thereof the vapor-liquid separation system comprises flash drum, a distillation column, or combination thereof and/or the purification subprocess system comprises decanter, sorbent, distillation column, or combinations thereof.

12. The system of claim 1, wherein the separator is configured to produce the EDC with more than about 90% yield and/or more than about 90% purity.

* * * * *